(12) United States Patent
Sack et al.

(10) Patent No.: US 12,109,128 B2
(45) Date of Patent: Oct. 8, 2024

(54) COILING IMPLANTABLE PROSTHESES AND METHODS FOR IMPLANTING

(71) Applicant: JMEA Corporation, North Potomac, MD (US)

(72) Inventors: James A. Sack, Elverson, PA (US); Jack Y. Yeh, North Potomac, MD (US)

(73) Assignee: JMEA Corporation, North Potomac, MD (US)

( * ) Notice: Subject to any disclaimer, the term of this patent is extended or adjusted under 35 U.S.C. 154(b) by 0 days.

(21) Appl. No.: 18/314,883

(22) Filed: May 10, 2023

(65) Prior Publication Data
US 2023/0355403 A1 Nov. 9, 2023

Related U.S. Application Data

(60) Continuation of application No. 17/663,469, filed on May 16, 2022, now Pat. No. 11,672,673, which is a
(Continued)

(51) Int. Cl.
*A61F 2/46* (2006.01)
*A61F 2/44* (2006.01)
*A61F 2/30* (2006.01)

(52) U.S. Cl.
CPC ............ *A61F 2/4611* (2013.01); *A61F 2/442* (2013.01); *A61F 2/4425* (2013.01);
(Continued)

(58) Field of Classification Search
CPC .... A61F 2/44; A61F 2002/4415; A61F 2/442; A61F 2/4425; A61F 2002/443;
(Continued)

(56) References Cited

U.S. PATENT DOCUMENTS 3,741,205 A 6/1973 Markolf et al.
4,407,006 A 9/1983 Holick et al.
(Continued)

FOREIGN PATENT DOCUMENTS

FR 2712486 A1 5/1995

OTHER PUBLICATIONS

Amendment accompanying Request for Continued Examination filed Jul. 19, 2010 in U.S. Appl. No. 12/038,613.
(Continued)

*Primary Examiner* — Larry E Waggle, Jr.
(74) *Attorney, Agent, or Firm* — Plumsea Law Group, LLC

(57) ABSTRACT

An implantable prosthesis that includes a biased coiling member and a conforming coiling member. The biased coiling member may be biased to curve from a substantially linear configuration to a nonlinear configuration. The conforming coiling member may be engaged with and curved by the biased coiling member from the substantially linear configuration to the nonlinear configuration. The biased coiling member may define a longitudinal axis when in the substantially linear configuration. The biased coiling member and the conforming coiling member may move relative to each other along the longitudinal axis. The prosthesis may be implanted in a surgical procedure that minimizes incision sizes and may be considered less invasive than typical implant procedures, especially spinal implant procedures.

22 Claims, 65 Drawing Sheets

Related U.S. Application Data continuation of application No. 16/987,566, filed on Aug. 7, 2020, now Pat. No. 11,331,198, which is a continuation of application No. 15/889,704, filed on Feb. 6, 2018, now Pat. No. 10,751,195, which is a division of application No. 14/882,633, filed on Oct. 14, 2015, now Pat. No. 9,901,457.

(60) Provisional application No. 62/064,603, filed on Oct. 16, 2014.

(52) U.S. Cl.
CPC .. *A61F 2/4455* (2013.01); *A61F 2002/30293* (2013.01); *A61F 2002/30507* (2013.01); *A61F 2002/30556* (2013.01); *A61F 2002/30573* (2013.01); *A61F 2002/30971* (2013.01); *A61F 2002/4415* (2013.01); *A61F 2002/443* (2013.01); *A61F 2002/448* (2013.01); *A61F 2002/4485* (2013.01)

(58) Field of Classification Search
CPC .............. A61F 2/4455; A61F 2002/448; A61F 2002/4485; A61F 2/4611; A61F 2002/30293; A61F 2002/30556
See application file for complete search history.

(56) References Cited

U.S. PATENT DOCUMENTS

| | | | |
|---|---|---|---|
| 4,834,757 A | 5/1989 | Brantigan | |
| 5,171,280 A | 12/1992 | Baumgartner | |
| 5,190,545 A | 3/1993 | Corsi et al. | |
| 5,306,310 A | 4/1994 | Siebels | |
| 5,405,391 A | 4/1995 | Henderson et al. | |
| 5,423,826 A | 6/1995 | Coates et al. | |
| 5,439,464 A | 8/1995 | Shapiro | |
| 5,514,181 A | 5/1996 | Light et al. | |
| 5,545,165 A | 8/1996 | Biedermann et al. | |
| 5,595,621 A | 1/1997 | Light et al. | |
| 5,676,667 A | 10/1997 | Hausman | |
| 5,676,702 A | 10/1997 | Ratron | |
| 5,902,231 A | 5/1999 | Foley et al. | |
| 5,919,235 A | 7/1999 | Husson et al. | |
| 5,976,146 A | 11/1999 | Ogawa et al. | |
| 6,264,656 B1 | 7/2001 | Michelson | |
| 6,273,889 B1 | 8/2001 | Richelsoph | |
| 6,371,968 B1 | 4/2002 | Kogasaka et al. | |
| 6,432,106 B1 | 8/2002 | Fraser | |
| 6,436,103 B1 | 8/2002 | Suddaby | |
| 6,447,512 B1 | 9/2002 | Landry et al. | |
| 6,488,710 B2 | 12/2002 | Besselink | |
| 6,524,312 B2 | 2/2003 | Landry et al. | |
| 6,530,926 B1 | 3/2003 | Davison | |
| 6,533,790 B1 | 3/2003 | Liu | |
| 6,565,571 B1 | 5/2003 | Jackowski et al. | |
| 6,610,094 B2 | 8/2003 | Husson | |
| 6,616,671 B2 | 9/2003 | Landry et al. | |
| 6,620,196 B1 | 9/2003 | Trieu | |
| 6,656,178 B1 | 12/2003 | Veldhuizen et al. | |
| 6,660,037 B1 | 12/2003 | Husson et al. | |
| 6,800,084 B2 | 10/2004 | Davison et al. | |
| 6,811,558 B2 | 11/2004 | Davison et al. | |
| 6,830,589 B2 | 12/2004 | Erickson | |
| 6,913,622 B2 | 7/2005 | Gjunter | |
| 7,569,233 B2 | 8/2009 | Malaviya et al. | |
| 7,799,089 B2 | 9/2010 | Plouhar et al. | |
| 7,901,460 B2 | 3/2011 | Sherman | |
| 7,922,767 B2 | 4/2011 | Sack et al. | |
| 8,197,548 B2 | 6/2012 | Sack et al. | |
| 8,241,357 B2 | 8/2012 | Bhatnagar et al. | |
| 8,257,395 B2 | 9/2012 | Bhatnagar et al. | |
| 8,435,268 B2 | 5/2013 | Thompson et al. | |
| 8,518,117 B2 | 8/2013 | Sack et al. | |
| 8,518,118 B2 | 8/2013 | Sack et al. | |
| 8,591,583 B2 * | 11/2013 | Schaller | A61B 17/8852 606/279 |
| 8,696,753 B2 | 4/2014 | Sack et al. | |
| 9,060,870 B2 | 6/2015 | Milella, Jr. | |
| 9,901,457 B2 | 2/2018 | Sack et al. | |
| 10,039,647 B2 | 8/2018 | Sack et al. | |
| 10,751,195 B2 | 8/2020 | Sack et al. | |
| 10,765,526 B2 | 9/2020 | Sack et al. | |
| 11,331,198 B2 | 5/2022 | Sack et al. | |
| 11,672,673 B2 | 6/2023 | Sack et al. | |
| 2002/0107573 A1 | 8/2002 | Steinberg | |
| 2002/0198533 A1 | 12/2002 | Geisler et al. | |
| 2003/0018390 A1 | 1/2003 | Husson | |
| 2003/0073998 A1 | 4/2003 | Pagliuca et al. | |
| 2003/0135216 A1 | 7/2003 | Sevrain | |
| 2003/0171753 A1 | 9/2003 | Collins et al. | |
| 2003/0175075 A1 | 9/2003 | Garrison | |
| 2003/0225409 A1 | 12/2003 | Freid et al. | |
| 2004/0034351 A1 | 2/2004 | Sherman et al. | |
| 2004/0059431 A1 | 3/2004 | Plouhar et al. | |
| 2004/0064144 A1 | 4/2004 | Johnson et al. | |
| 2004/0082960 A1 | 4/2004 | Davison | |
| 2004/0106924 A1 | 6/2004 | Ralph et al. | |
| 2004/0116931 A1 | 6/2004 | Carlson | |
| 2004/0127902 A1 | 7/2004 | Suzuki et al. | |
| 2004/0176842 A1 | 9/2004 | Middleton et al. | |
| 2004/0186482 A1 | 9/2004 | Kolb et al. | |
| 2004/0204716 A1 | 10/2004 | Fanger et al. | |
| 2004/0204717 A1 | 10/2004 | Fanger et al. | |
| 2004/0215199 A1 | 10/2004 | Zinkel | |
| 2004/0215341 A1 | 10/2004 | Sybert et al. | |
| 2004/0220669 A1 | 11/2004 | Studer | |
| 2004/0230309 A1 | 11/2004 | Dimauro et al. | |
| 2004/0249459 A1 | 12/2004 | Ferree | |
| 2004/0253185 A1 | 12/2004 | Herweck et al. | |
| 2005/0004573 A1 | 1/2005 | Abdou | |
| 2005/0015088 A1 | 1/2005 | Ringeisen | |
| 2005/0043801 A1 | 2/2005 | Trieu et al. | |
| 2005/0090822 A1 | 4/2005 | Dipoto | |
| 2005/0119750 A1 | 6/2005 | Studer | |
| 2005/0171610 A1 | 8/2005 | Humphreys et al. | |
| 2006/0041313 A1 | 2/2006 | Allard et al. | |
| 2006/0111715 A1 | 5/2006 | Jackson | |
| 2006/0142858 A1 | 6/2006 | Colleran et al. | |
| 2006/0149279 A1 | 7/2006 | Mathews | |
| 2006/0229615 A1 | 10/2006 | Abdou et al. | |
| 2006/0264948 A1 | 11/2006 | Williams | |
| 2007/0010826 A1 | 1/2007 | Rhoda et al. | |
| 2007/0093906 A1 | 4/2007 | Hudgins et al. | |
| 2007/0123986 A1 | 5/2007 | Schaller | |
| 2007/0129811 A1 | 6/2007 | Plouhar et al. | |
| 2007/0150064 A1 | 6/2007 | Ruberte et al. | |
| 2007/0233071 A1 | 10/2007 | Dewey et al. | |
| 2007/0270812 A1 | 11/2007 | Peckham | |
| 2007/0270858 A1 | 11/2007 | Trieu et al. | |
| 2008/0058952 A1 | 3/2008 | Trieu et al. | |
| 2008/0133012 A1 | 6/2008 | McGuckin et al. | |
| 2008/0140199 A1 | 6/2008 | Briest | |
| 2008/0234687 A1 | 9/2008 | Schaller et al. | |
| 2008/0255664 A1 | 10/2008 | Hogendijk et al. | |
| 2008/0269893 A1 | 10/2008 | Bhatnagar et al. | |
| 2008/0312743 A1 | 12/2008 | Vila et al. | |
| 2009/0012617 A1 | 1/2009 | White et al. | |
| 2009/0012621 A1 | 1/2009 | Sack et al. | |
| 2009/0012622 A1 | 1/2009 | Sack et al. | |
| 2009/0012623 A1 | 1/2009 | Sack et al. | |
| 2009/0048675 A1 | 2/2009 | Bhatnagar et al. | |
| 2009/0082810 A1 | 3/2009 | Bhatnagar et al. | |
| 2010/0016967 A1 | 1/2010 | Weiss et al. | |
| 2010/0310623 A1 | 12/2010 | Laurencin et al. | |
| 2011/0093074 A1 | 4/2011 | Glerum et al. | |
| 2012/0165944 A1 | 6/2012 | McGuckin, Jr. | |
| 2012/0221107 A1 | 8/2012 | Sack et al. | |
| 2012/0269873 A1 | 10/2012 | Kerr et al. | |
| 2013/0035762 A1 | 2/2013 | Siegal et al. | |
| 2013/0110232 A1 | 5/2013 | Hupin et al. | |
| 2013/0204374 A1 | 8/2013 | Milella, Jr. | |
| 2014/0243980 A1 | 8/2014 | Sack et al. | |

(56) References Cited

U.S. PATENT DOCUMENTS

| | | | |
|---|---|---|---|
| 2014/0277481 A1* | 9/2014 | Lee | A61F 2/4601 623/17.16 |
| 2015/0173910 A1 | 6/2015 | Siegal et al. | |
| 2021/0038405 A1 | 2/2021 | Sack et al. | |

OTHER PUBLICATIONS

Amendment accompanying Request for Continued Examination filed Jul. 19, 2010 in U.S. Appl. No. 12/038,629.
Final Office Action mailed Apr. 1, 2010 for U.S. Appl. No. 11/774,584.
Final Office Action mailed Apr. 1, 2010 in U.S. Appl. No. 12/038,629.
Final Office Action mailed Apr. 2, 2010 in U.S. Appl. No. 12/038,613.
Final Office Action mailed May 7, 2010 in U.S. Appl. No. 11/859,386.
International Search Report and Written Opinion for Application No. PCT/US2008/053327, mailed Aug. 15, 2008.
International Search Report and Written Opinion mailed Aug. 12, 2009 from PCT Application No. PCT/US2008/069141.
Interview Summary mailed Feb. 20, 2013 in U.S. Appl. No. 12/038,613.
Interview Summary mailed Feb. 20, 2013 in U.S. Appl. No. 12/038,629.
Interview Summary mailed Dec. 23, 2009 in U.S. Appl. No. 12/038,613.
Interview Summary mailed Dec. 23, 2009 in U.S. Appl. No. 12/038,629.
Notice of Allowance mailed Mar. 9, 2012 for U.S. Appl. No. 12/118,503.
Notice of Allowance mailed Apr. 24, 2013 in U.S. Appl. No. 12/038,629.
Notice of Allowance mailed Apr. 25, 2013 in U.S. Appl. No. 12/038,613.
Office Action mailed Aug. 10, 2009 for U.S. Appl. No. 11/859,386.
Office Action mailed Sep. 17, 2009 in U.S. Appl. No. 12/038,613.
Office Action mailed Sep. 17, 2009 in U.S. Appl. No. 12/038,629.
Office Action mailed Aug. 19, 2009 for U.S. Appl. No. 11/774,584.
Office Action mailed Nov. 20, 2012 in U.S. Appl. No. 12/038,613.
Office Action mailed Nov. 26, 2012 in U.S. Appl. No. 12/038,629.
Office Action mailed Sep. 26, 2011 for U.S. Appl. No. 12/118,503.
Office Action mailed Jun. 8, 2009 for U.S. Appl. No. 11/774,584.
Office Action mailed Jun. 8, 2009 in U.S. Appl. No. 12/038,613.
Office Action mailed Jun. 8, 2009 in U.S. Appl. No. 12/038,629.
Official Communication dated Oct. 7, 2014 in European Patent Application No. 08781335.8.
Request for Continued Examination mailed Jul. 19, 2010 in U.S. Appl. No. 12/038,613.
Request for Continued Examination mailed Jul. 19, 2010 in U.S. Appl. No. 12/038,629.
Response to Office Action filed Jul. 8, 2009 for U.S. Appl. No. 11/774,584.
Response to Office Action filed Dec. 17, 2009 for U.S. Appl. No. 11/774,584.
Response to Office Action filed Feb. 20, 2013 in U.S. Appl. No. 12/038,613.
Response to Office Action filed Jan. 25, 2012 for U.S. Appl. No. 12/118,503.
Response to Office Action filed Feb. 26, 2013 in U.S. Appl. No. 12/038,629.
Response to Office Action filed Jul. 8, 2009 in U.S. Appl. No. 12/038,613.
Response to Office Action filed Jul. 8, 2009 in U.S. Appl. No. 12/038,629.
Response to Office Action filed Dec. 17, 2009 in U.S. Appl. No. 12/038,613.
Response to Office Action filed Dec. 17, 2009 in U.S. Appl. No. 12/038,629.
Response to Supplementary European Search Report filed Oct. 5, 2012 in European Patent Application No. 08781335.8.
Supplementary European Search Report mailed Mar. 7, 2012 in European Patent Application No. 08781335.8.
International Search Report and Written Opinion mailed Jan. 25, 2016, from International Application No. PCT/US2015/055733.
PCT Notification Concerning Transmittal of International Preliminary Report on Patentability (IPRP), International Application No. PCT/US2015/055733, from the International Bureau dated Apr. 27, 2017.

* cited by examiner

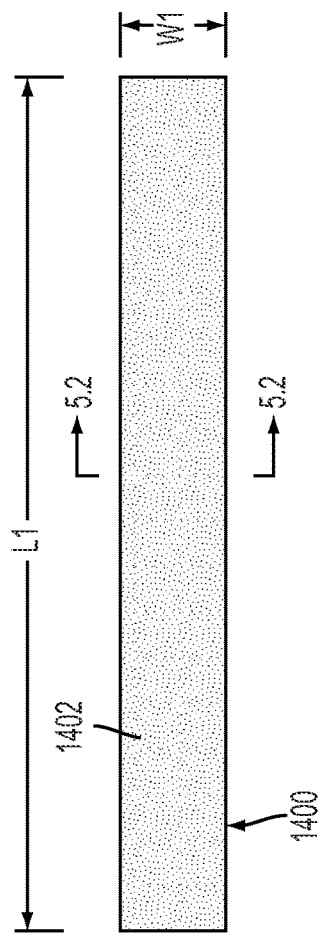
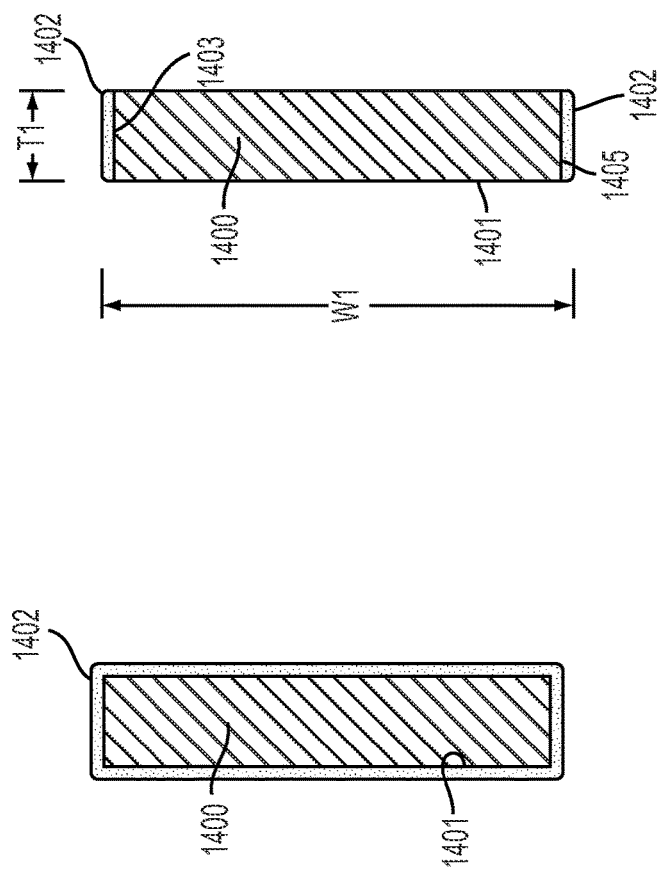
FIG. 5.1
FIG. 5.2
FIG. 5.3

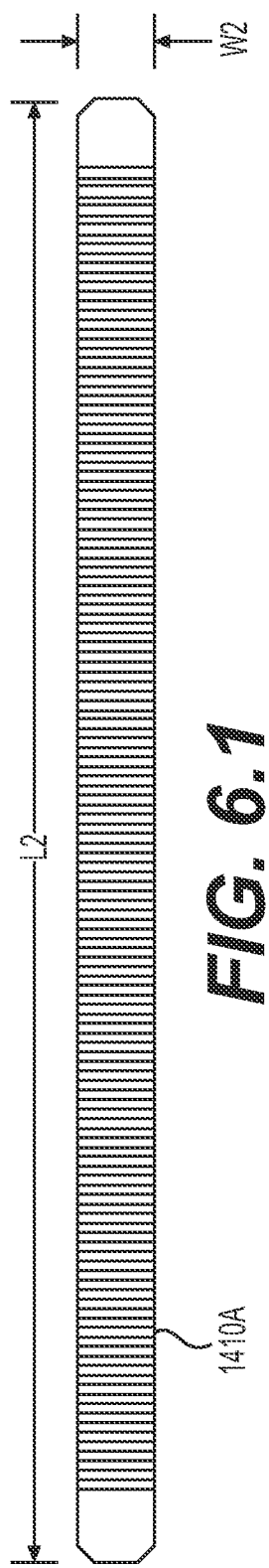
FIG. 6.1
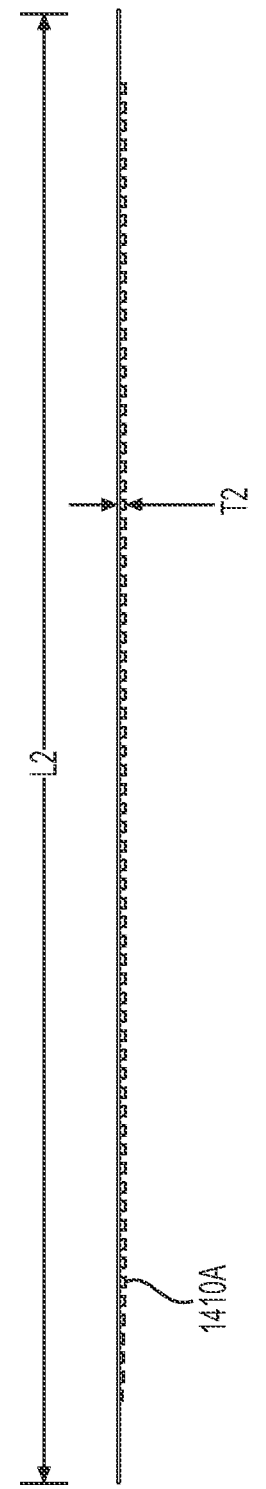
FIG. 6.2

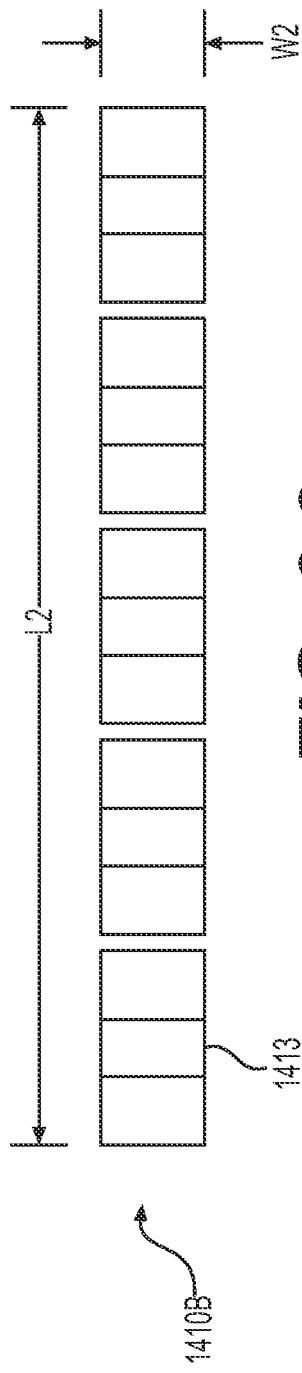
FIG. 6.3
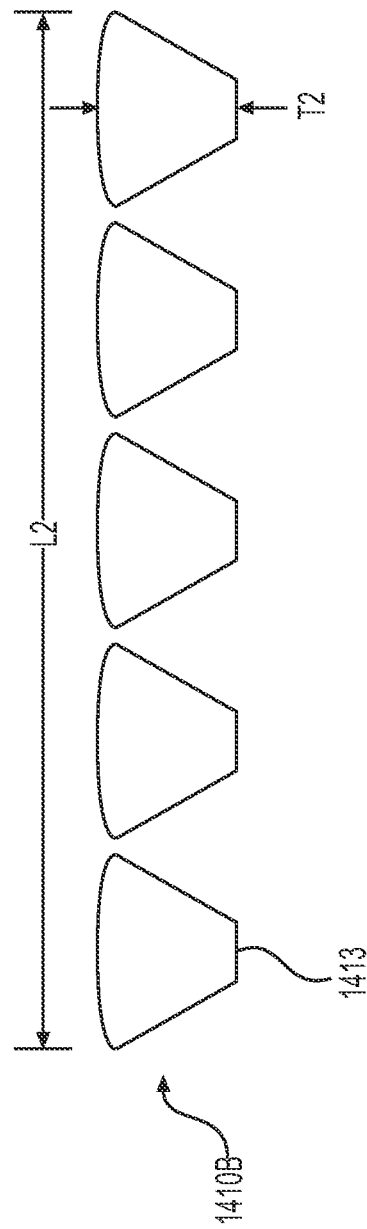
FIG. 6.4

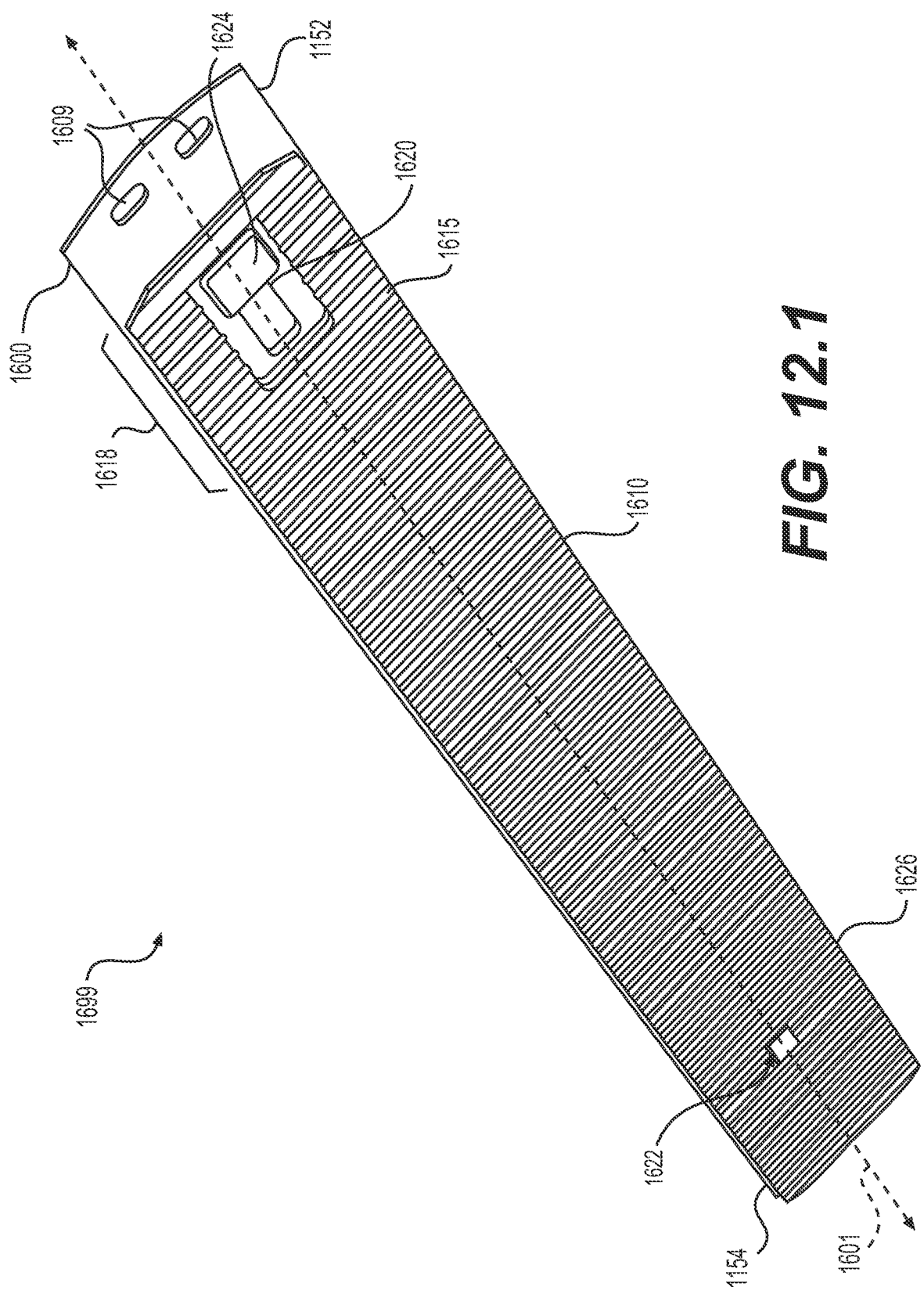
FIG. 12.1

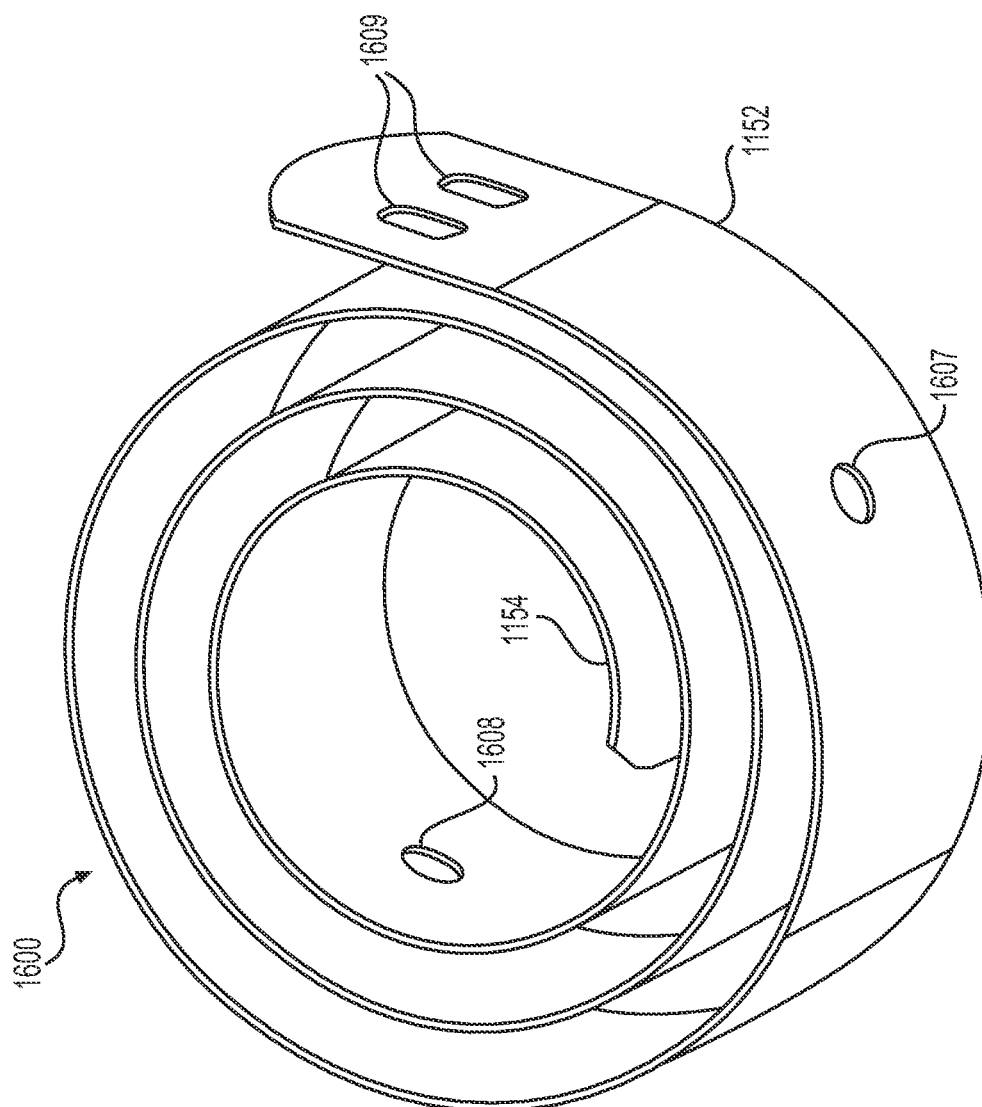
FIG. 12.2

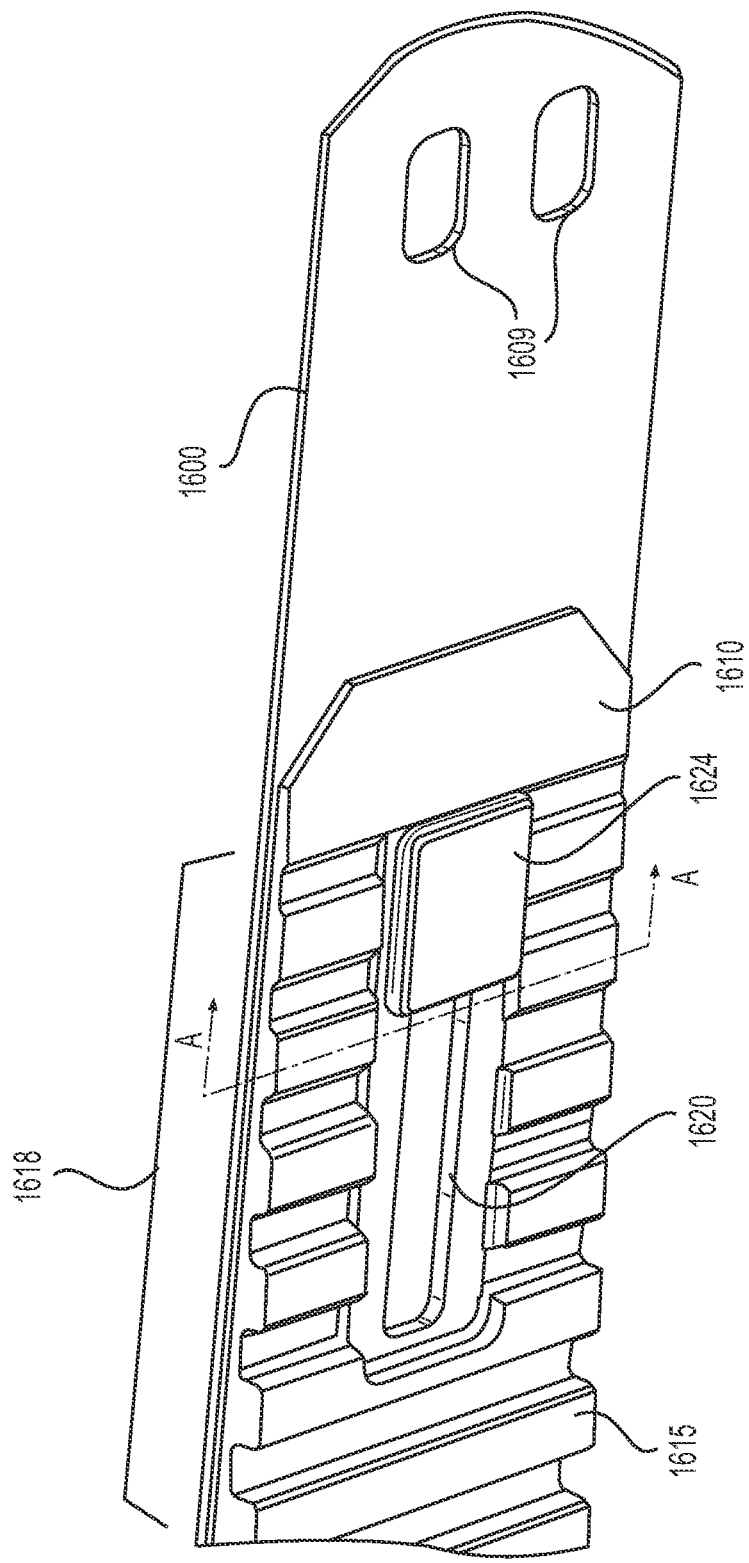
FIG. 12.3

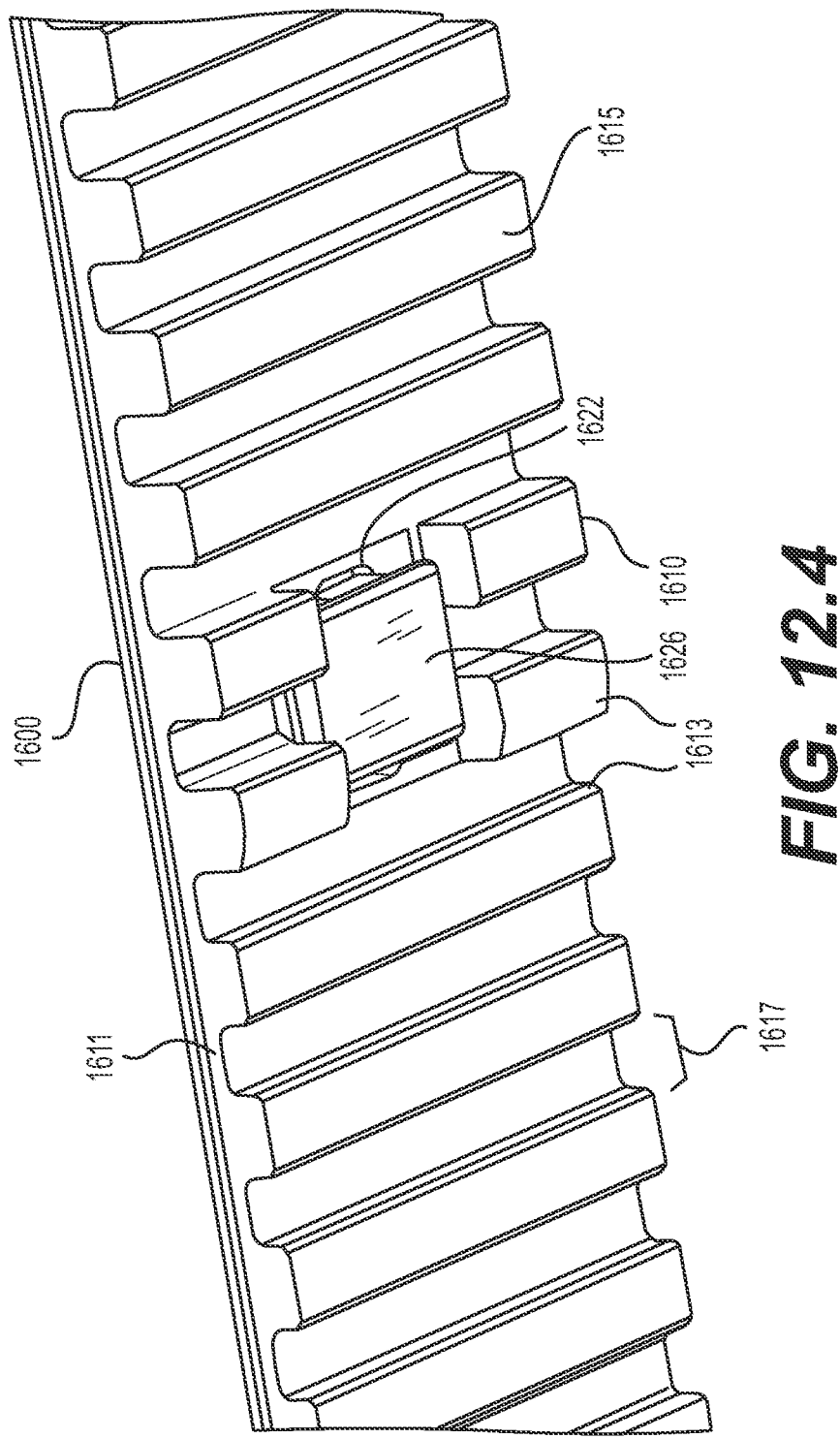
FIG. 12.4

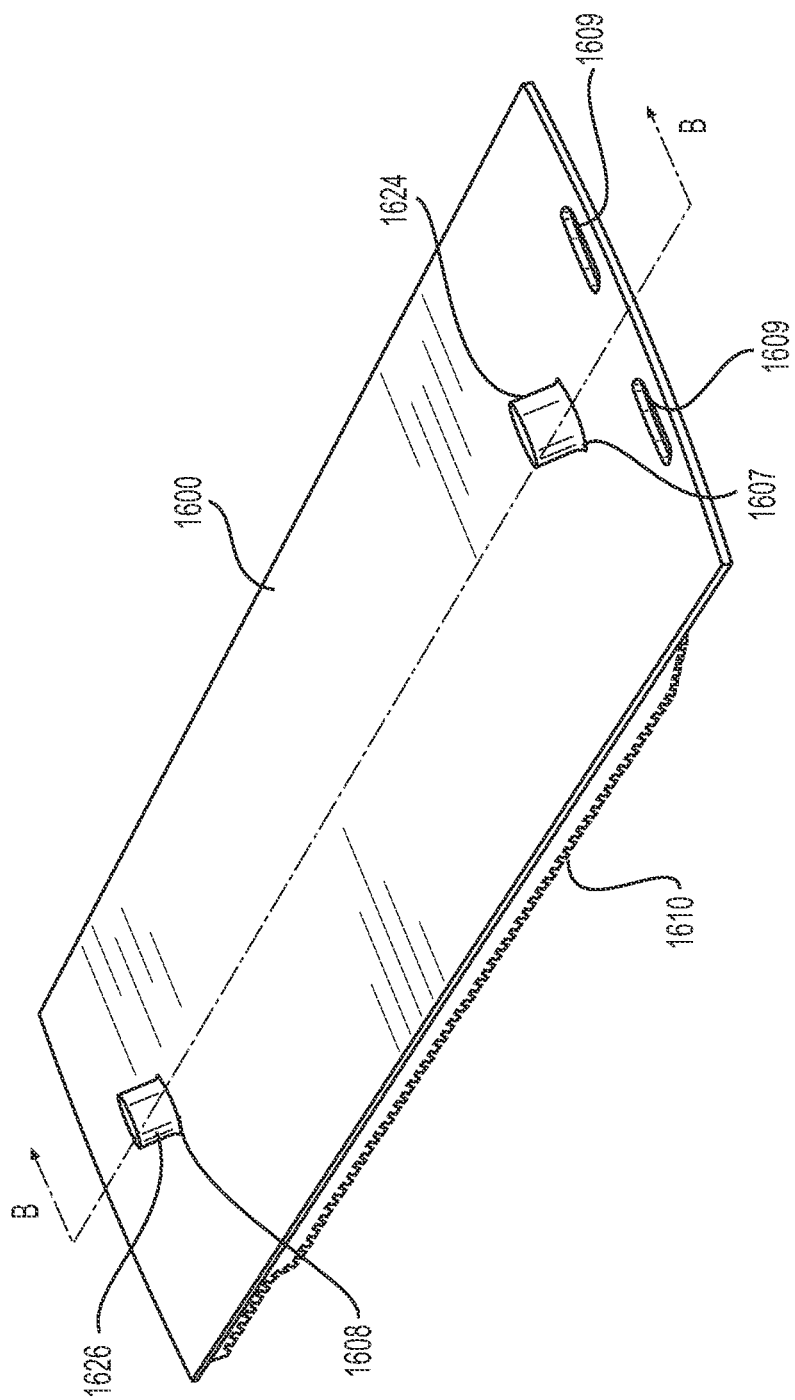
FIG. 12.5

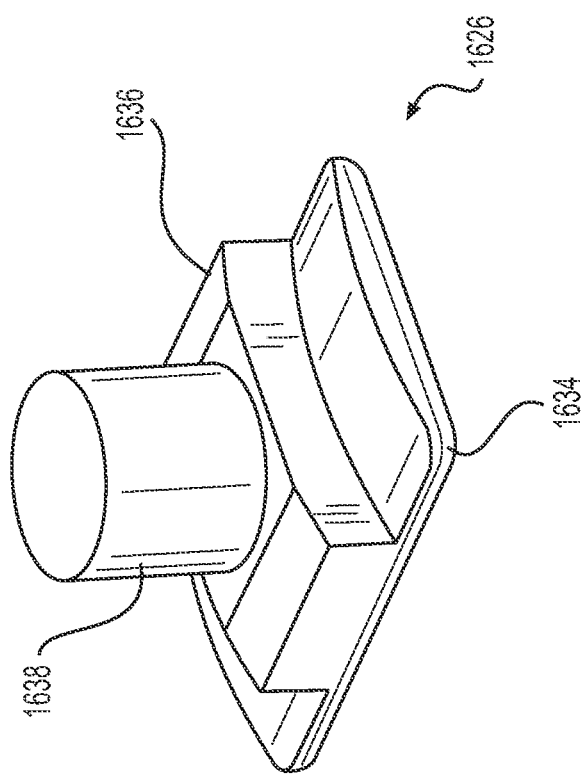
FIG. 12.7
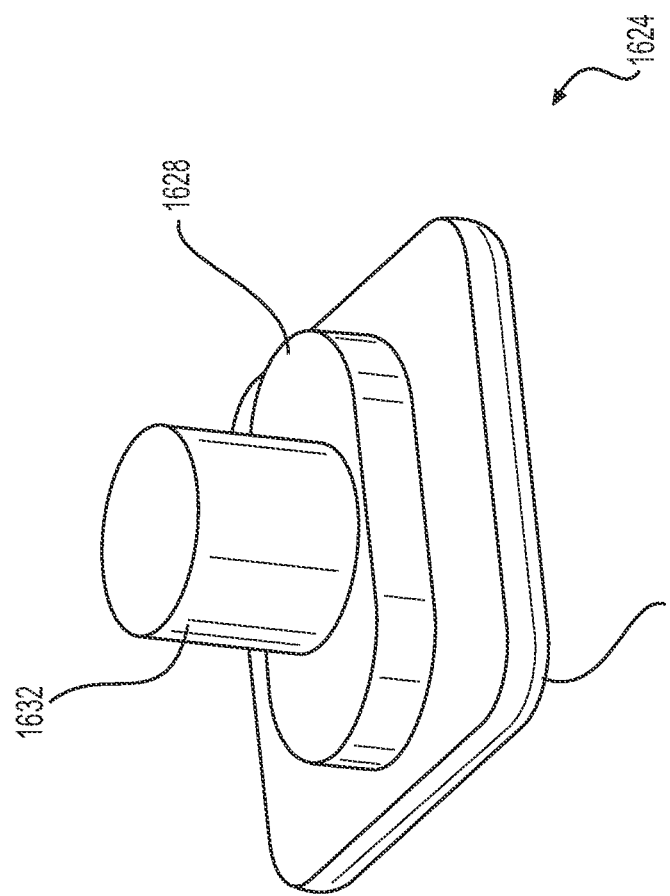
FIG. 12.6

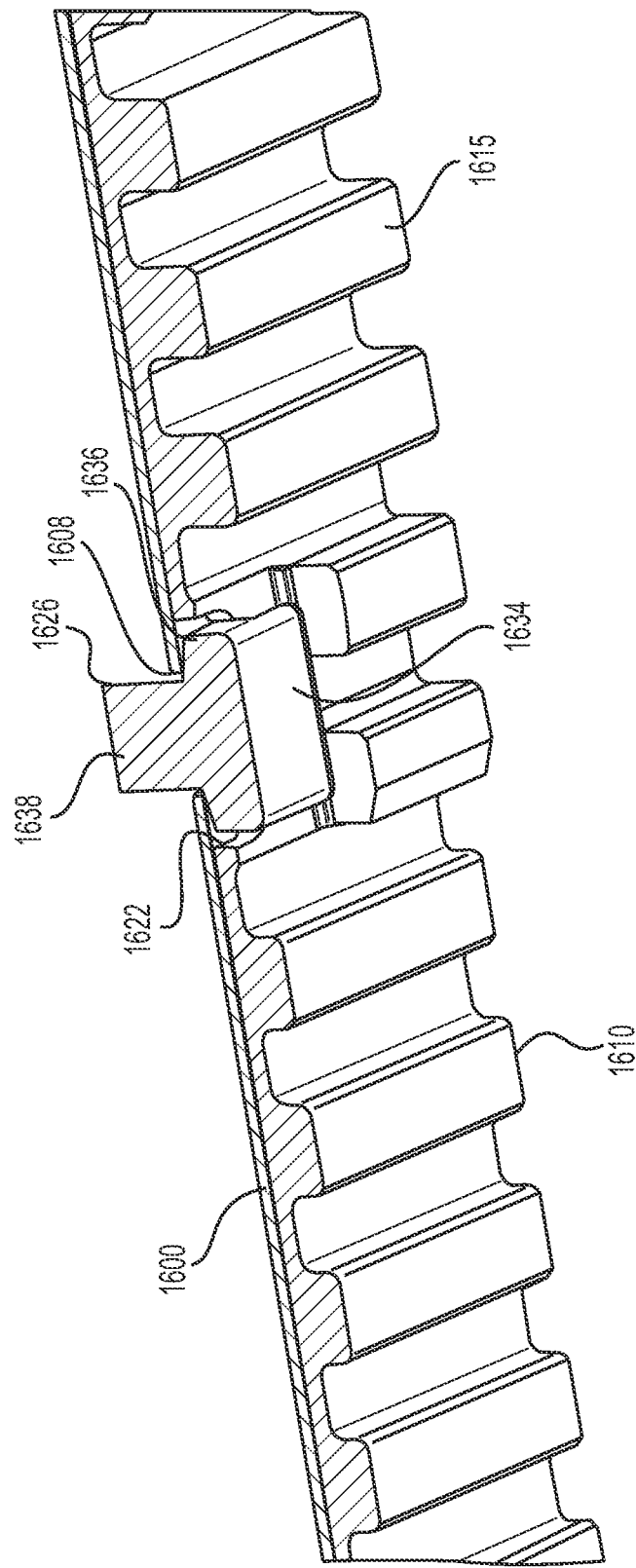
FIG. 12.8

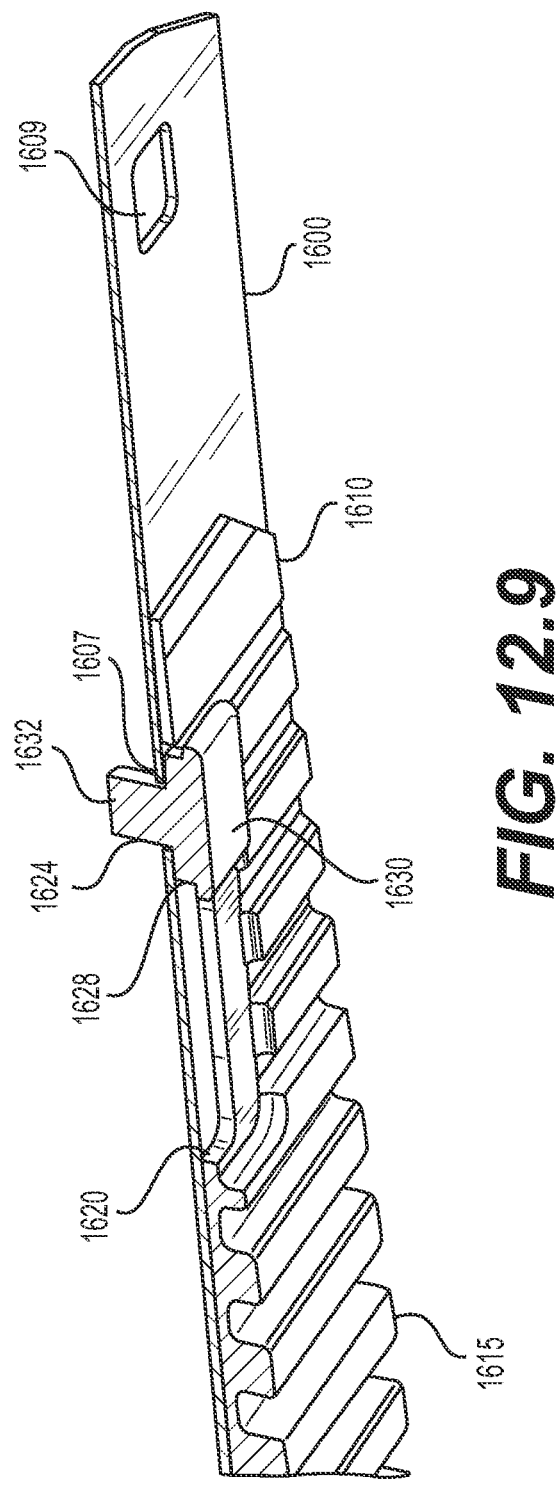
FIG. 12.9

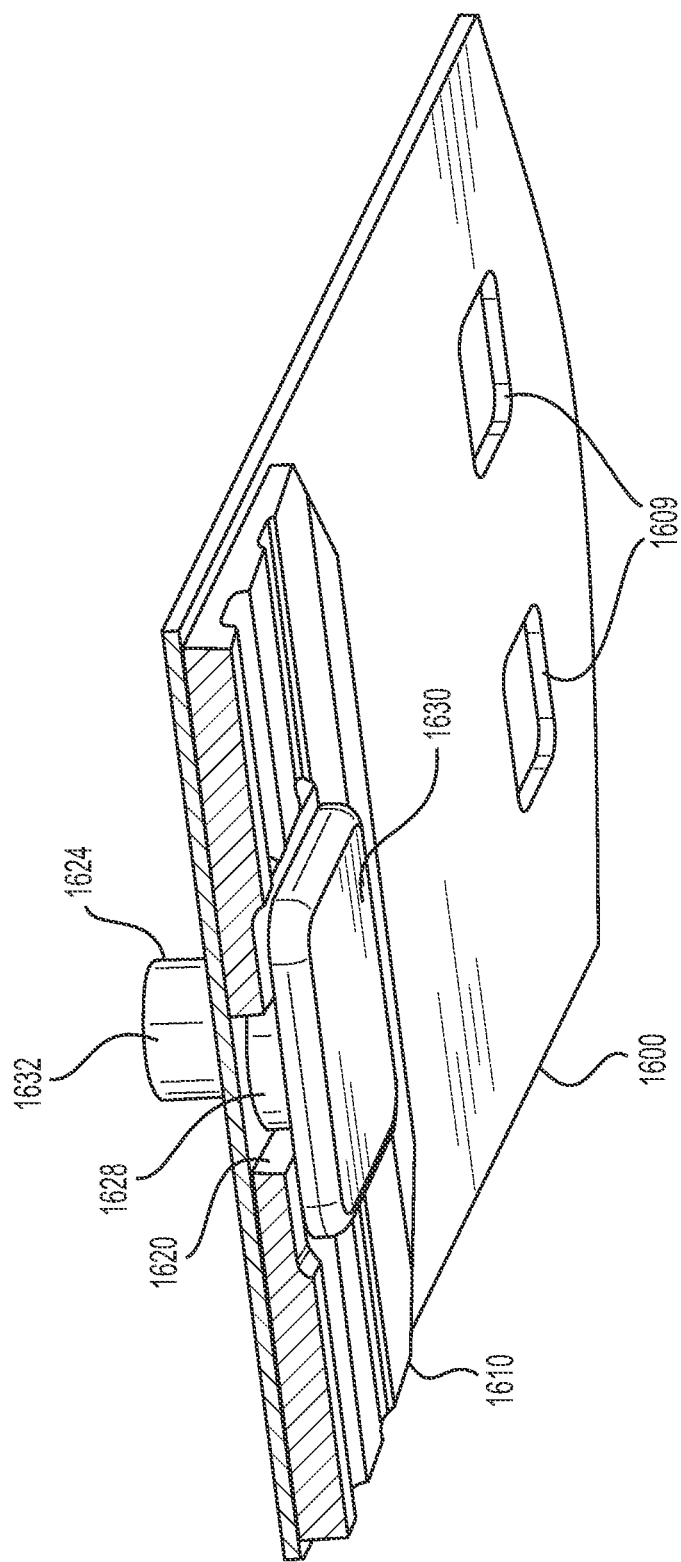
FIG. 12.10

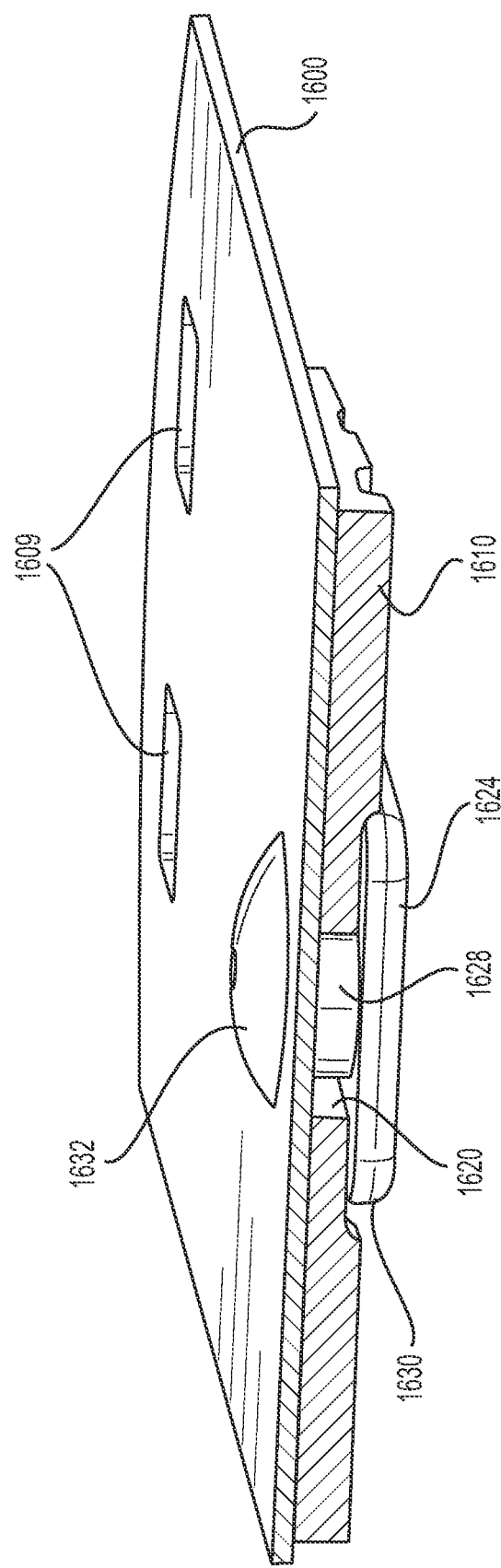
FIG. 12.11

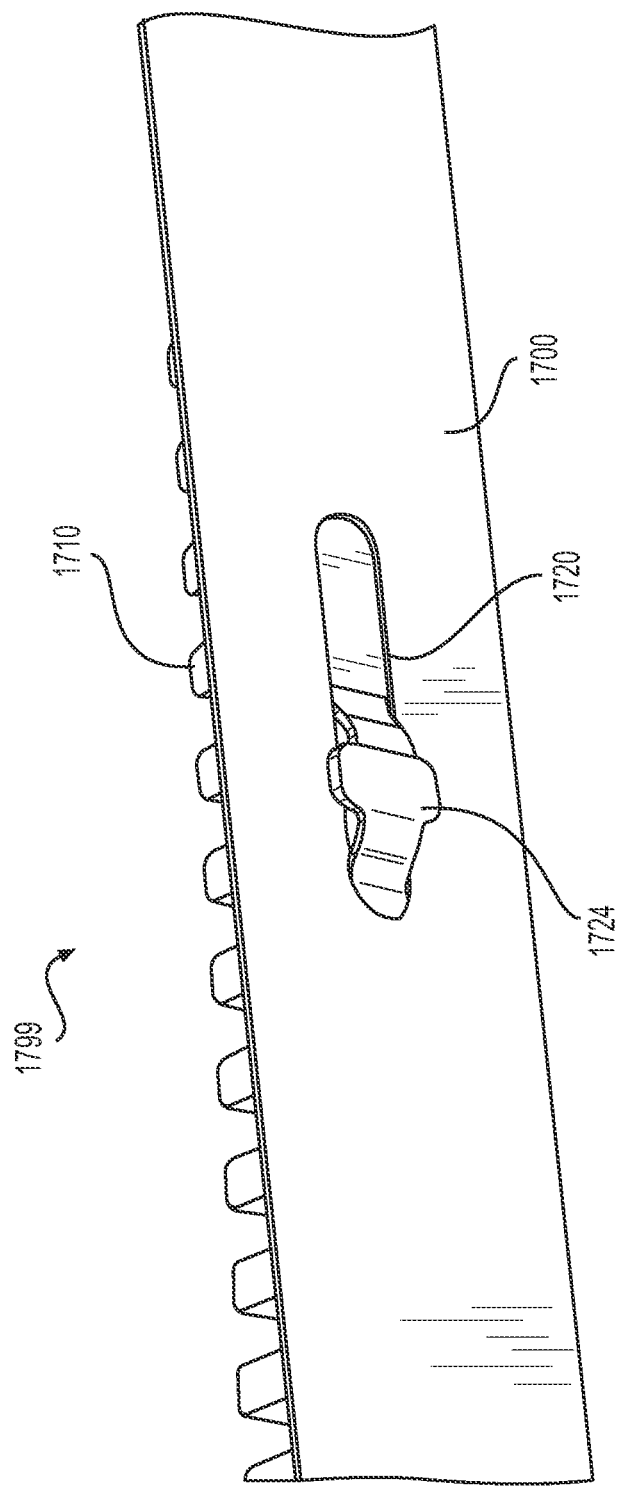
FIG. 13.1

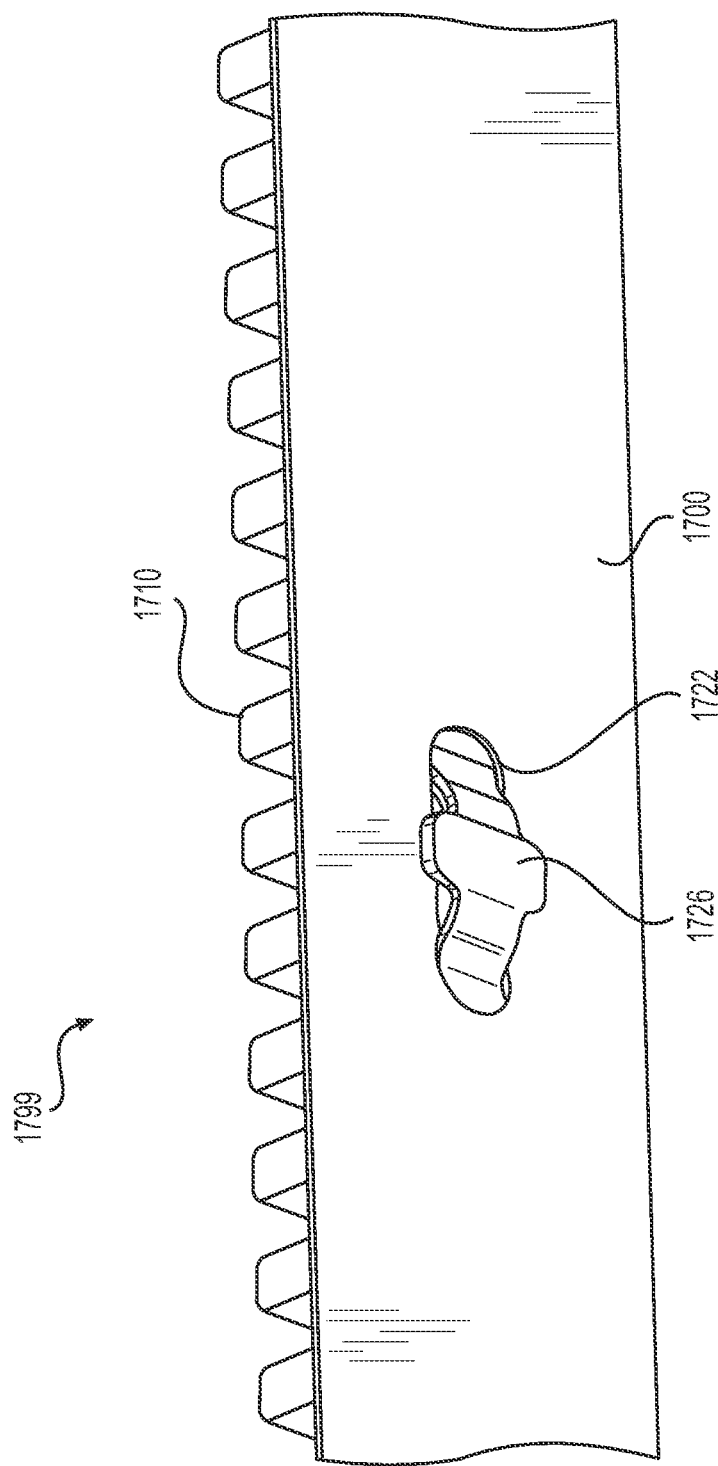
FIG. 13.2

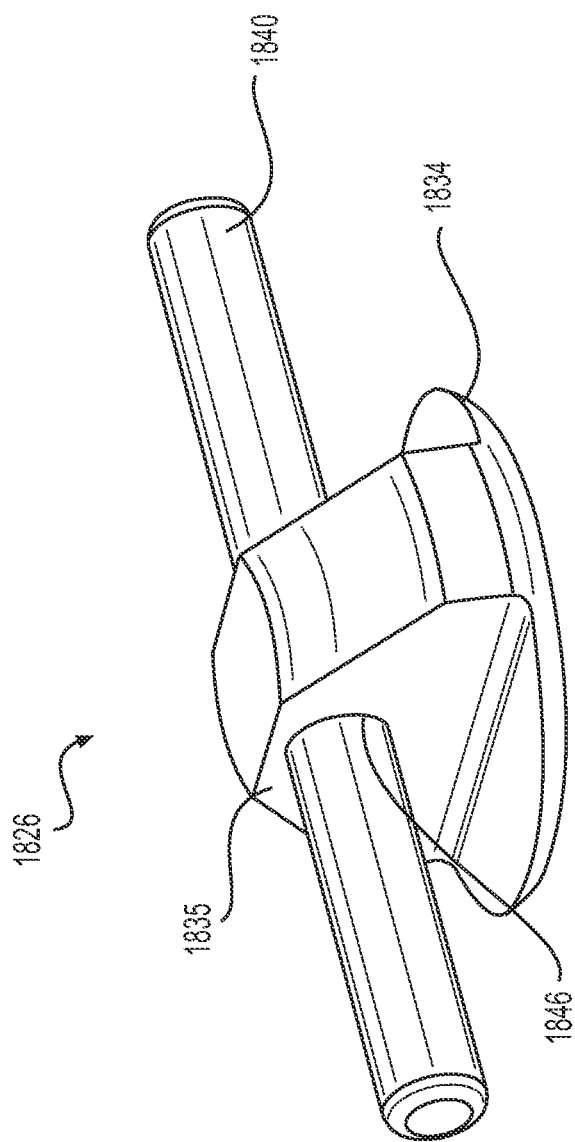
FIG. 14.1

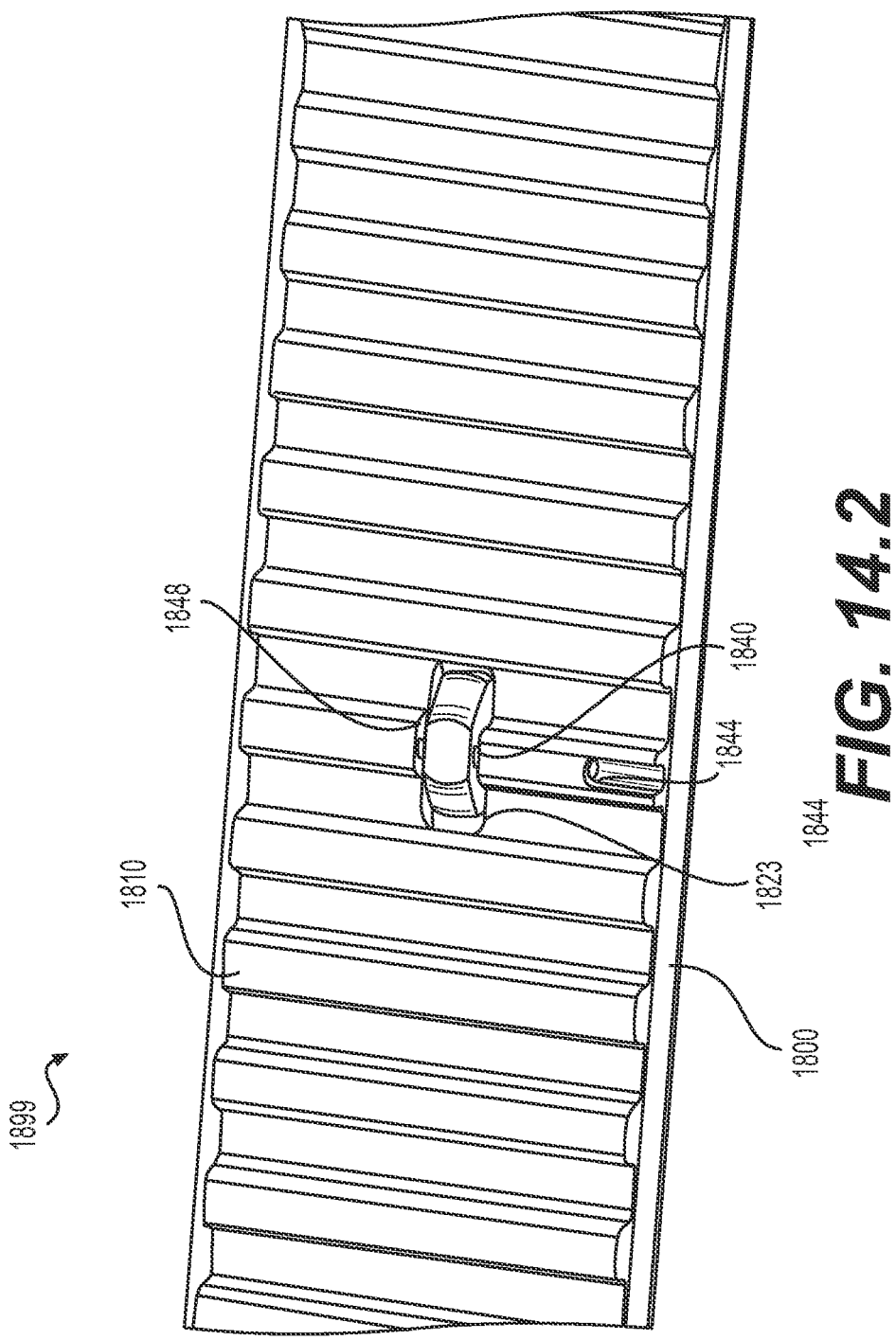
FIG. 14.2

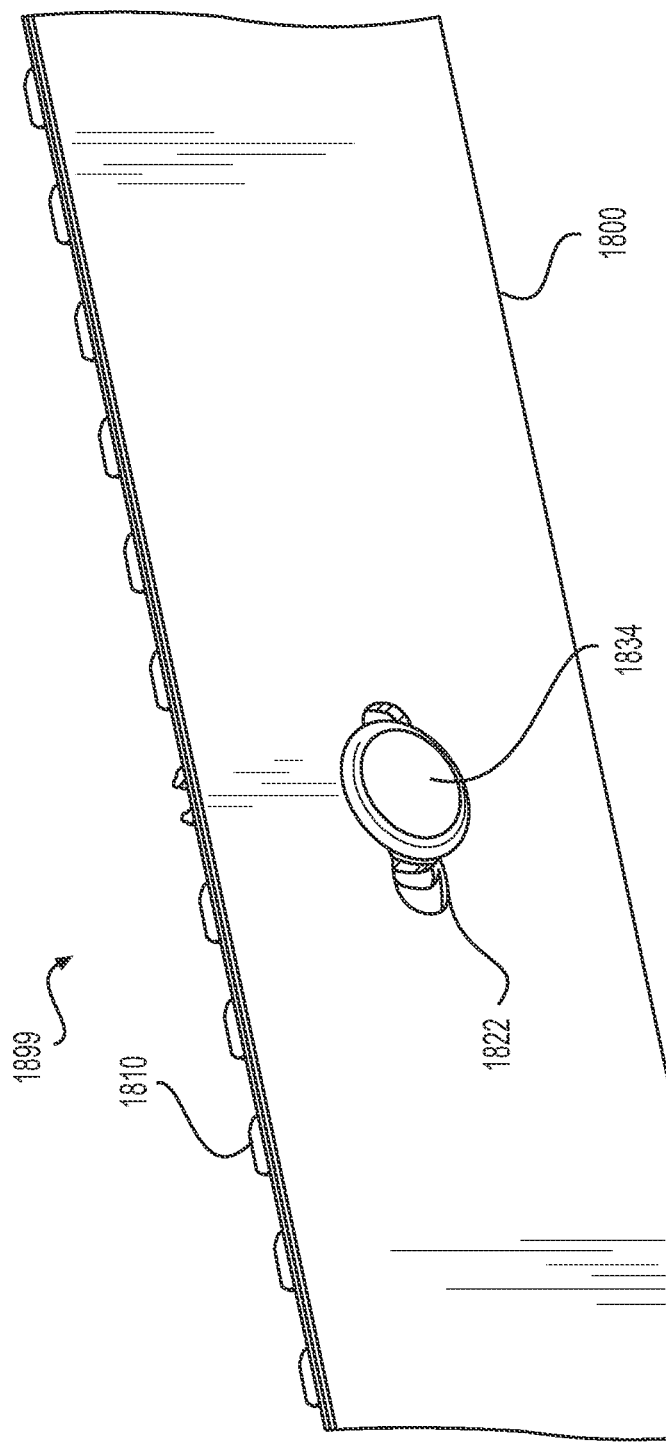
FIG. 14.3

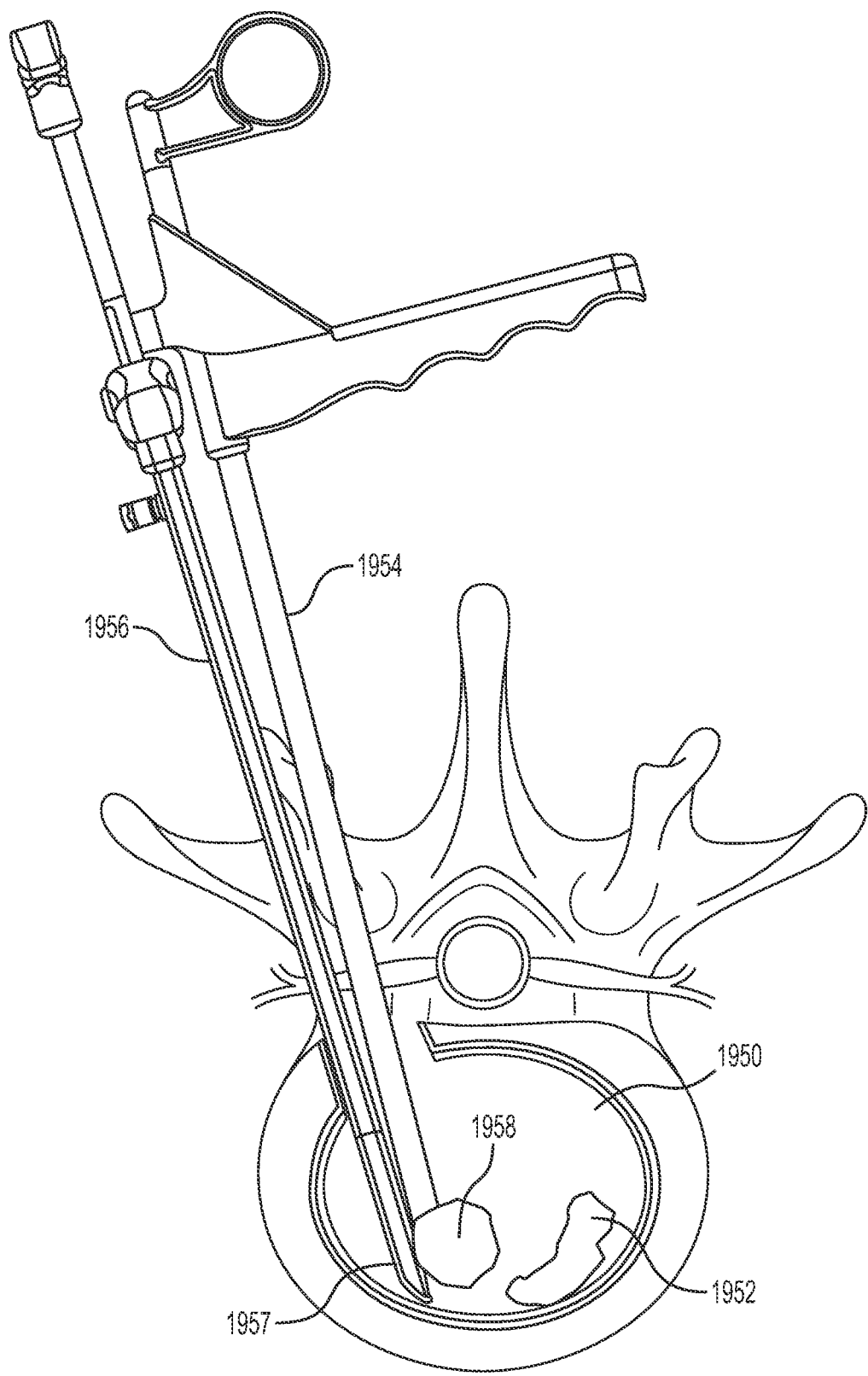
FIG. 15.1

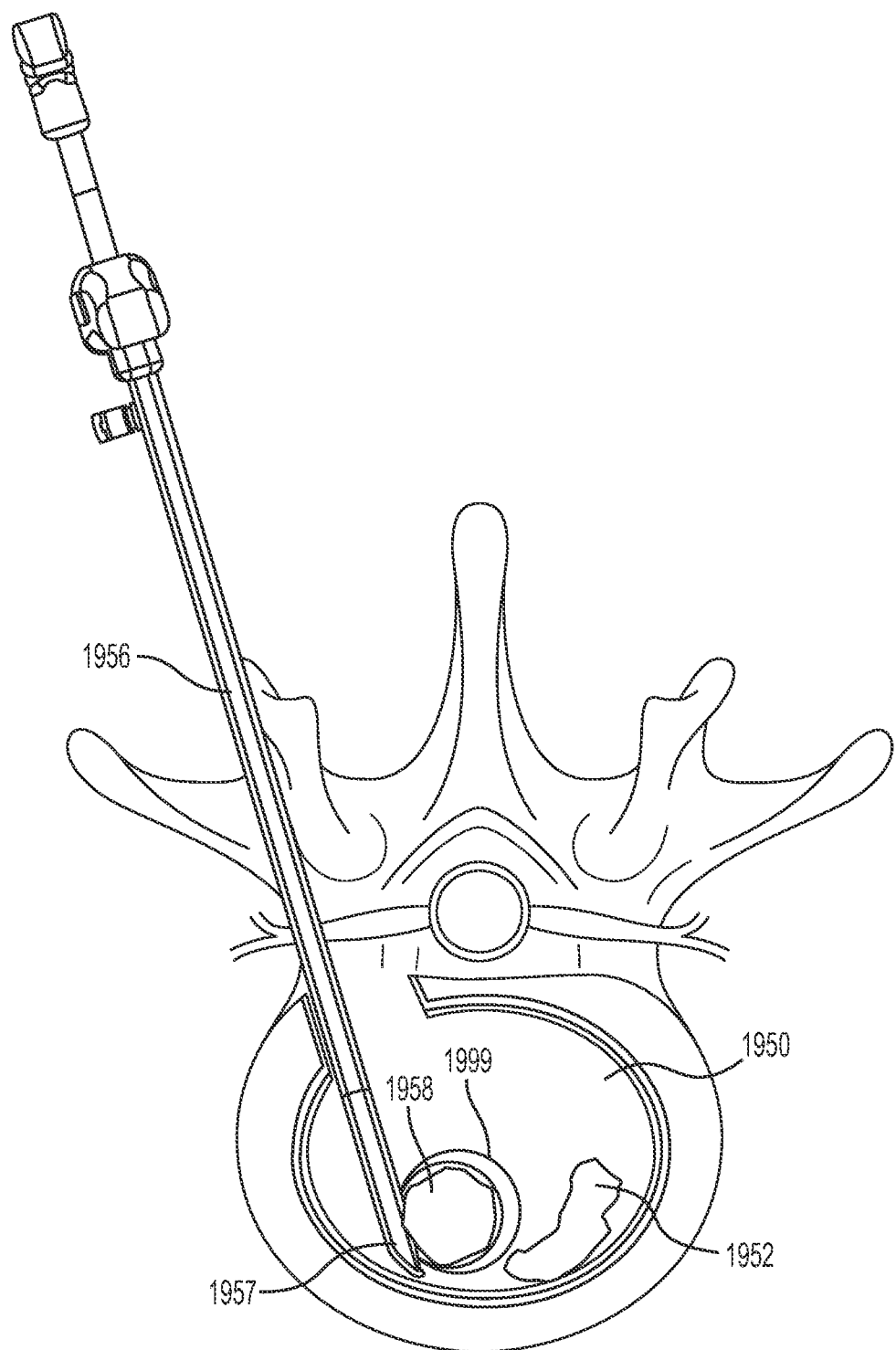
FIG. 15.2

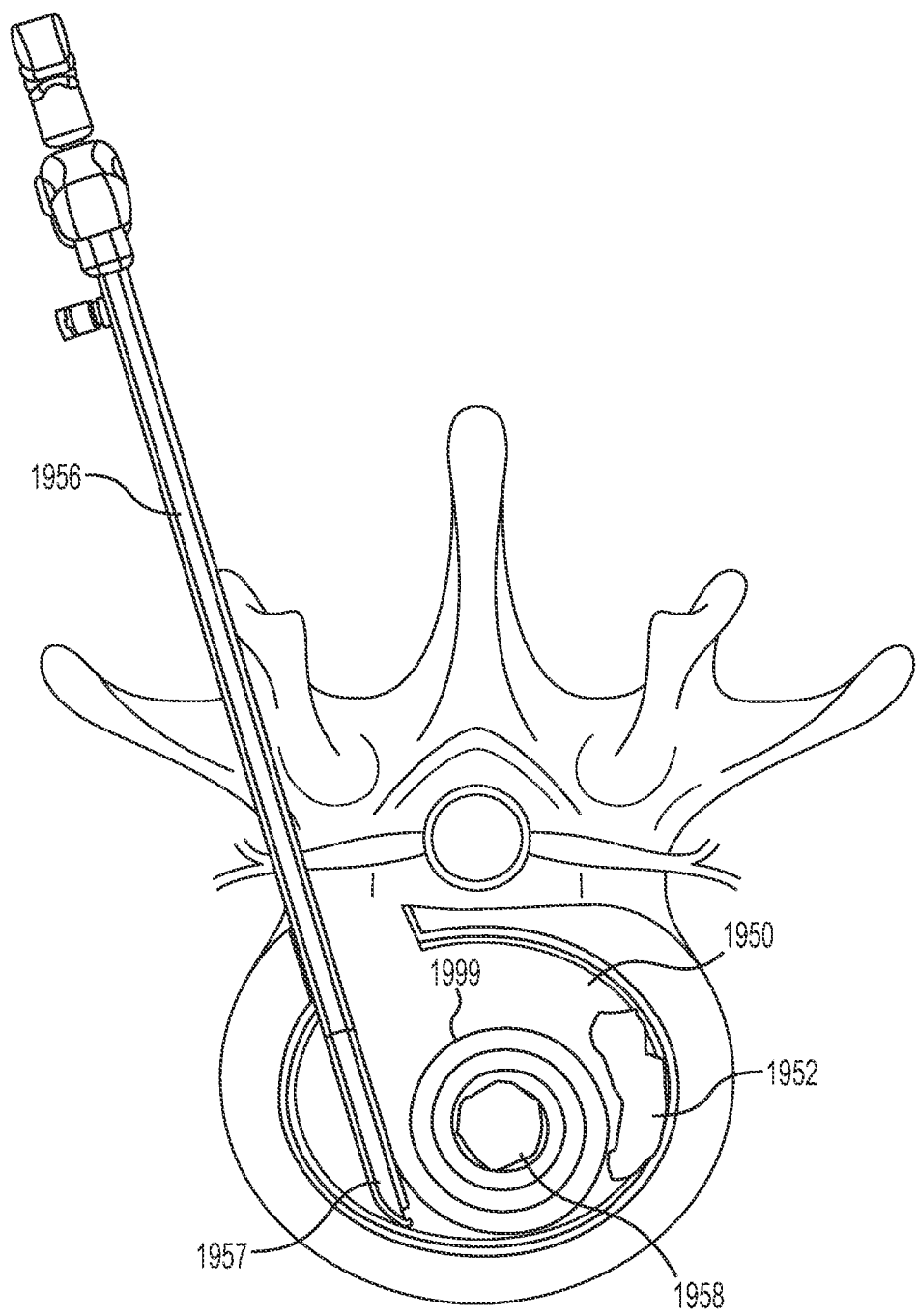
FIG. 15.3

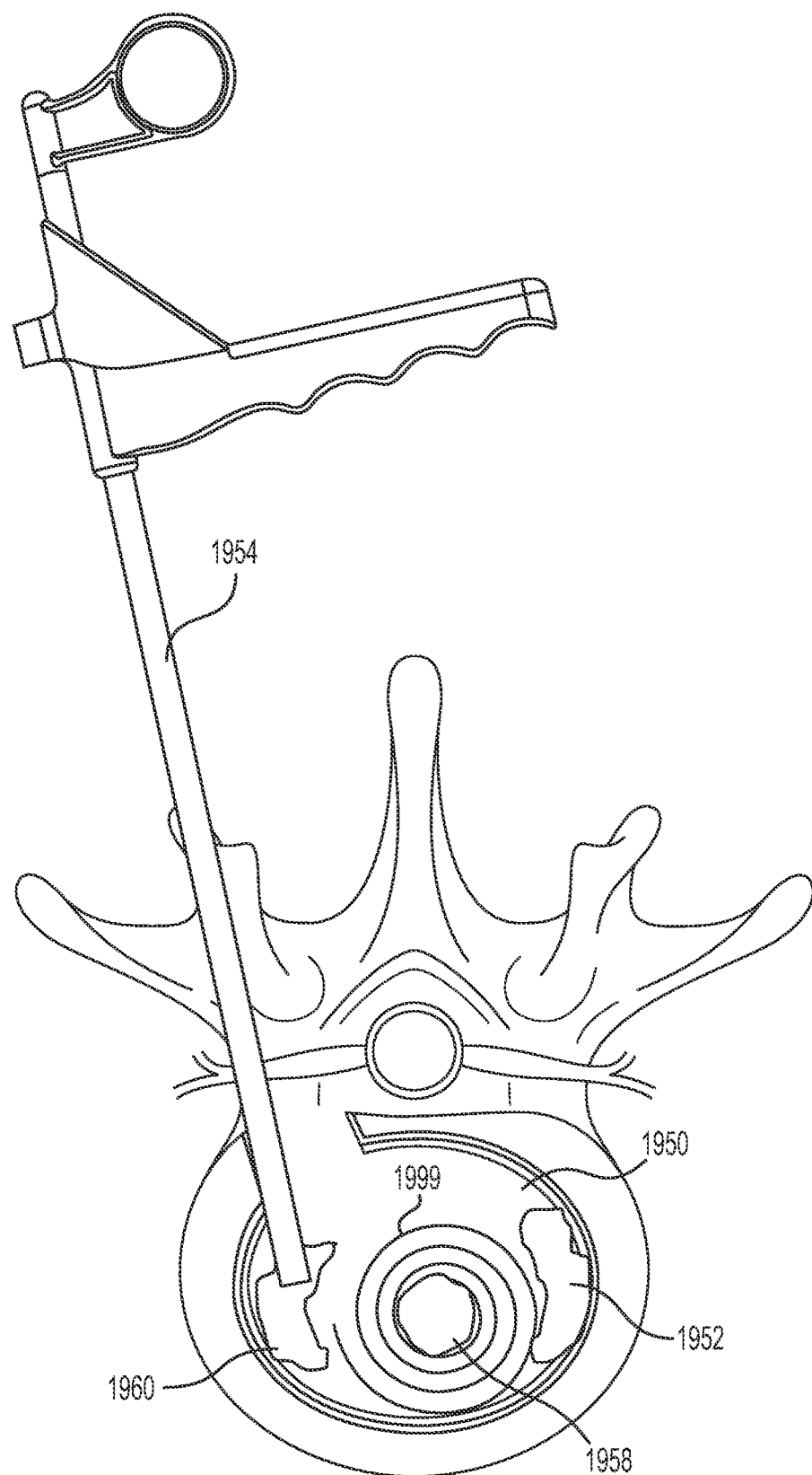
FIG. 15.4

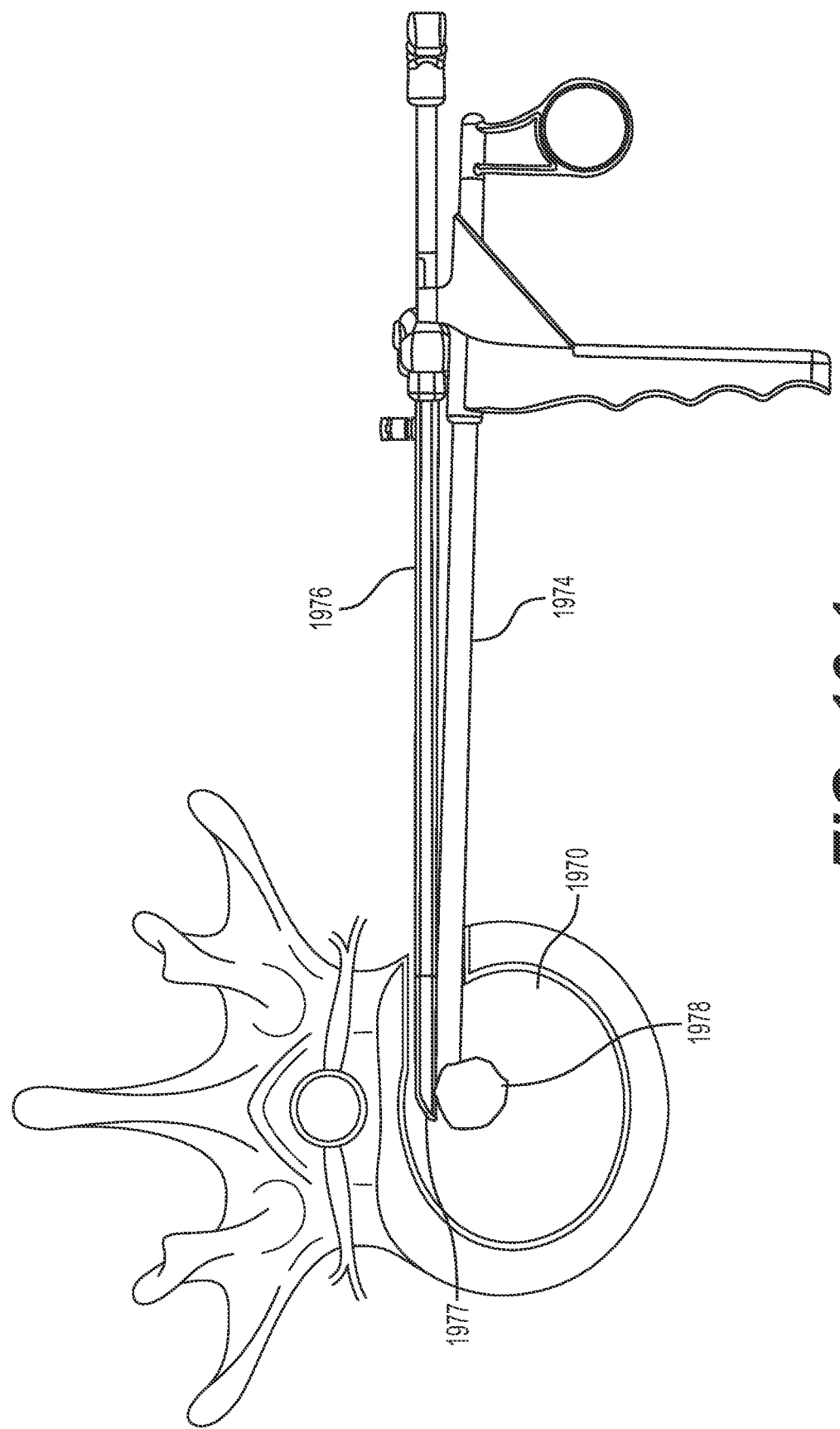
FIG. 16.1

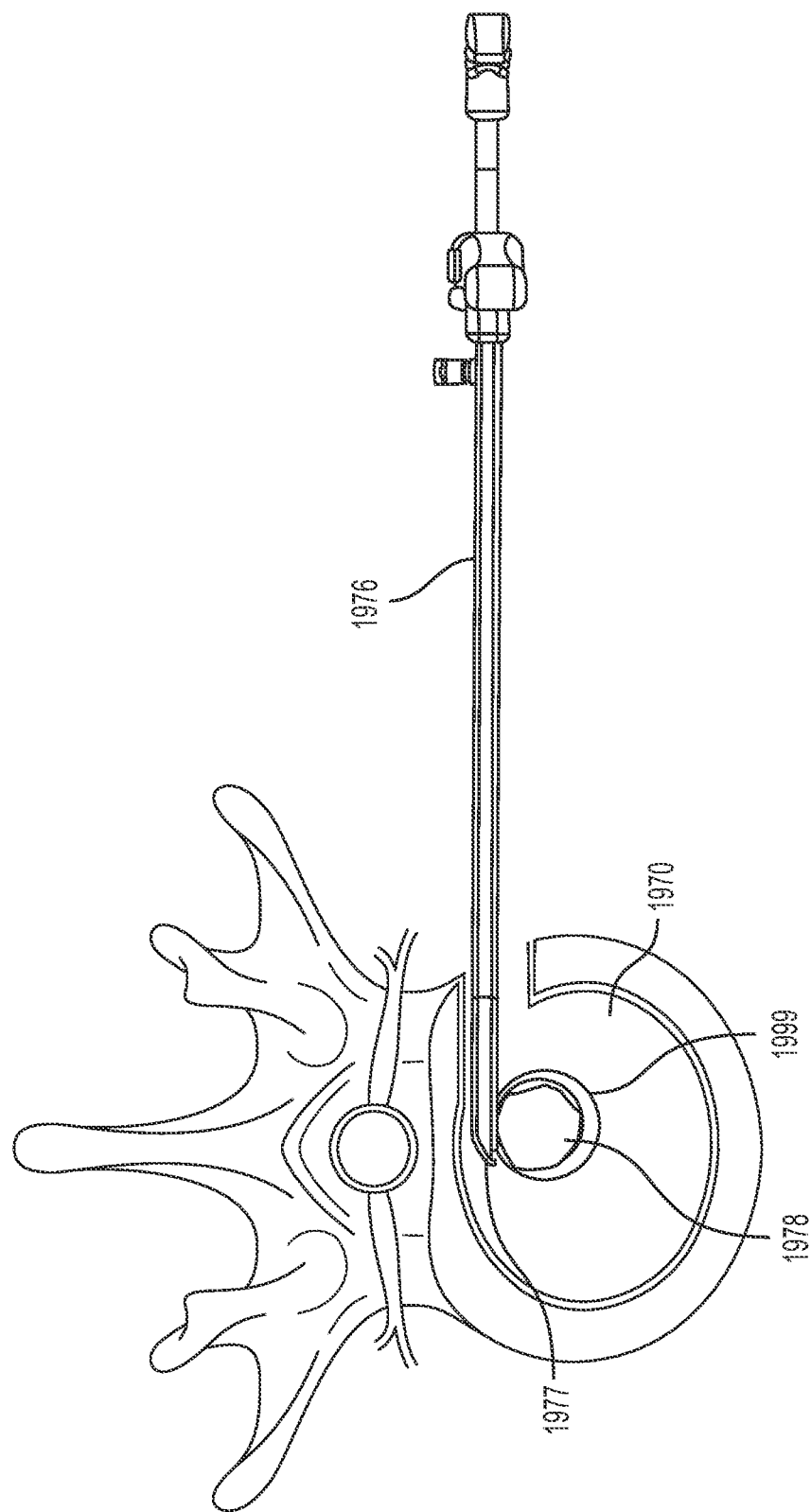
FIG. 16.2

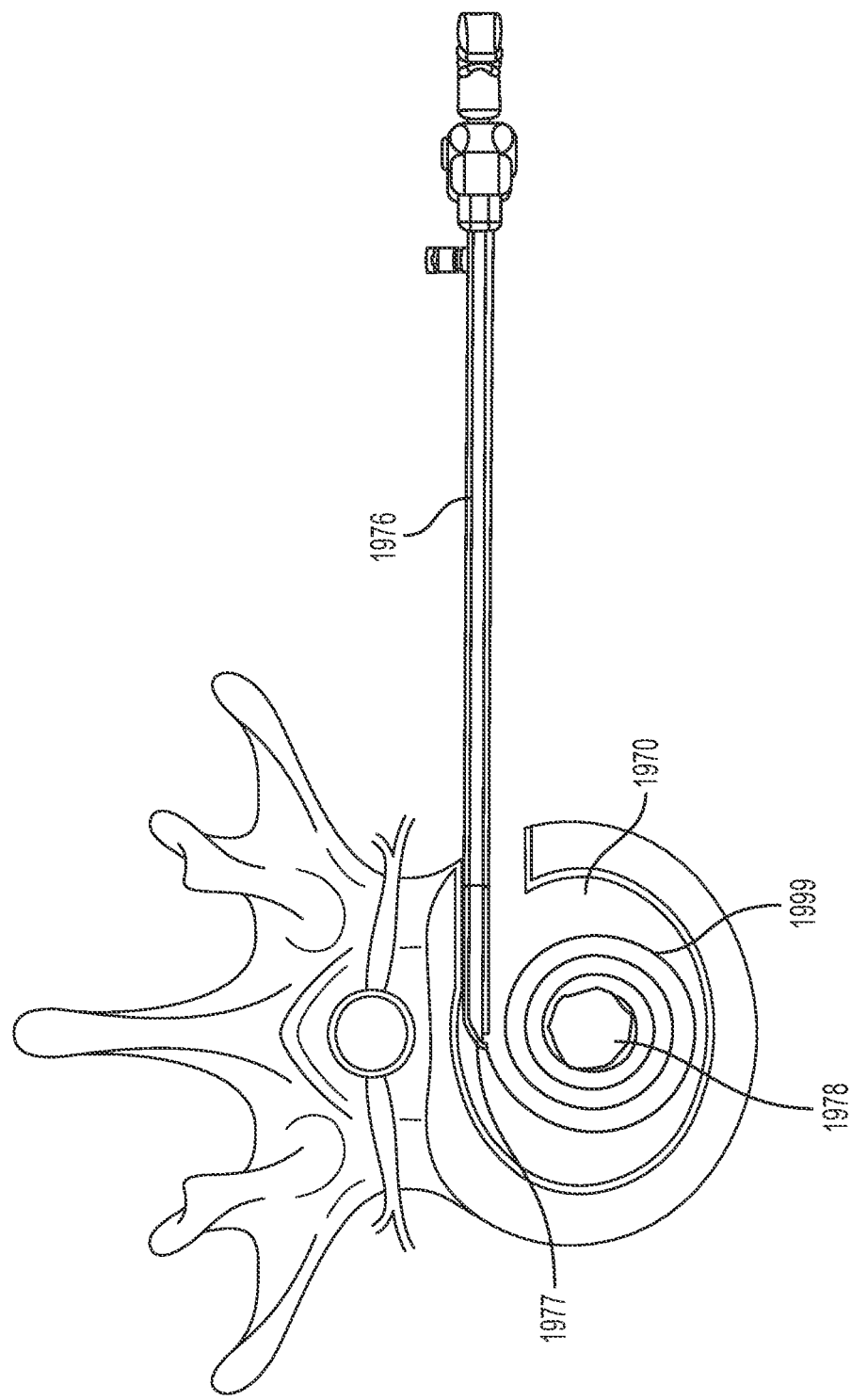
FIG. 16.3

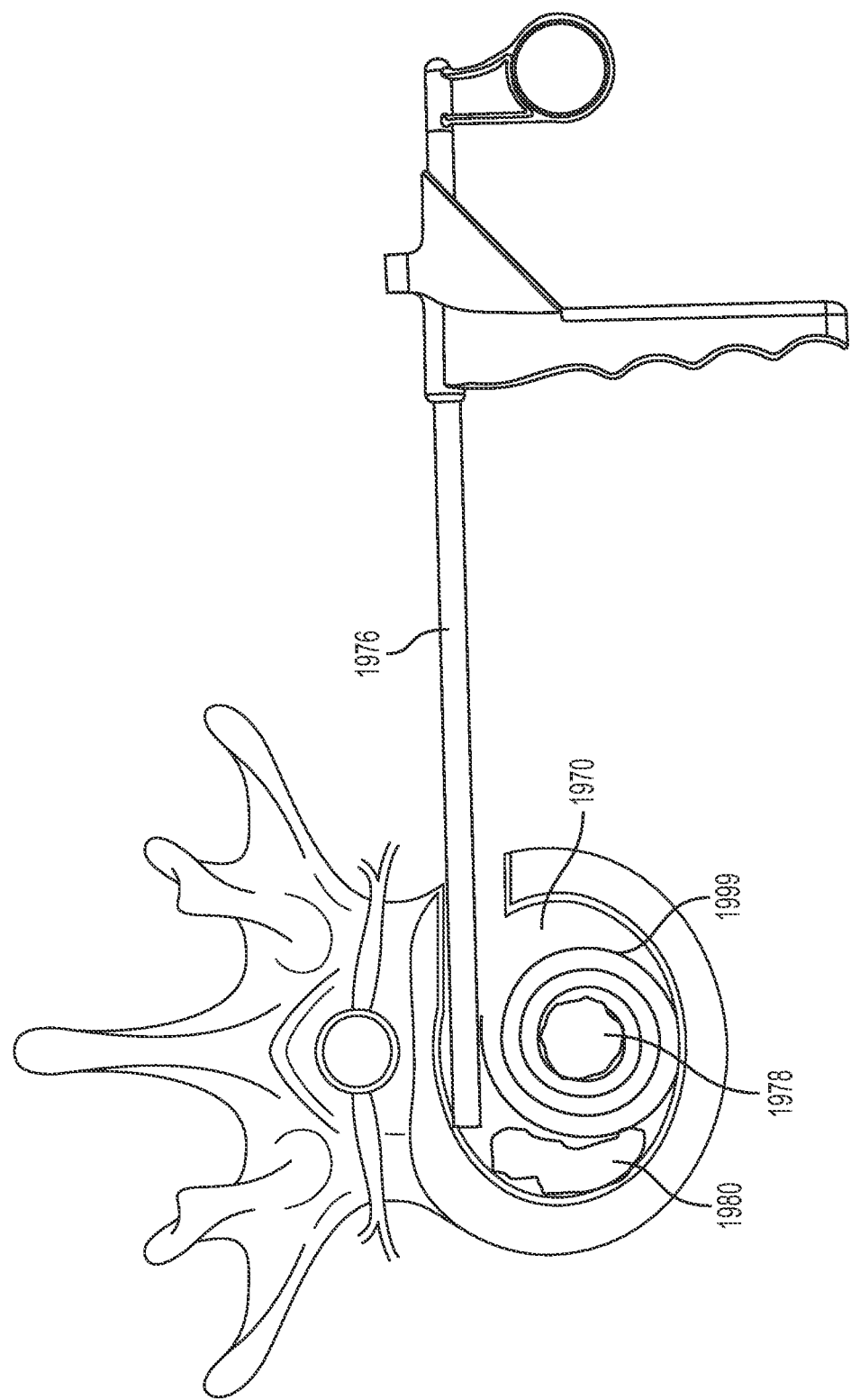
FIG. 16.4

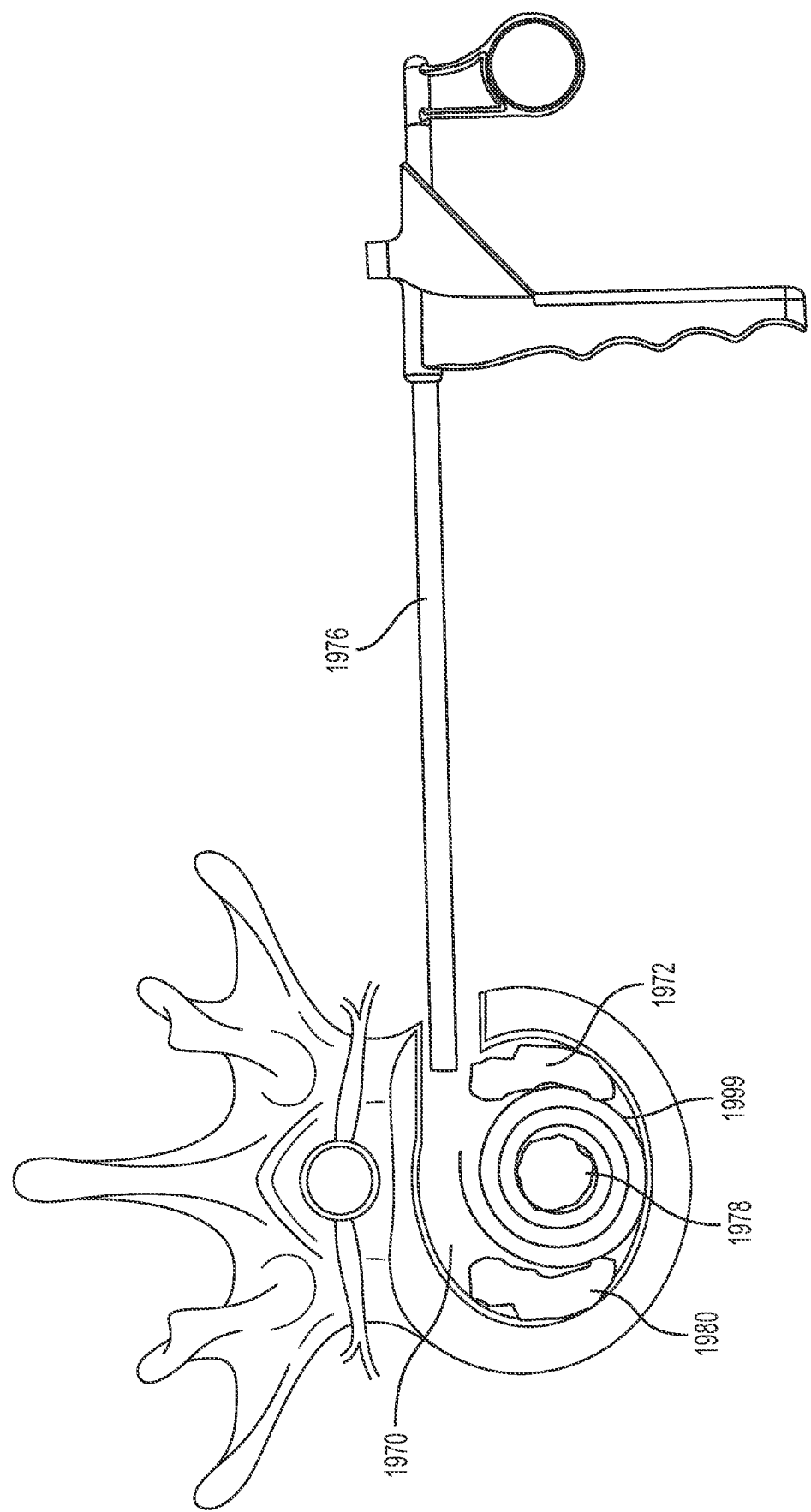
FIG. 16.5

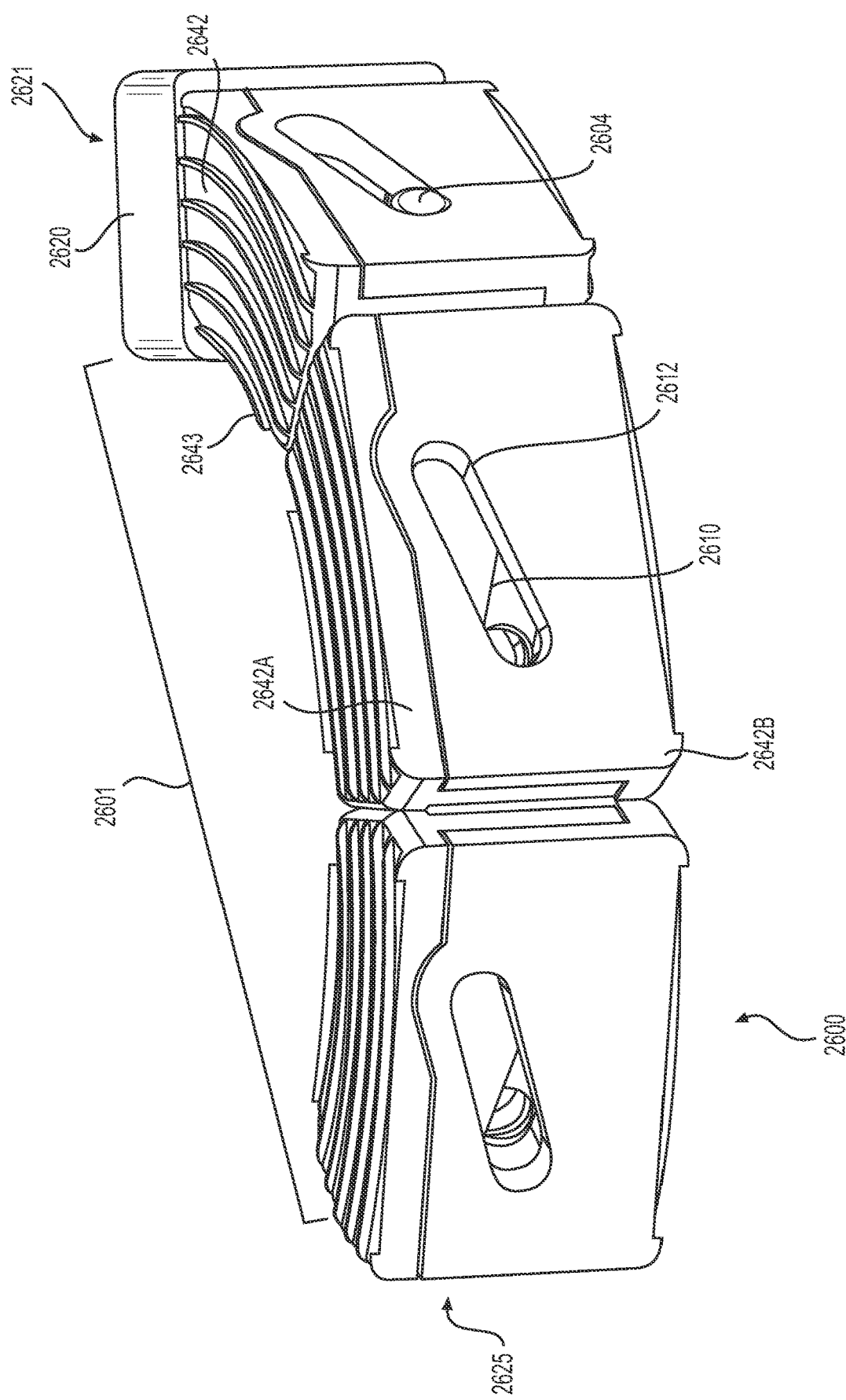
FIG. 17.1

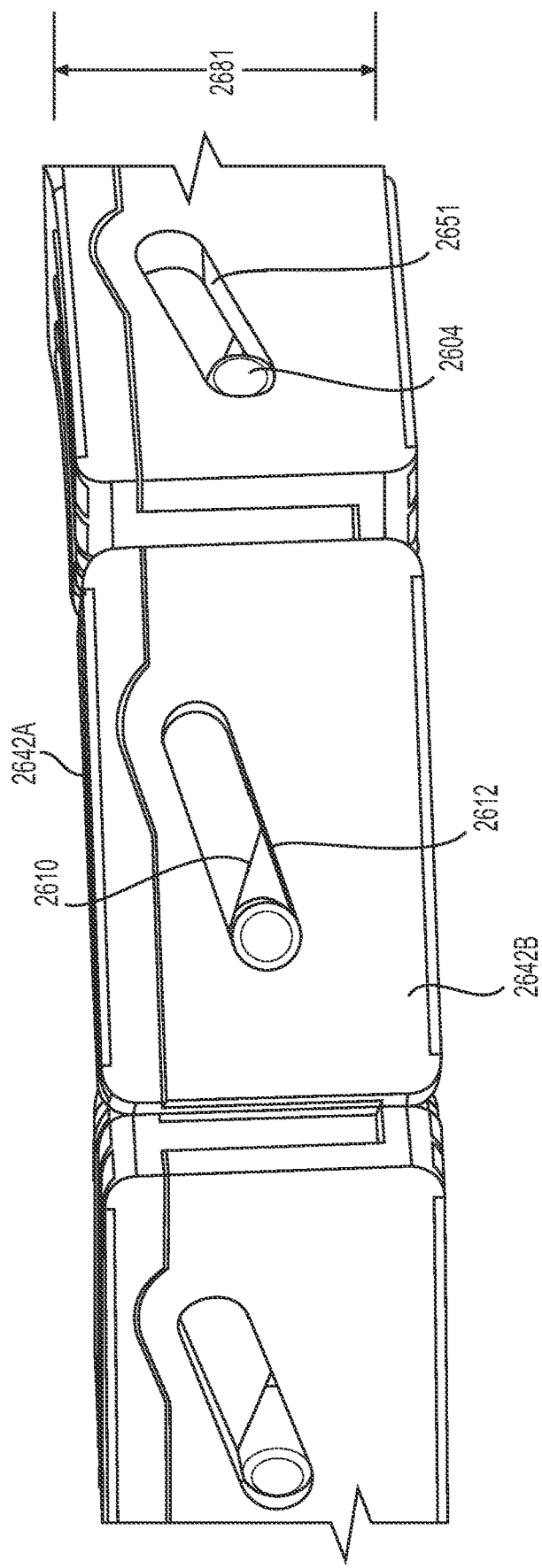
FIG. 17.2

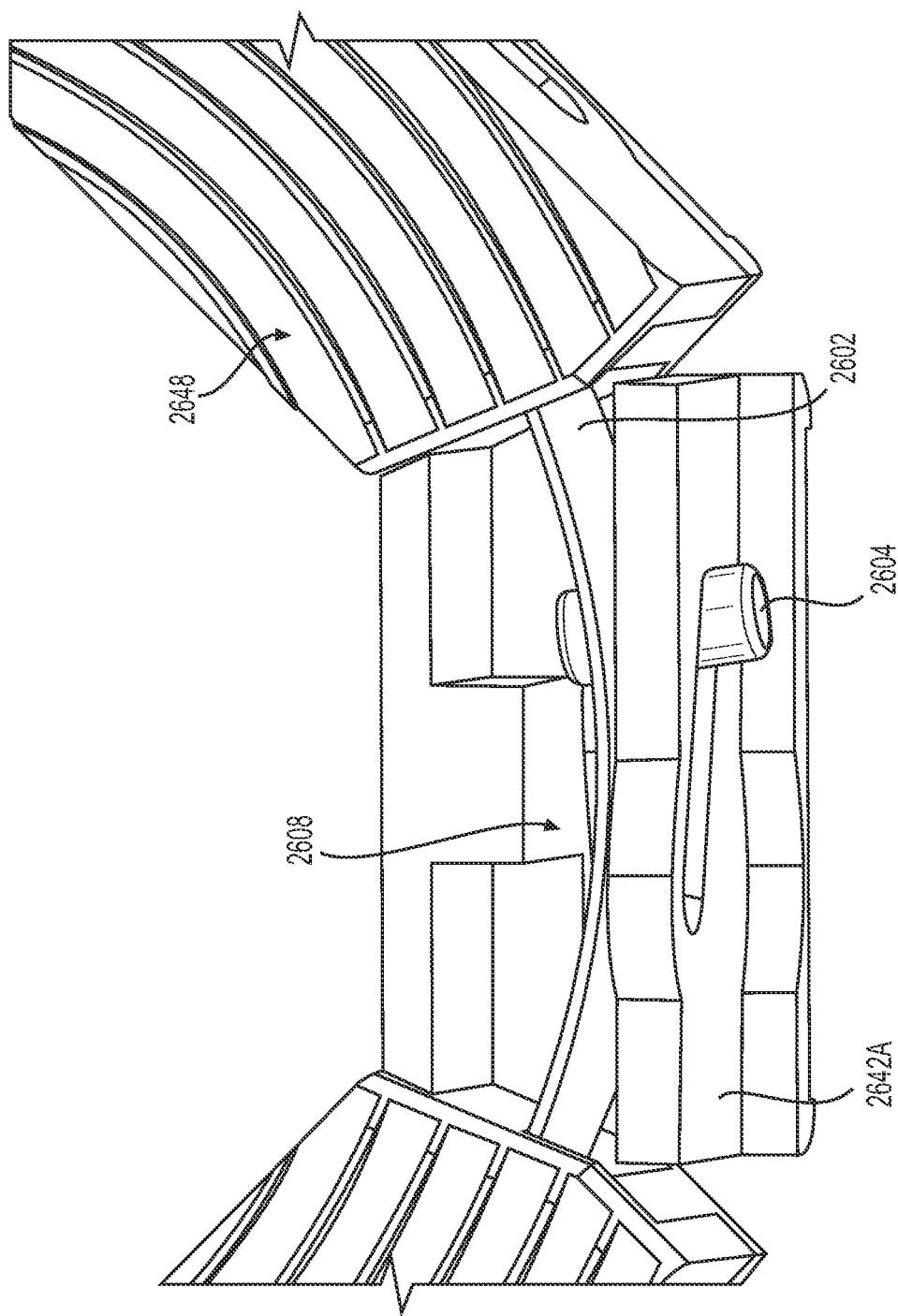
FIG. 17.3

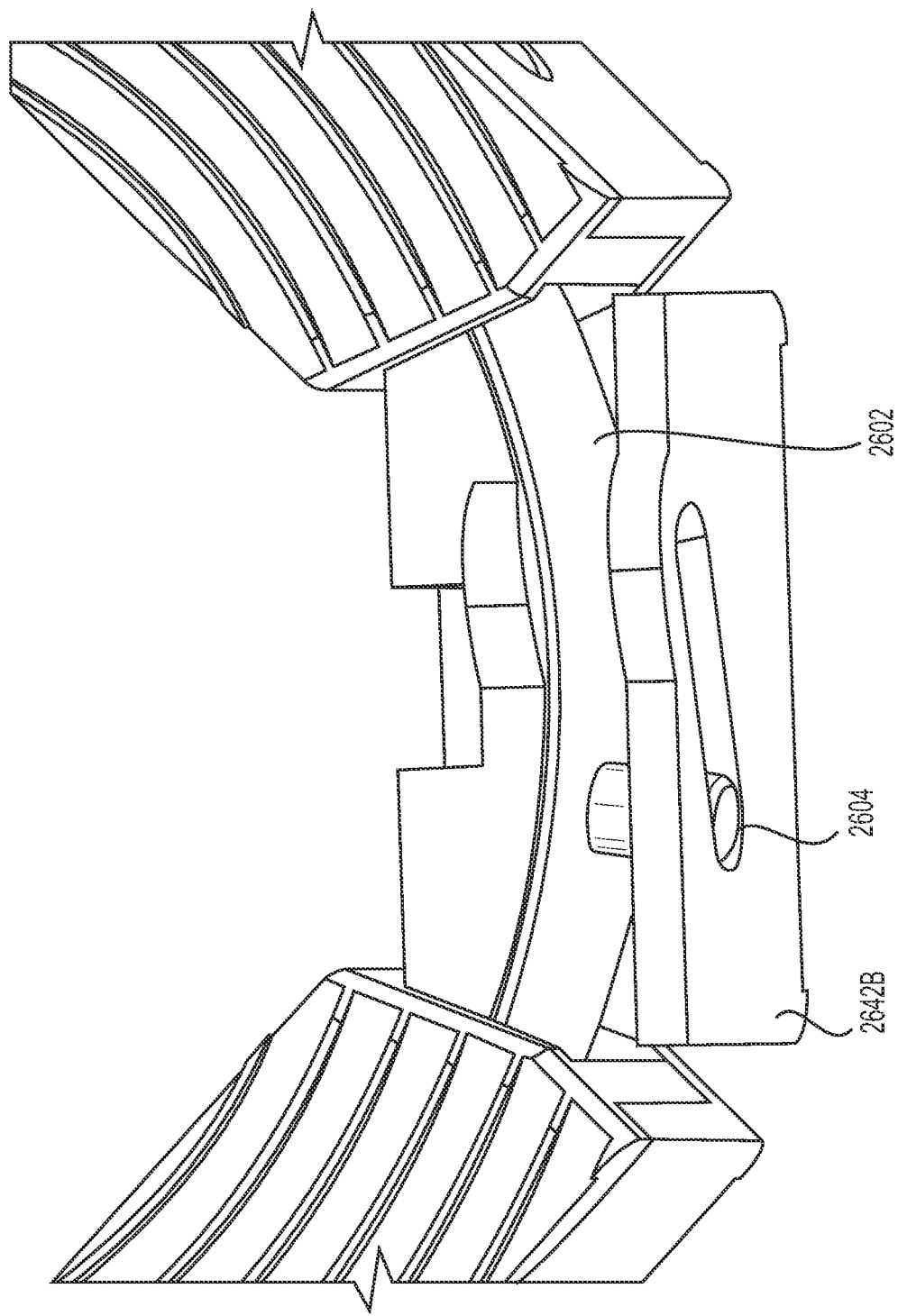
FIG. 17.4

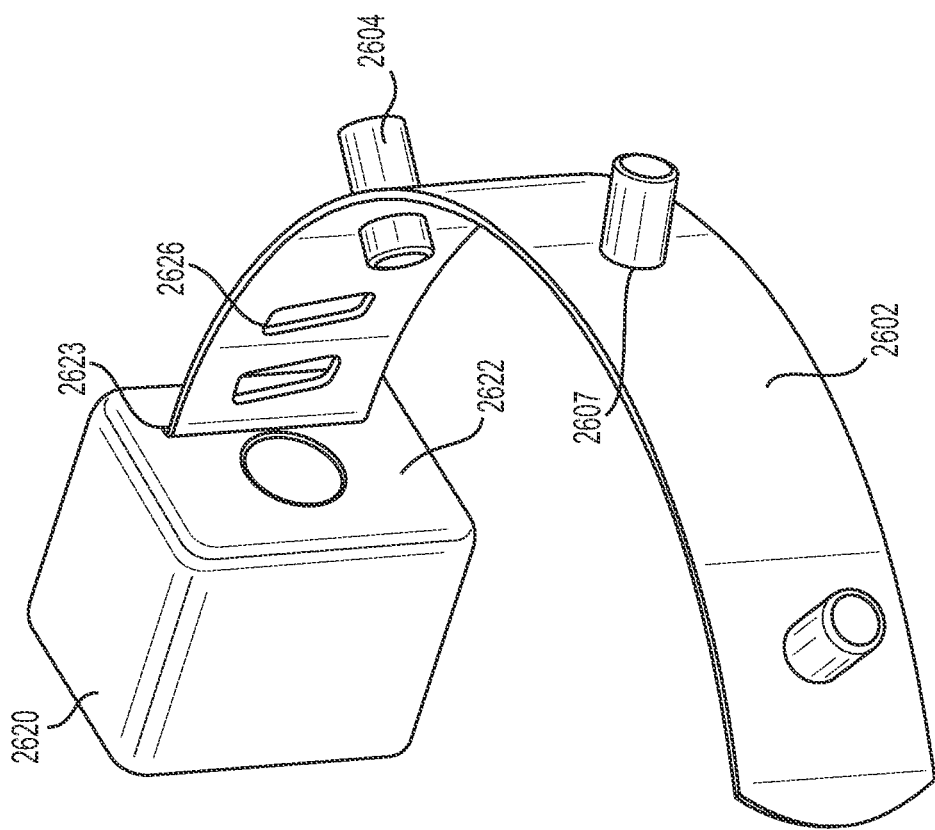
FIG. 17.5

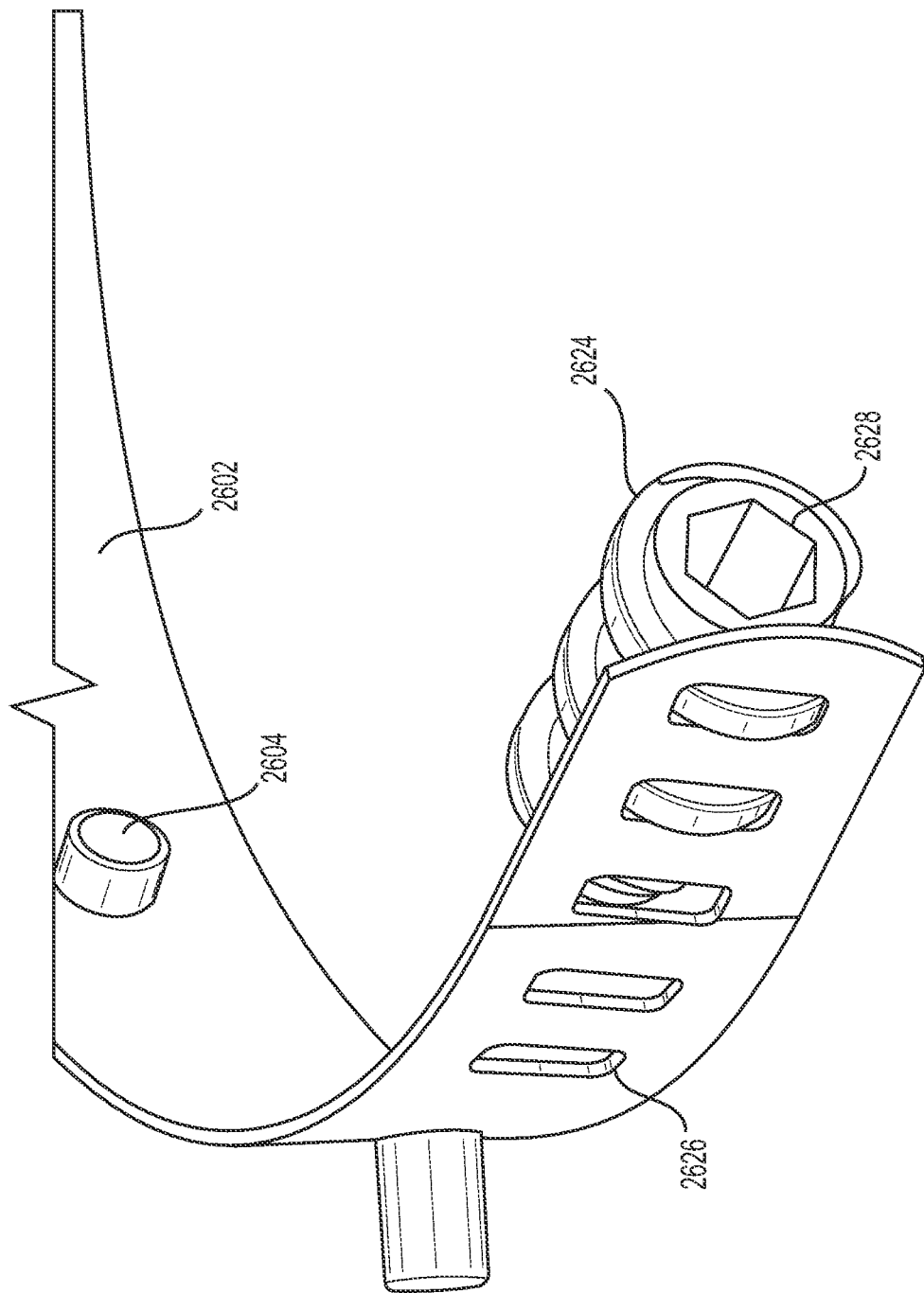
FIG. 17.6

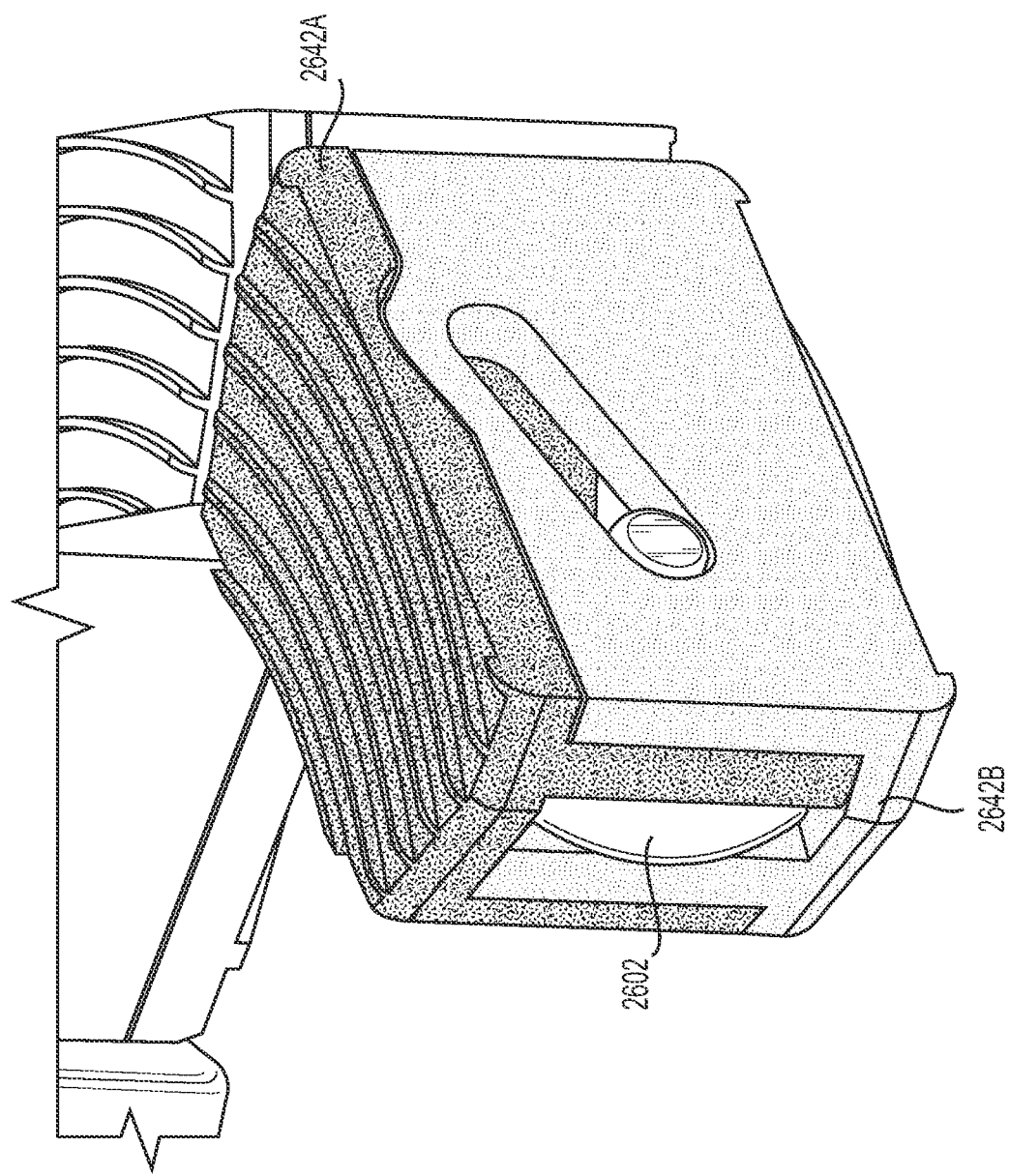
FIG. 17.7

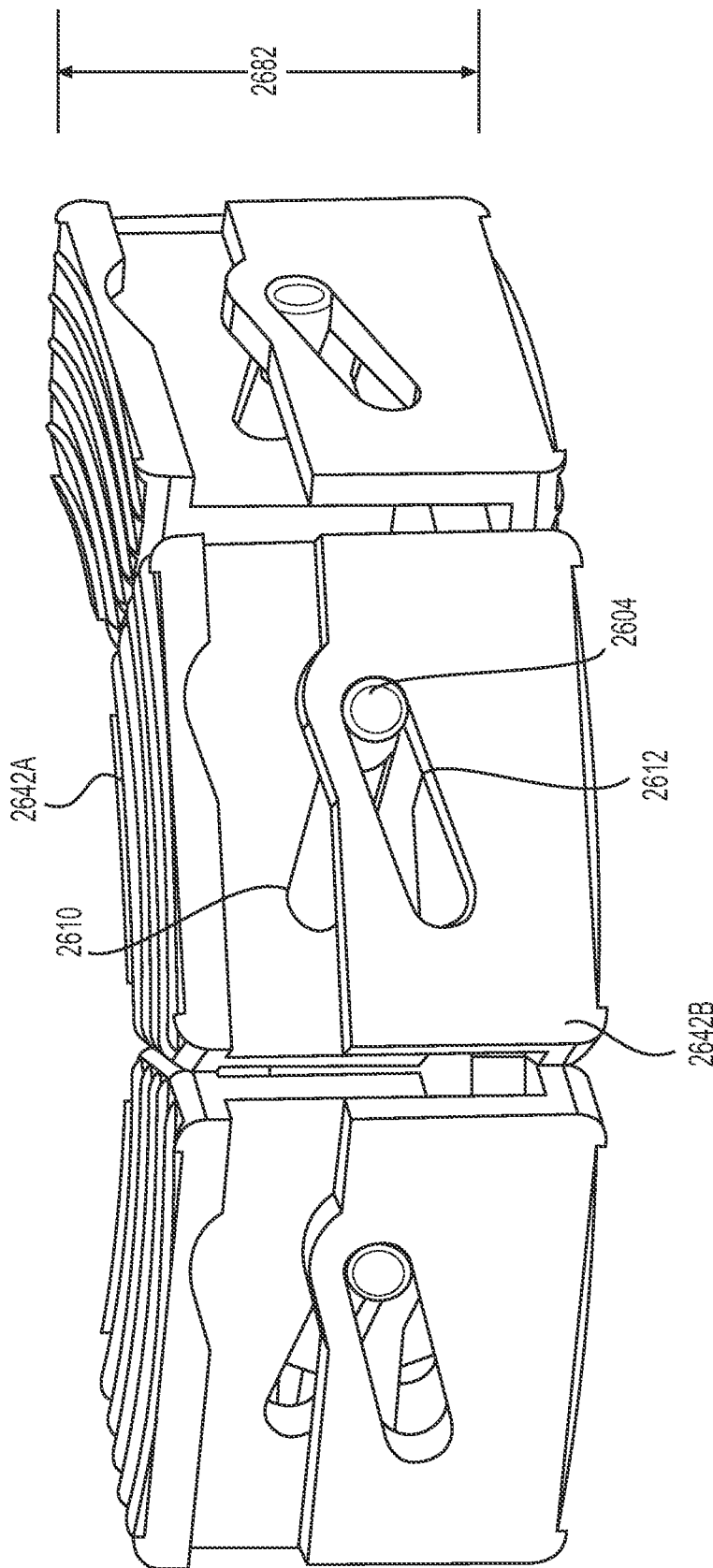
FIG. 17.8

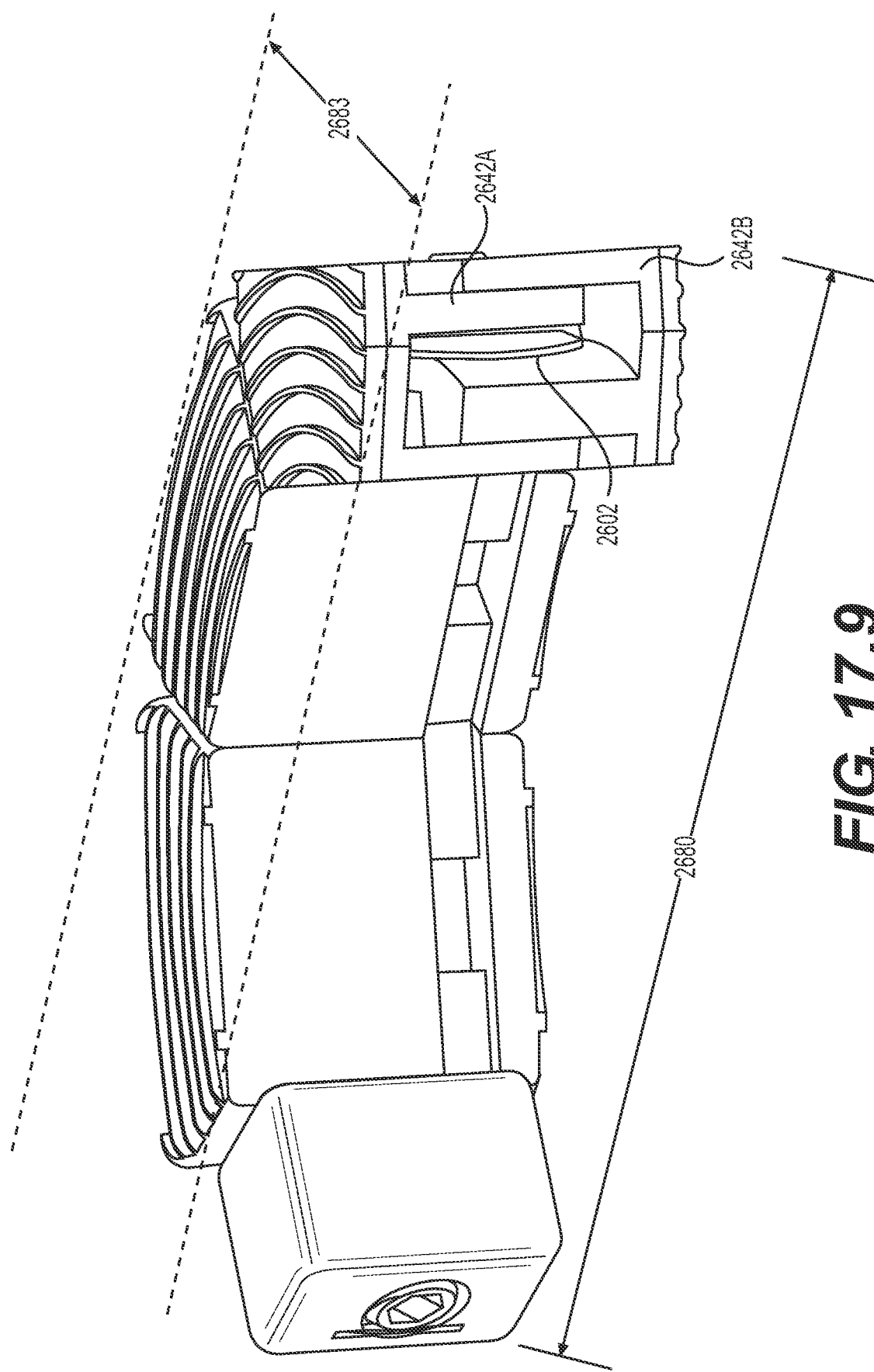
FIG. 17.9

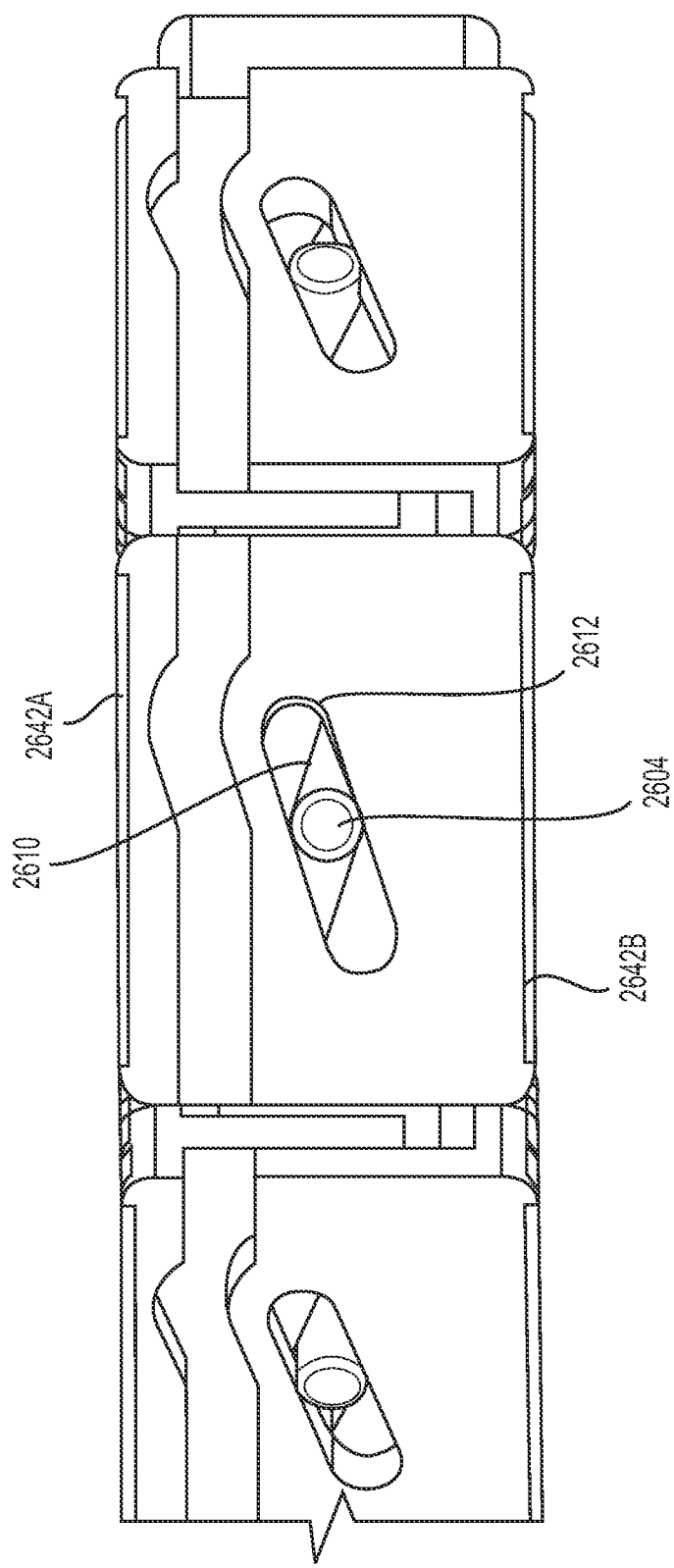
FIG. 17.10

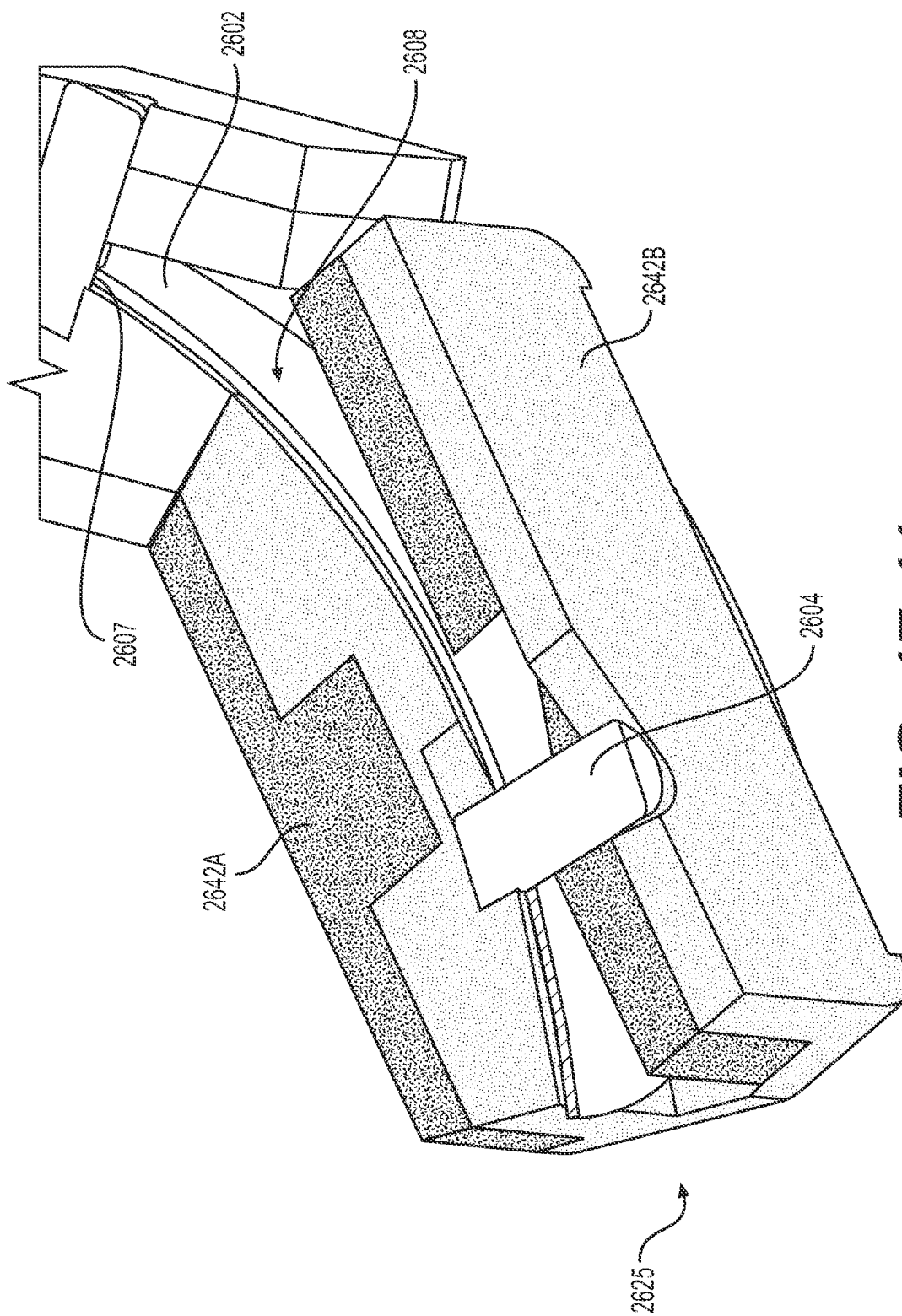
FIG. 17.11

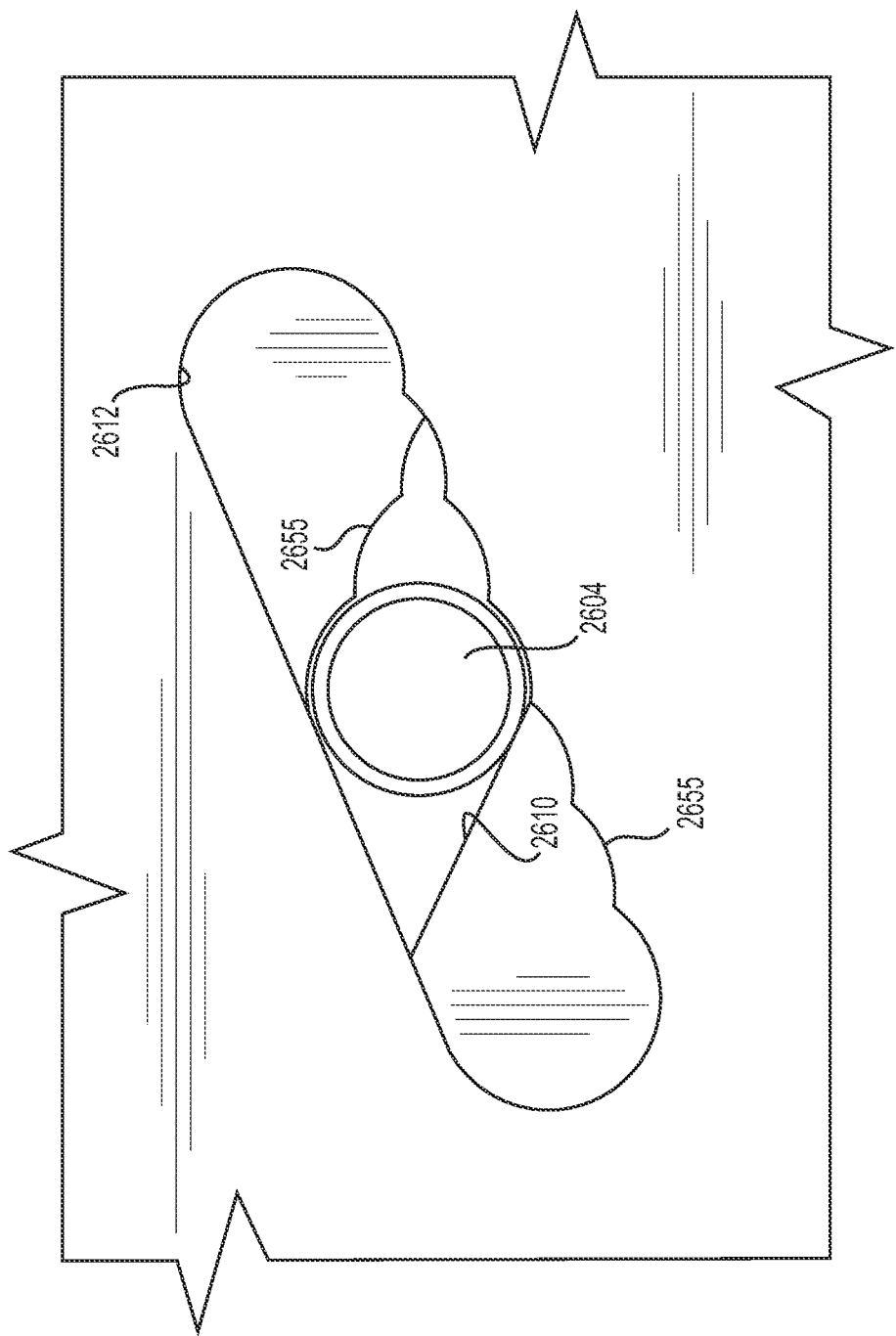
FIG. 17.12

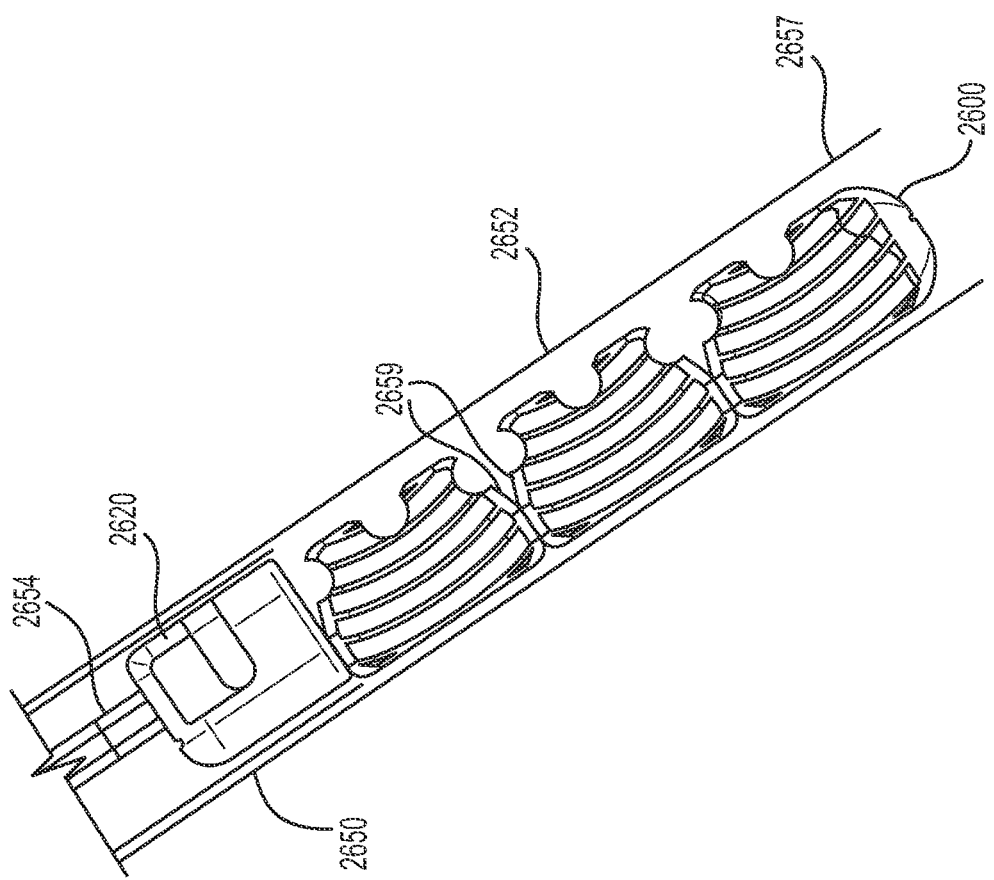
FIG. 18.1

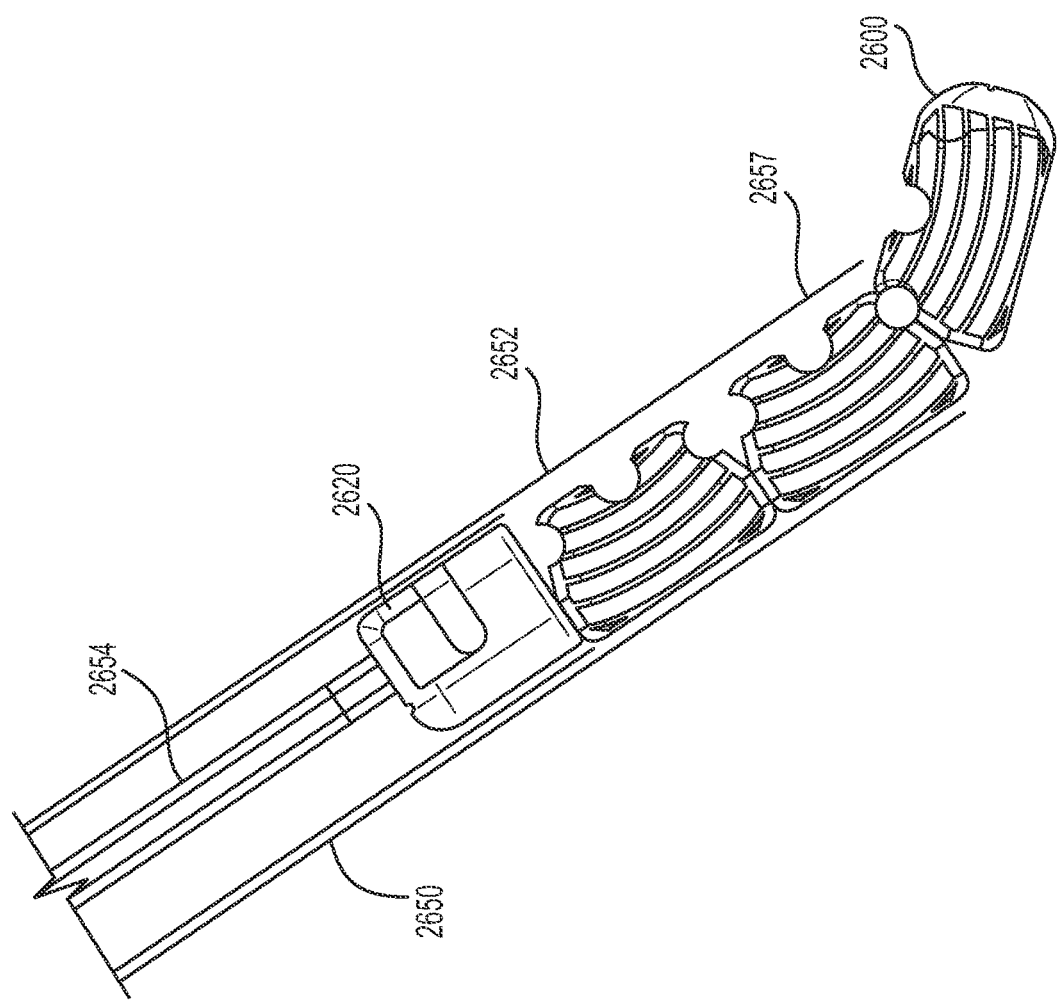
FIG. 18.2

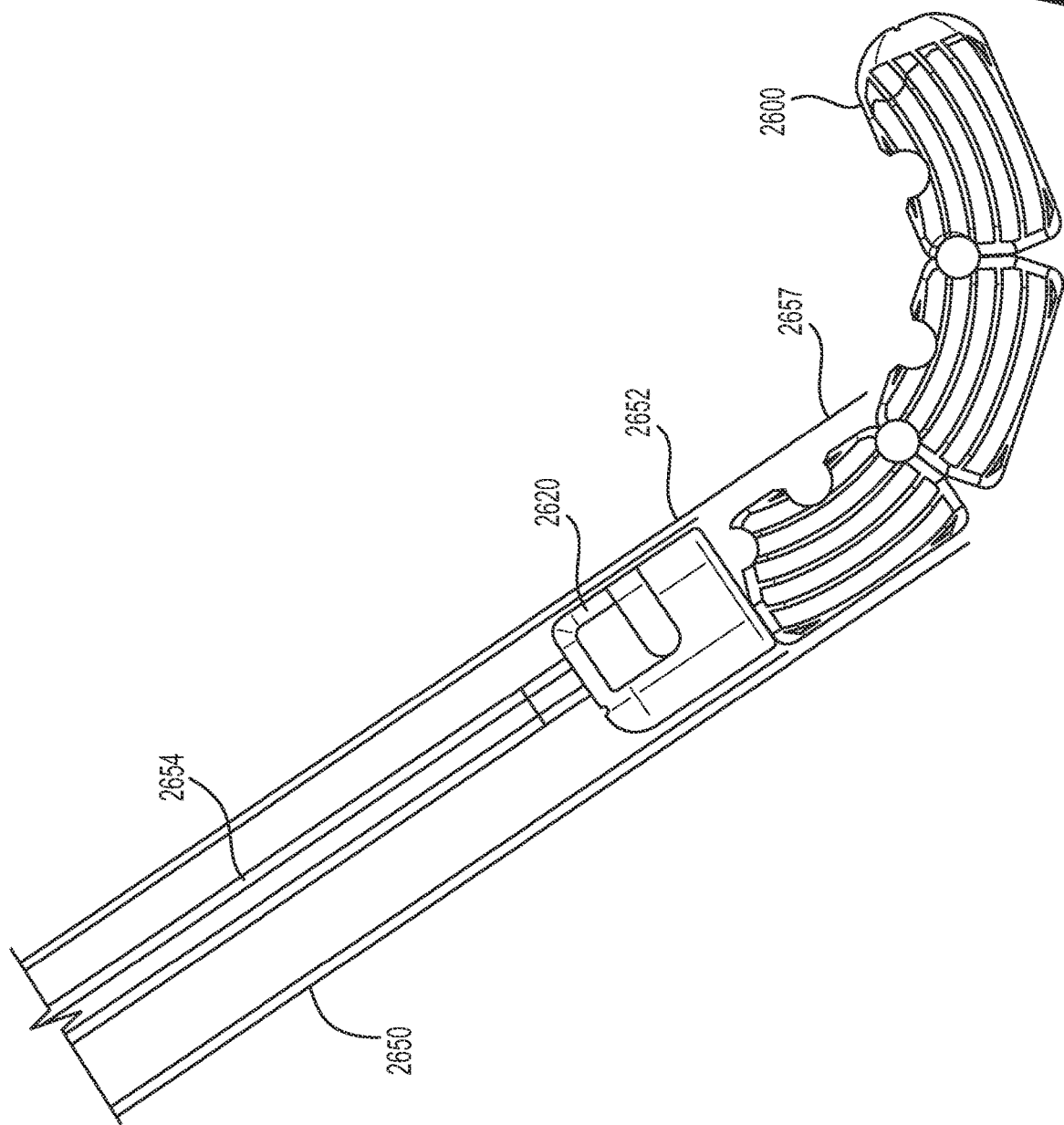
FIG. 18.3

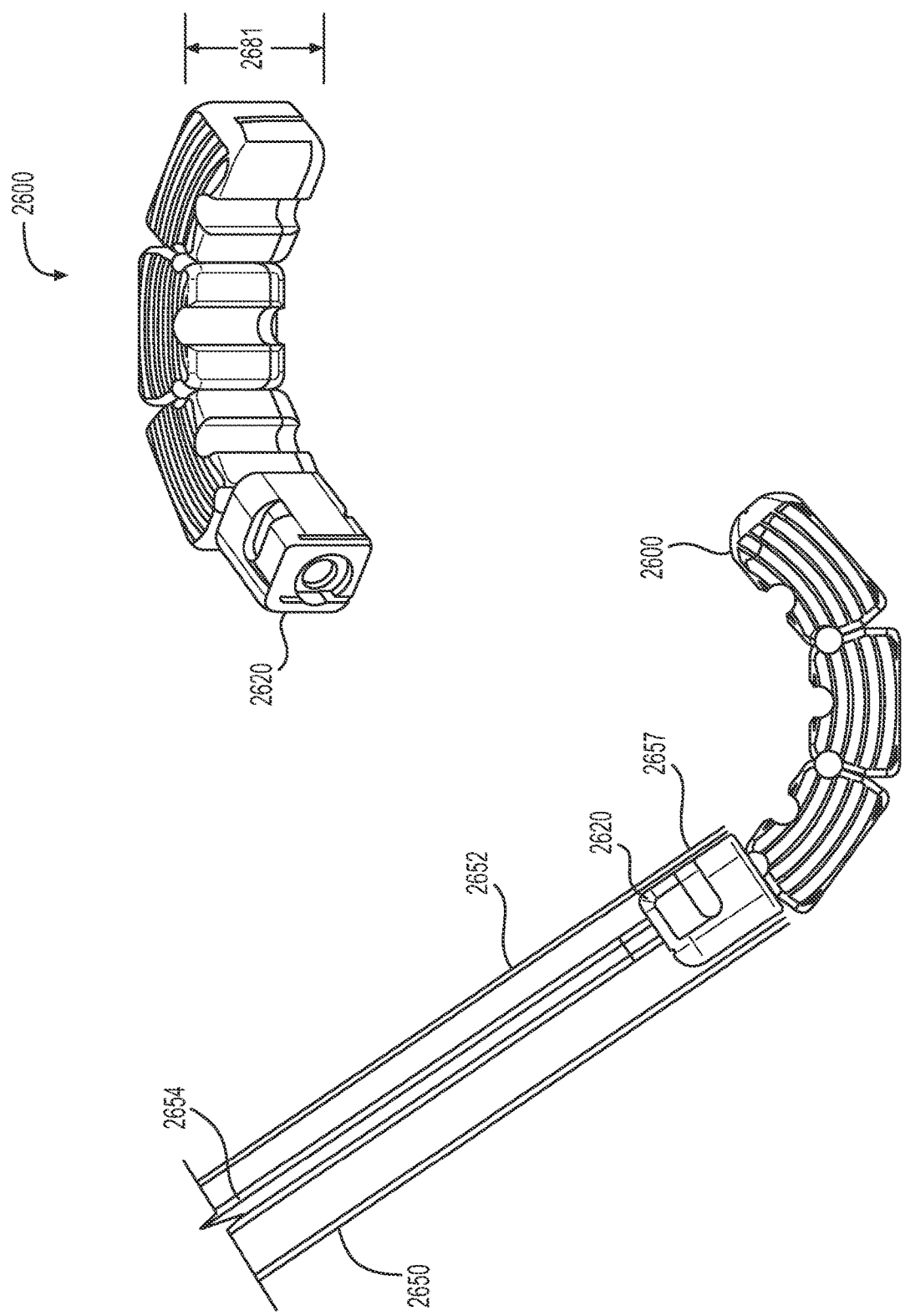
FIG. 18.4

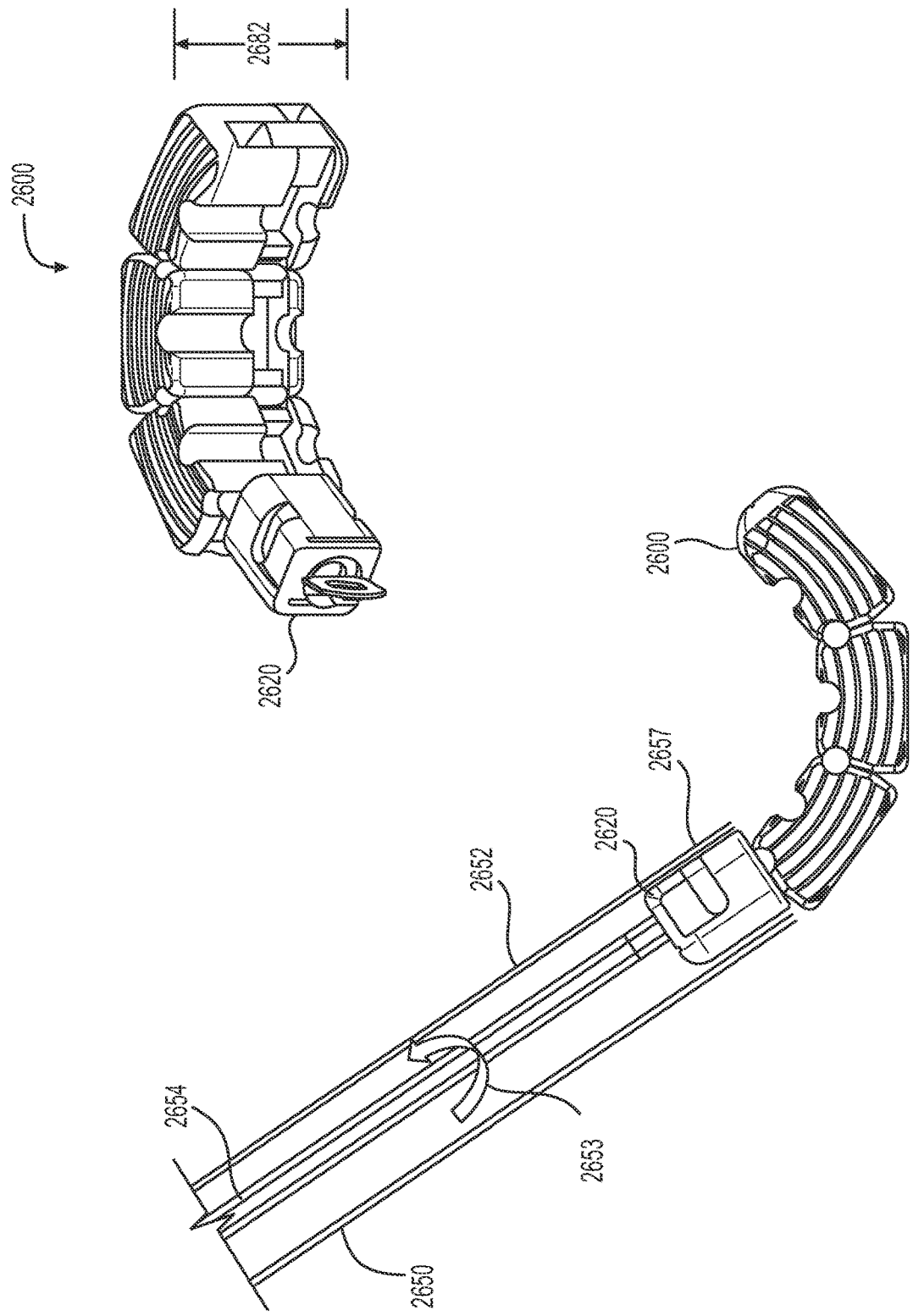
FIG. 18.5

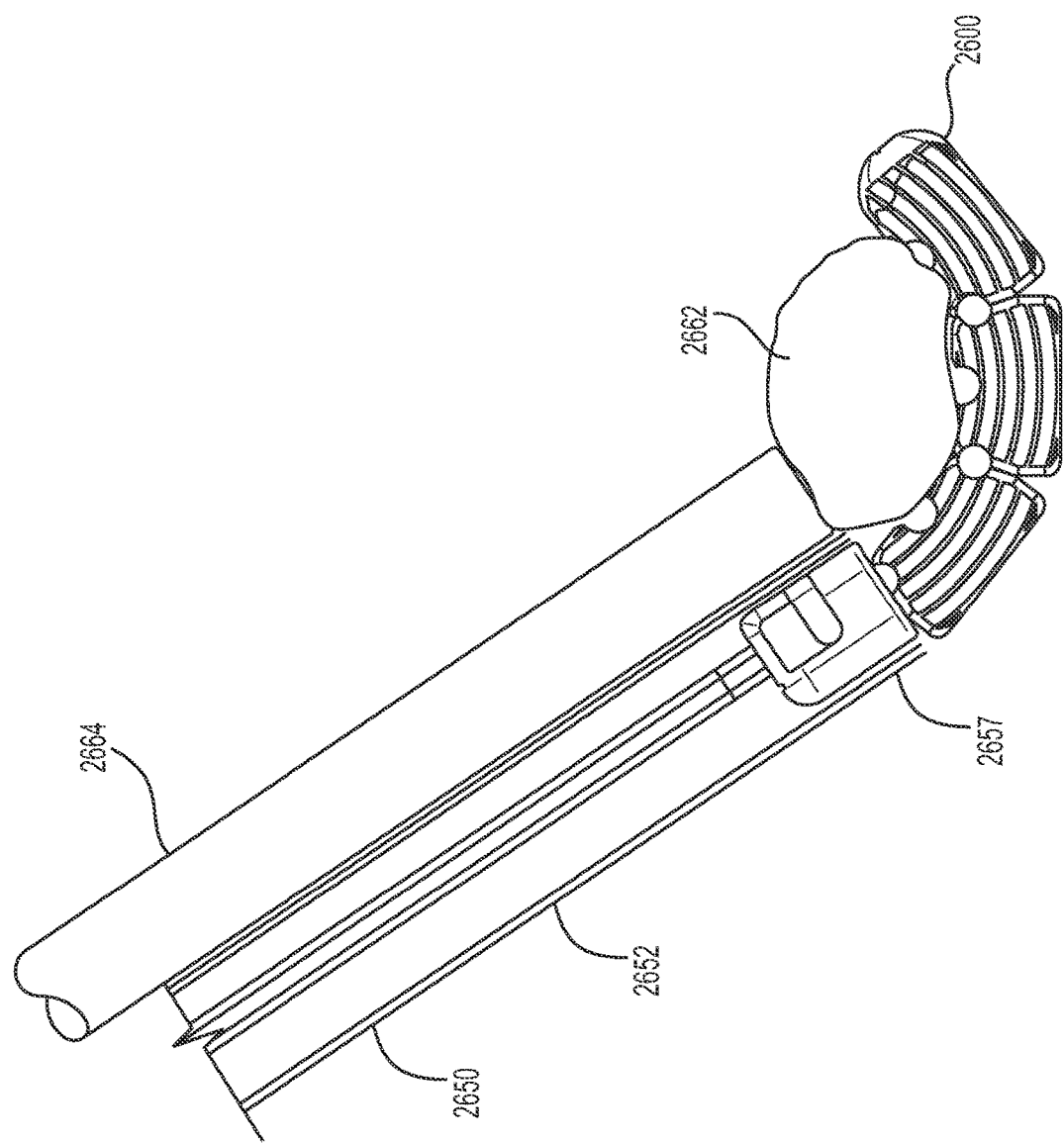
FIG. 18.6

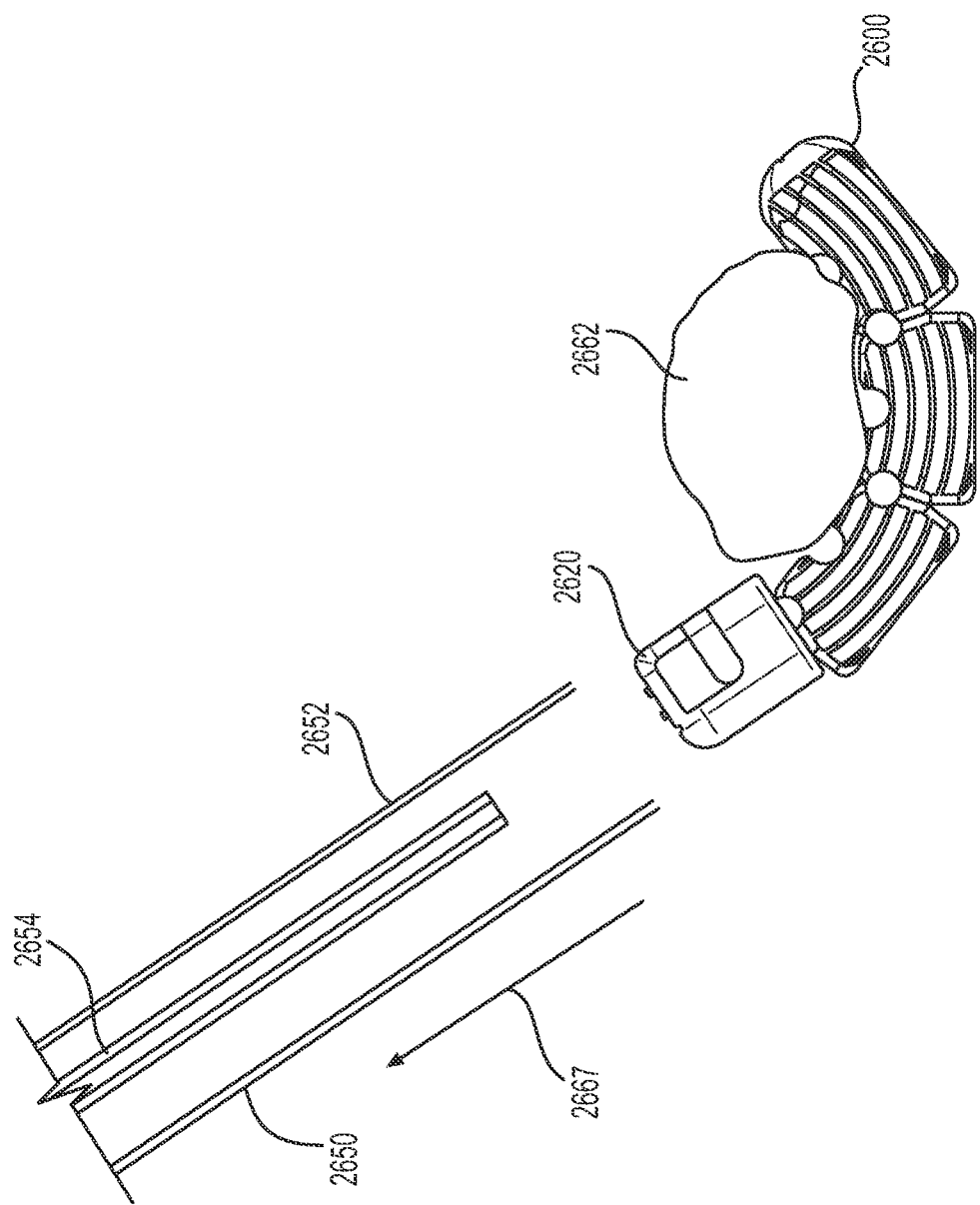
FIG. 18.7

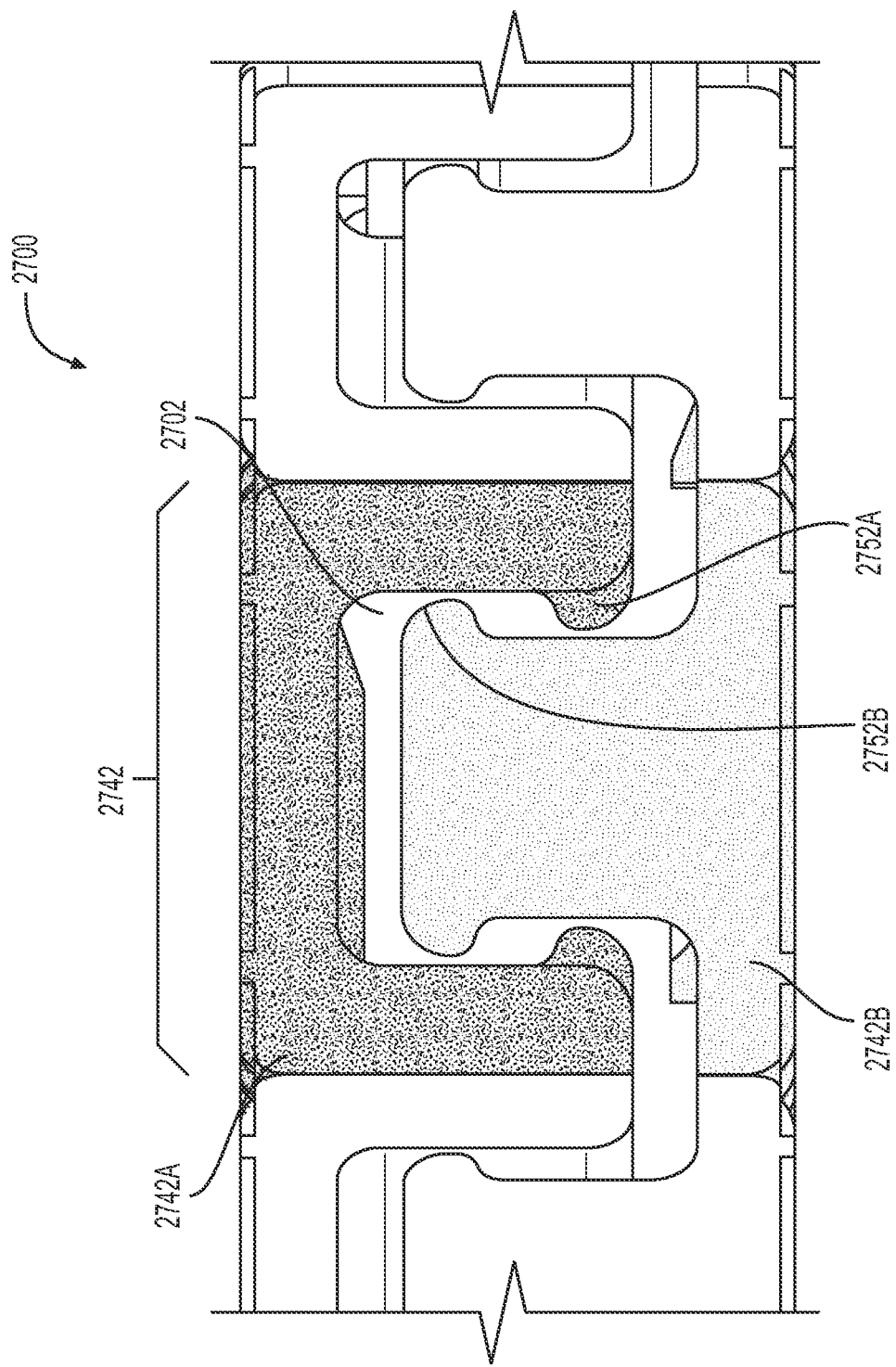
FIG. 19.1

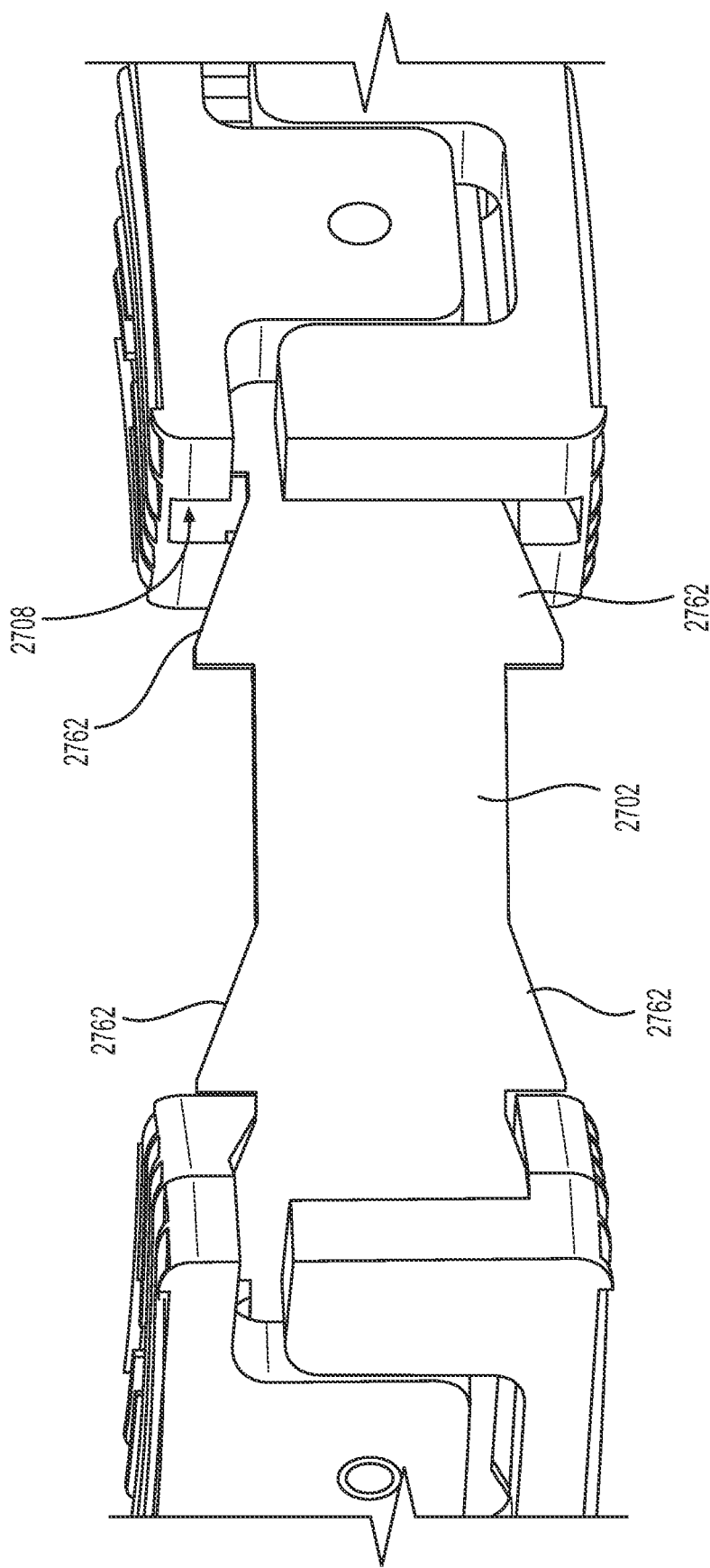
FIG. 19.2

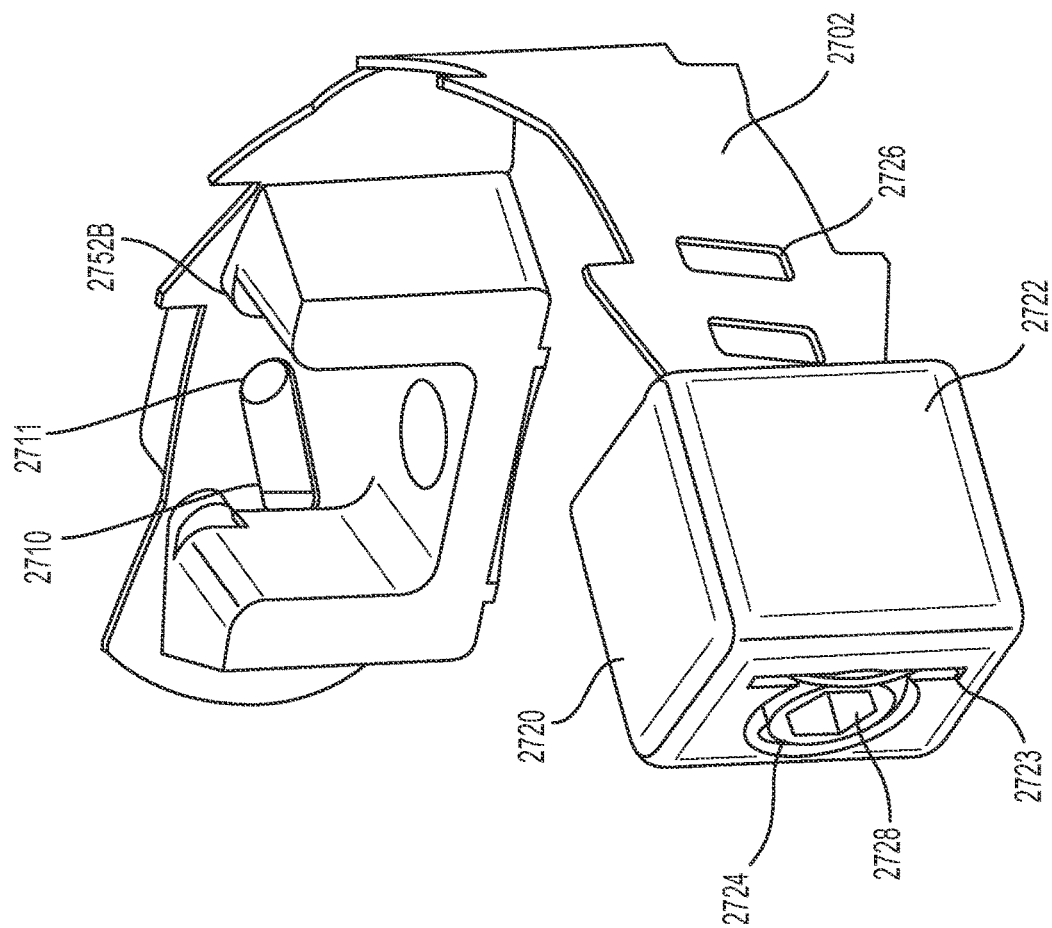
FIG. 19.3

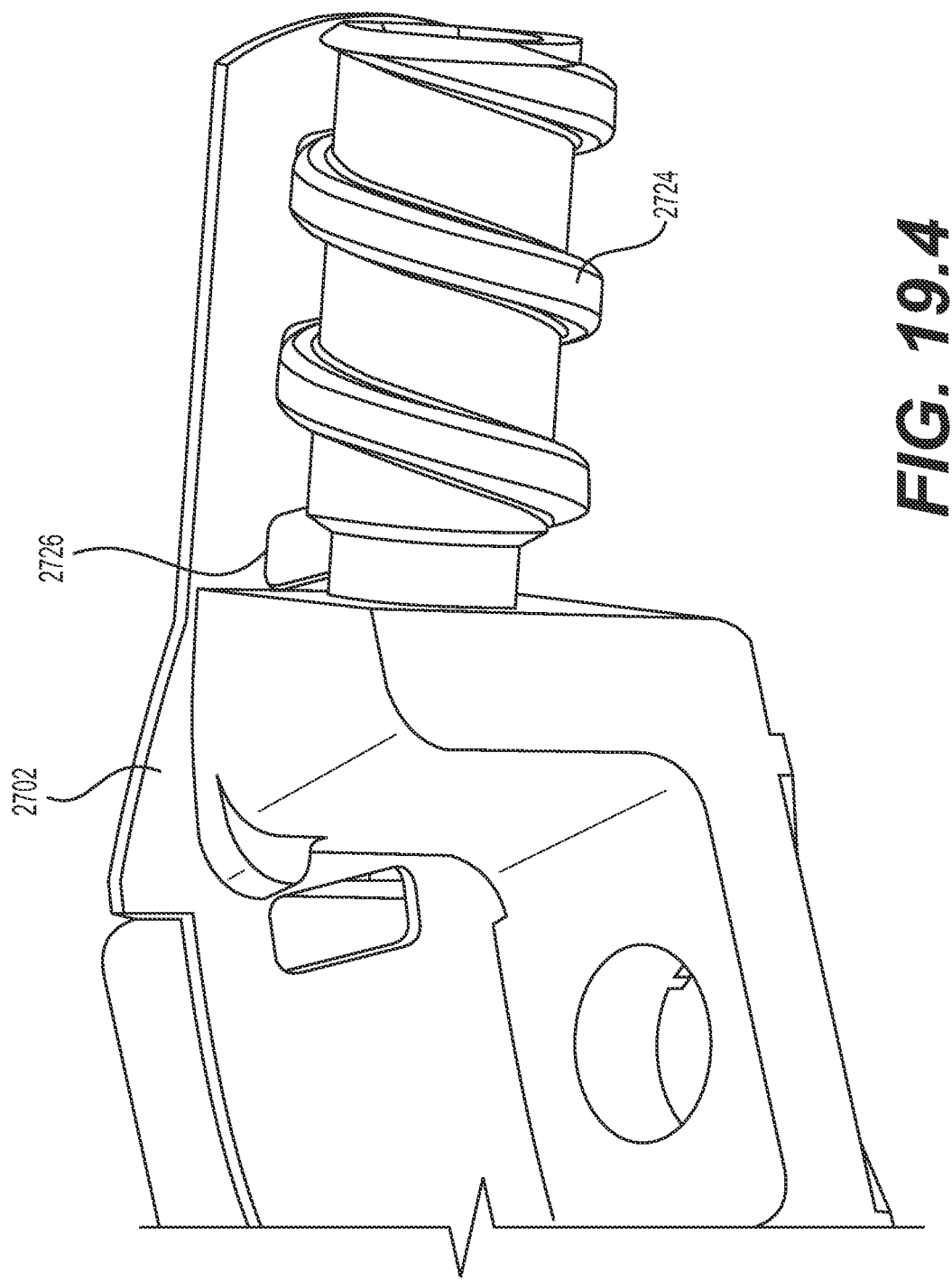
FIG. 19.4

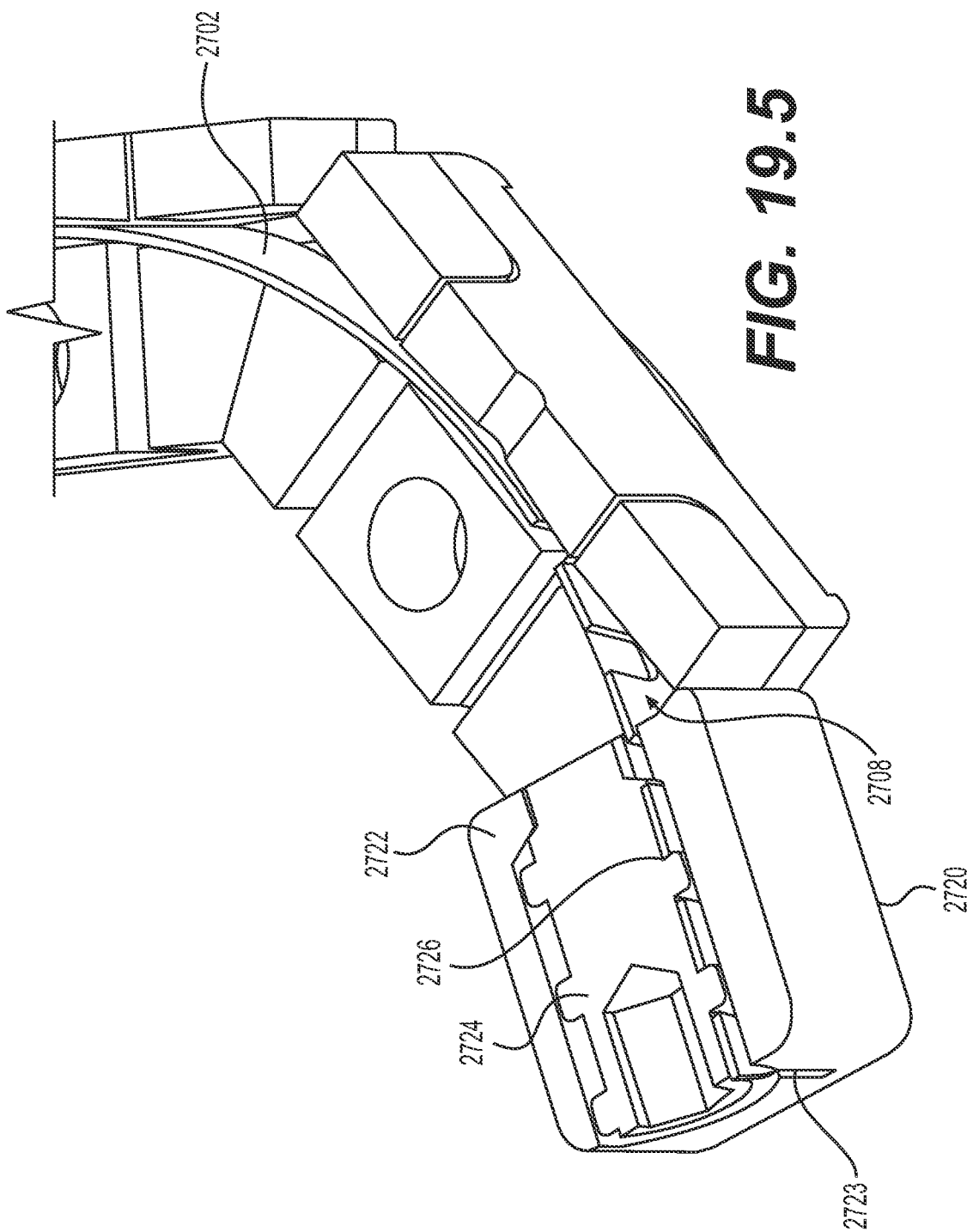
FIG. 19.5

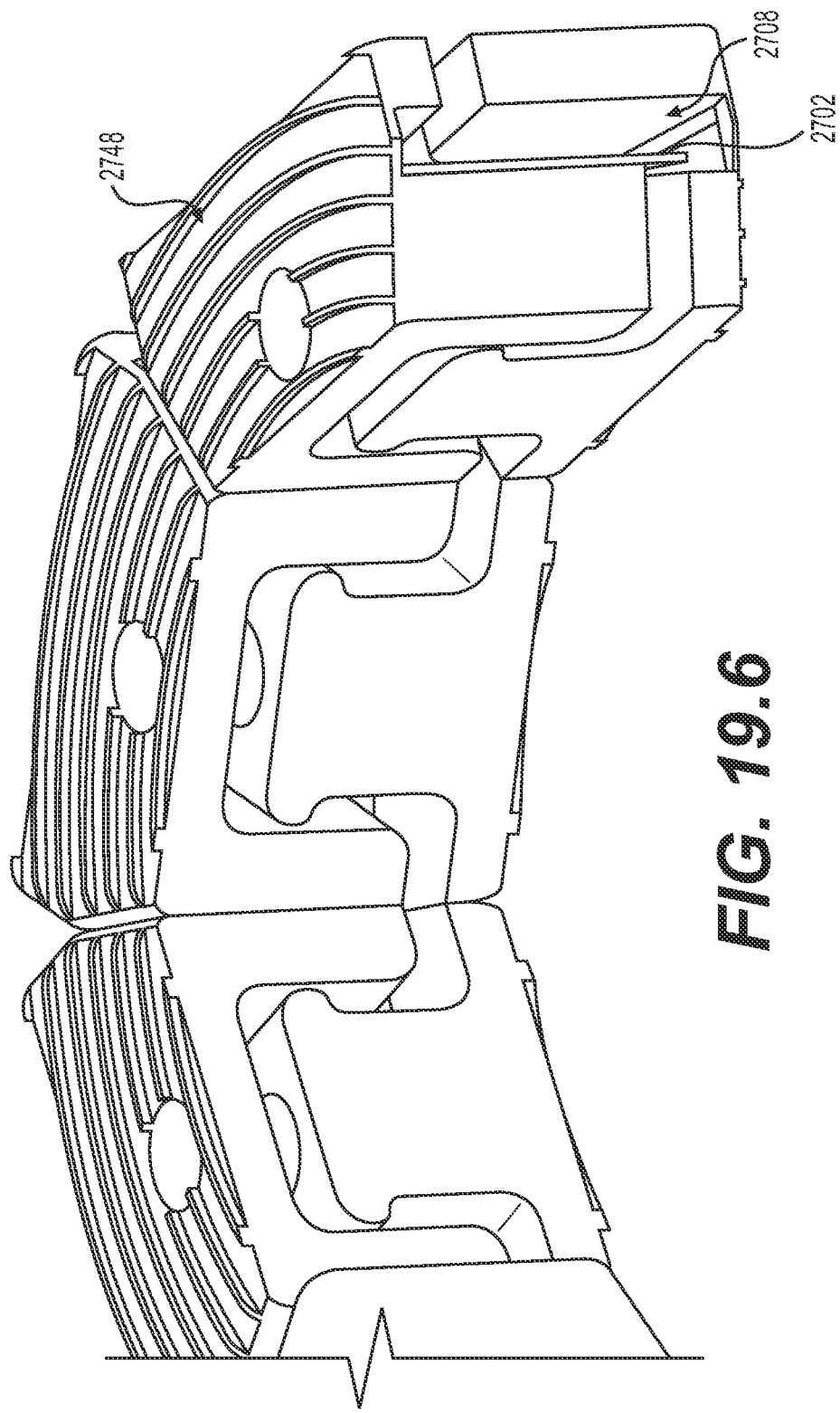
FIG. 19.6

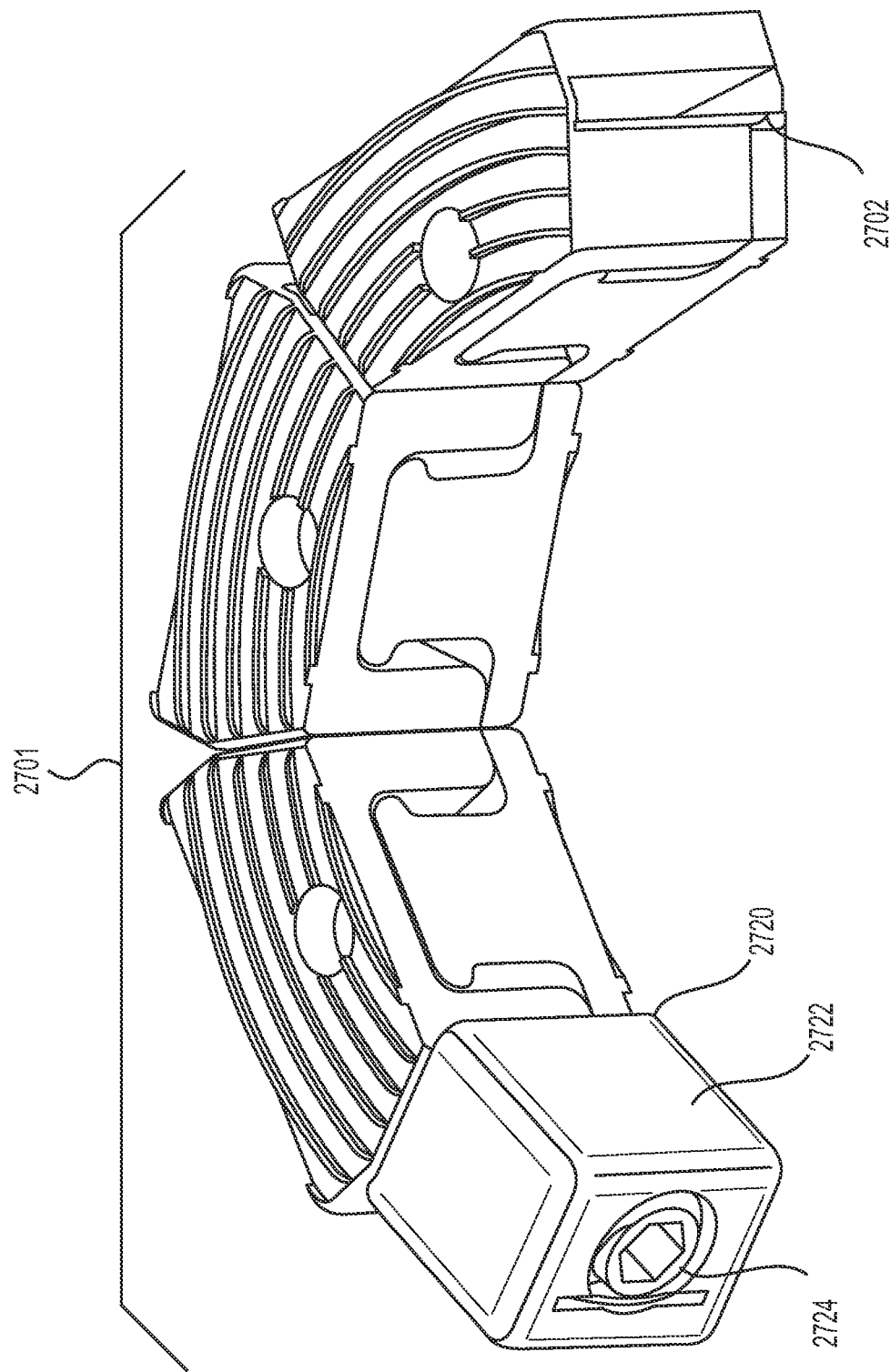
FIG. 19.7

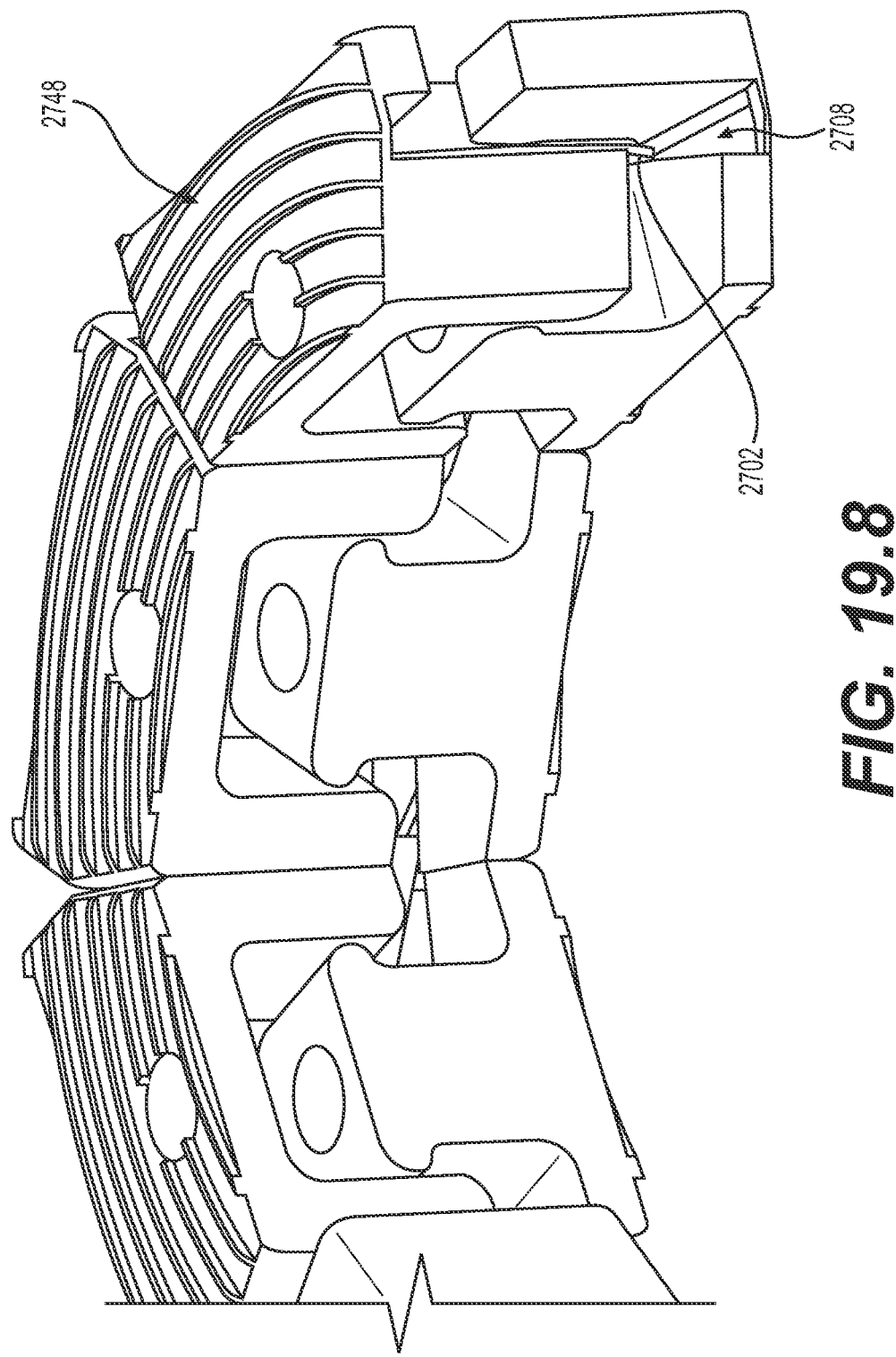
FIG. 19.8

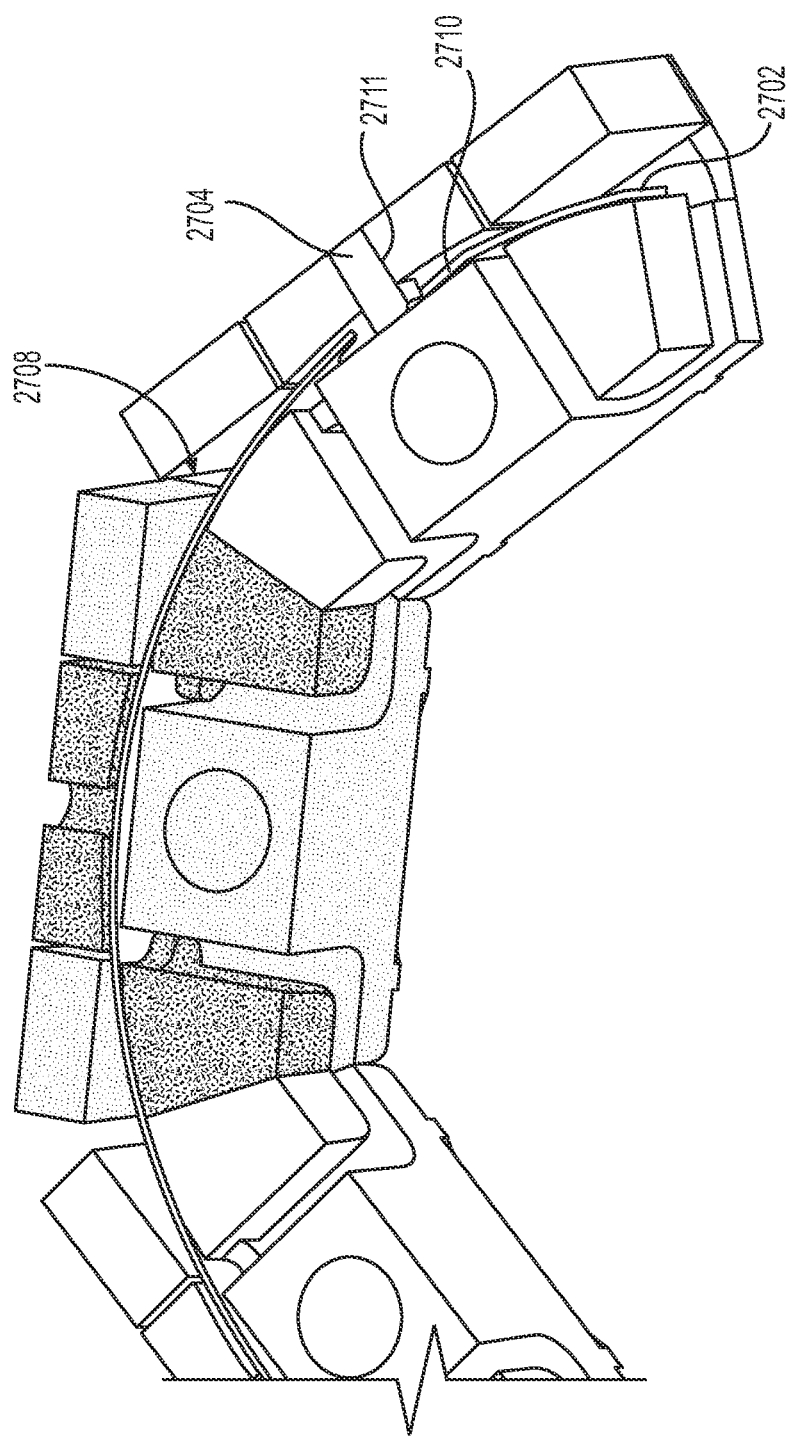
FIG. 19.9

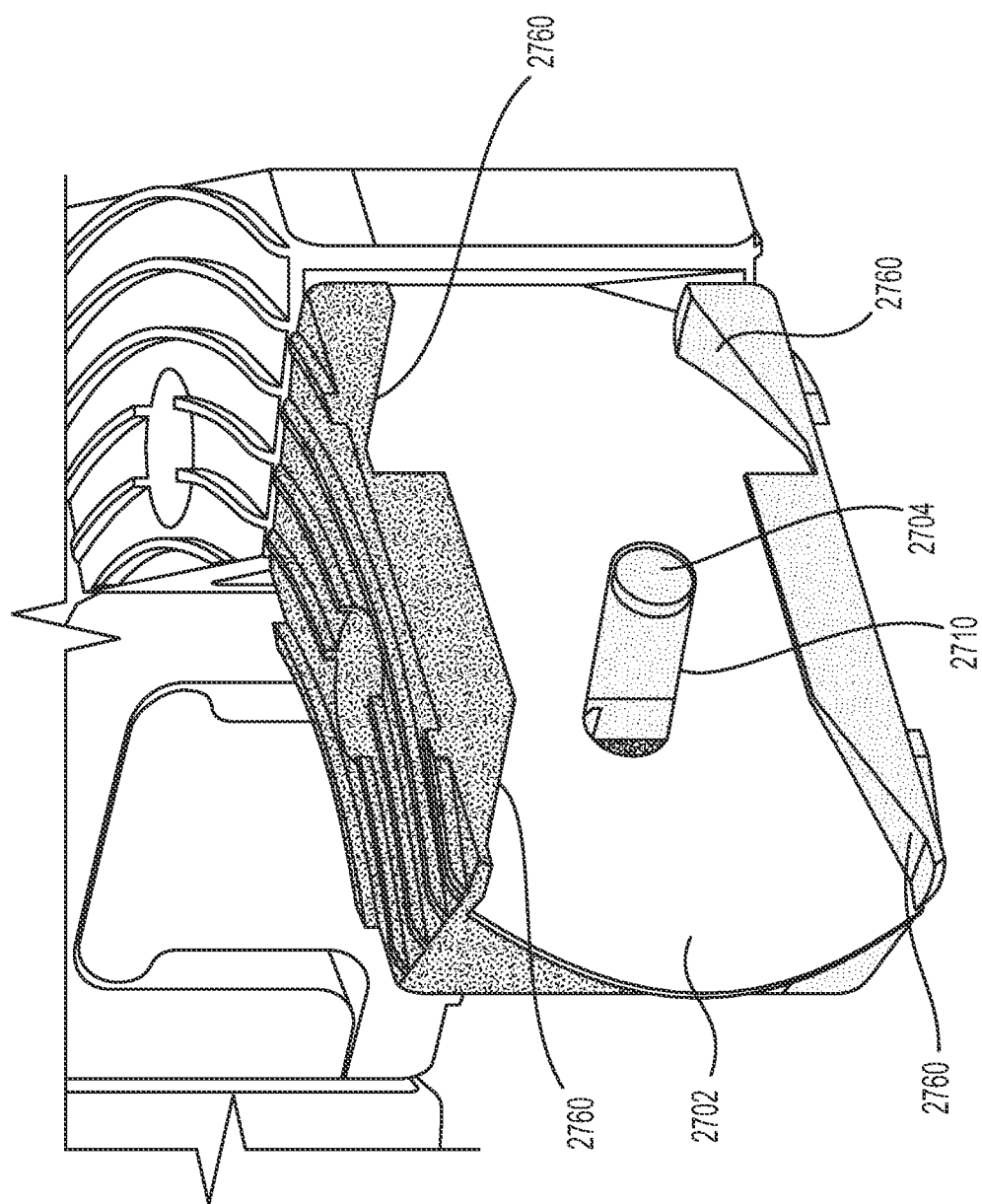
FIG. 19.10

COILING IMPLANTABLE PROSTHESES AND METHODS FOR IMPLANTING

CROSS REFERENCE TO RELATED APPLICATIONS

This application is a continuation of U.S. application Ser. No. 17/663,469, filed May 16, 2022 (U.S. Patent Application Publication Number US2022/0401226A1, published Dec. 22, 2022), which is a continuation of U.S. application Ser. No. 16/987,566, filed Aug. 7, 2020, now U.S. Pat. No. 11,331,198, which is a continuation of U.S. application Ser. No. 15/889,704, filed Feb. 6, 2018, now U.S. Pat. No. 10,751,195, which is a division of U.S. application Ser. No. 14/882,633, filed Oct. 14, 2015, now U.S. Pat. No. 9,901,457, which claims the benefit of U.S. Provisional Patent Application No. 62/064,603, filed Oct. 16, 2014, all of which are herein incorporated by reference in their entirety.

BACKGROUND

1. Field

The present embodiments relates generally to implantable prostheses and, in particular, to an implantable prosthesis that has a biased coiling member and a conforming coiling member, and which may be implanted between vertebrae, for example, as a disc fusion implant.

2. Description of Related Art

Implantable prostheses are commonly used to replace damaged, diseased, or otherwise defective tissue. In some cases, implantable prostheses, such as spinal fusion implants, may be embedded between adjacent vertebrae, partially or fully replacing the tissue disposed between the vertebrae. Implantation of such devices may require invasive surgery. There is a need in the art for spinal fusion implants that may be implanted through a minimally invasive procedure.

SUMMARY

Aspects of the present embodiments provide an implantable prosthesis having a biased coiling member and a conforming coiling member that is curved or coiled by the biased coiling member.

An aspect provides an implantable prosthesis having a biased coiling member biased to curve from a substantially linear configuration to a nonlinear configuration, and a conforming coiling member that is engaged with and curved by the biased coiling member from the substantially linear configuration to the nonlinear configuration. The biased coiling member may define a longitudinal axis when in the substantially linear configuration. The biased coiling member and the conforming coiling member may move relative to each other along the longitudinal axis.

In another aspect, the biased coiling member and the conforming coiling member may move relative to each other along the longitudinal axis in transitioning from the substantially linear configuration to the nonlinear configuration.

In another aspect, when the biased coiling member and the conforming coiling member move relative to each other along the longitudinal axis, the biased coiling member may force a first component of the conforming coiling member to move relative to a second component of the conforming coiling member in a direction generally perpendicular to the longitudinal axis.

In another aspect, the implantable prosthesis may include a fastener assembly engaging the biased coiling member with the conforming coiling member. The fastener assembly may hold a first longitudinal face of the biased coiling member laterally against a first longitudinal face of the conforming coiling member. The fastener assembly may allow the first longitudinal face of the biased coiling member to move longitudinally relative to, and slide against, the first longitudinal face of the conforming coiling member in transitioning from the substantially linear configuration to the nonlinear configuration.

In another aspect, the fastener assembly may include a longitudinal slot on one of the biased coiling member and the conforming coiling member, and a longitudinally fixed connection on the other of the biased coiling member and conforming coiling member.

In another aspect, the fastener assembly may include a protrusion disposed laterally through the longitudinal slot and the longitudinally fixed connection may include an opening corresponding to the shape and dimensions of the protrusion.

In another aspect, the implantable prosthesis may include a first fastener assembly and a second fastener assembly. The second fastener assembly may engage the biased coiling member with the conforming coiling member, and may hold the first longitudinal face of the biased coiling member laterally against the first longitudinal face of the conforming coiling member. The first fastener assembly may be disposed at a proximal portion of the implantable prosthesis that is on an outer coil of the implantable prosthesis when in the nonlinear configuration. The second fastener assembly may be disposed at a distal portion of the implantable prosthesis that is on an inner coil of the implantable prosthesis when in the nonlinear configuration. The second fastener assembly may allow longitudinal relative movement between the first longitudinal face of the biased coiling member and the first longitudinal face of the conforming coiling member that is less than the longitudinal relative movement allowed by the first fastener assembly.

In another aspect, the second fastener assembly may allow substantially no longitudinal relative movement between the first longitudinal face of the biased coiling member and the first longitudinal face of the conforming coiling member.

In another aspect, a fastener assembly may comprise a longitudinal slot defined by one of the biased coiling member and the conforming coiling member, an opening defined by the other of the biased coiling member and the conforming coiling member, and a fastener having a laterally extending protrusion disposed through the longitudinal slot and the opening. The laterally extending protrusion may substantially fully occupy the opening to substantially fix the fastener relative to the other of the biased coiling member and the conforming coiling member. The laterally extending protrusion may be slidable within the longitudinal slot.

In another aspect, the biased coiling member may define an instrument opening at a proximal portion of the implantable prosthesis. The instrument opening may be disposed on an outer coil of the implantable prosthesis when in the nonlinear configuration.

In another aspect, the biased coiling member may be a coil spring band and the conforming coiling member may be a continuous strip.

In another aspect, the conforming coiling member may include a plurality of ribs spanning the lateral dimension of the conforming coiling member.

In another aspect, at a proximal portion of the conforming coiling member, the plurality of ribs may decrease in height toward a proximal end of the conforming coiling member to facilitate a substantially round outside contour when in the nonlinear configuration.

In another aspect, the biased coiling member may be a coil spring band and the conforming coiling member may be a plurality of coiling member segments attached to the coil spring band.

In another aspect, the conforming coiling member may include a segment having an upper component and a lower component. The upper component and the lower component may move relative to each other. The movement of the biased coiling member through the segment may move the upper component away from the lower component to adjust the height of the implantable prosthesis.

In another aspect, an implantable prosthesis may include a laterally extending pin fixedly attached to the biased coiling member. At least one of the upper component and the lower component may define an elongated inclined opening. The pin may be disposed laterally through the elongated inclined opening and slidably engaged with the elongated inclined opening. Relative displacement of the biased coiling member and the conforming coiling member may move the pin within the elongated inclined opening such that the pin forces the at least one of the upper component and the lower component away from the other of the upper component and the lower component.

In another aspect, the upper component may define a first elongated inclined opening and the lower component may define a second elongated inclined opening. The first elongated inclined opening and the second elongated inclined opening may be inclined in opposite directions. The pin may be disposed laterally through the first elongated inclined opening and the second elongated inclined opening, and, in moving in a longitudinal direction of the implantable prosthesis, the pin may push on an edge of the first elongated inclined opening and an edge of the second elongated inclined opening to move the upper component away from the lower component.

In another aspect, a conforming coiling member of an implantable prosthesis may have a first lateral dimension generally perpendicular to the longitudinal axis, and a biased coiling member of the implantable prosthesis may have a second lateral dimension generally perpendicular to the longitudinal axis, with the first lateral dimension of the conforming coiling member being substantially equal to or greater than the second lateral dimension of the biased coiling member.

Another aspect provides a method for implanting an implantable prosthesis. The method may include holding the implantable prosthesis in a substantially linear configuration within a cannula, the implantable prosthesis having a biased coiling member engaged with a conforming coiling member. The biased coiling member may define a longitudinal axis, and the biased coiling member may be substantially fixed to the conforming coiling member in a direction lateral to the longitudinal axis. The cannula may be inserted into a surgical site. The implantable prosthesis may be advanced toward a distal end of the cannula. The implantable prosthesis may be ejected from the cannula such that the biased coiling member curves the conforming coiling member into a nonlinear configuration as the implantable prosthesis exits the cannula. The biased coiling member and the conforming coiling member may be moved relative to each other along the longitudinal axis. The implantable prosthesis may be released from the cannula and into the surgical site.

In another aspect, moving the biased coiling member and the conforming coiling member relative to each other along the longitudinal axis may include sliding the biased coiling member against the conforming coiling member at a proximal portion of the implantable prosthesis and coiling the implantable prosthesis.

In another aspect, moving the biased coiling member and the conforming coiling member relative to each other along the longitudinal axis may move an upper component of the conforming coiling member away from a lower component of the conforming member to adjust a height of the implantable prosthesis.

Another aspect provides a spinal prosthesis including a biased coiling member biased to curve from a substantially linear configuration to a nonlinear configuration, and a conforming coiling member slidably attached to the biased coiling member. The biased coiling member and the conforming coiling member may extend in a longitudinal direction. The biased coiling member may curve the conforming coiling member from the substantially linear configuration to the nonlinear configuration. The slidable attachment between the biased coiling member and the conforming coiling member may allow the biased coiling member and the conforming coiling member to displace relative to each other along the longitudinal direction.

In another aspect, a biased coiling member may be a coil spring band and a conforming coiling member may be a plurality of coiling member segments attached to the coil spring band.

In another aspect, a plurality of coiling member segments may comprise a plurality of wedge-shaped segments. The wedge-shaped segments may be separate from each other or may be attached to each other. In one aspect, the wedge-shaped segments may be each attached to the biased coiling member and may be separate from each other and may move independently from each other. In another aspect, the wedge-shaped segments may be attached to the biased coiling member and also connected to each other, for example, by ball and socket connections.

In another aspect, a biased coiling member may be a coil spring band and a conforming coiling member may be a continuous strip. A continuous strip may be, for example, an integrally-formed strip of plastic attached to the biased coiling member.

In another aspect, a continuous strip may include provisions for enhancing the coiling of the strip. For example, a continuous strip may include grooves or openings that enhance the ability of the strip to bend, coil, or otherwise flex.

In another aspect, a continuous strip may include provisions for attaching the continuous strip to the biased coiling member. For example, a continuous strip may include openings, slots, or tabs that hold the biased coiling member.

In another aspect, an implantable prosthesis may include provisions for height adjustment. A conforming coiling member may include a segment having an upper component and a lower component. The upper component and the lower component may move relative to each other. Movement of the biased coiling member through the segment may move the upper component away from the lower component to adjust the height of the implantable prosthesis.

Other systems, methods, features, and advantages of the present embodiments will be, or will become, apparent to one of ordinary skill in the art upon examination of the following figures and detailed description. It is intended that all such additional systems, methods, features and advantages be included within this description and this summary, be within the scope of the present embodiments, and be protected by the following claims.

BRIEF DESCRIPTION OF THE DRAWINGS

The present embodiments can be better understood with reference to the following drawings and description. The components in the figures are not necessarily to scale, emphasis instead being placed upon illustrating the principles of the present embodiments. Moreover, in the figures, like reference numerals designate corresponding parts throughout the different views.

FIG. 5.1 is a schematic diagram illustrating a side view of an embodiment of a biased coiling member in an uncoiled configuration;

FIG. 5.2 is a schematic diagram illustrating a cross-sectional view of an embodiment of a biased coiling member with a bone growth promoting agent applied to an entire outer surface of the member;

FIG. 5.3 is a schematic diagram illustrating a cross-sectional view of an embodiment of a biased coiling member with a bone growth promoting agent that is selectively applied to an outer surface of the member;

FIG. 6.1 is a schematic diagram illustrating a side view of an embodiment of a conforming coiling member in an uncoiled configuration;

FIG. 6.2 is a schematic diagram illustrating a top view of the conforming coiling member of FIG. 6.2;

FIG. 6.3 is a schematic diagram illustrating a side view of another embodiment of a conforming coiling member in an uncoiled configuration;

FIG. 6.4 is a schematic diagram illustrating a top view of the conforming coiling member of FIG. 6.3;

FIG. 12.1 is a schematic diagram illustrating an isometric view of an embodiment of an implantable prosthesis;

FIG. 12.2 is a schematic diagram illustrating an isometric view of an embodiment of the biased coiling member of FIG. 12.1 in a coiled configuration;

FIG. 12.3 is a schematic diagram illustrating a detail isometric view of an embodiment of a proximal portion of the implantable prosthesis of FIG. 12.1;

FIG. 12.4 is a schematic diagram illustrating a detail isometric view of an embodiment of a distal portion of the implantable prosthesis of FIG. 12.1;

FIG. 12.5 is a schematic diagram illustrating an isometric view of the implantable prosthesis of FIG. 12.1, showing the outside face of the biased coiling member of the implantable prosthesis;

FIG. 12.6 is a schematic diagram illustrating an isolated isometric view of an embodiment of a first fastener of the implantable prosthesis of FIG. 12.1;

FIG. 12.7 is a schematic diagram illustrating an isolated isometric view of an embodiment of a second fastener of the implantable prosthesis of FIG. 12.1;

FIG. 12.8 is a schematic diagram illustrating a cross-sectional view of the distal portion of the implantable prosthesis shown in FIG. 12.4, taken along line B-B of FIG. 12.5;

FIG. 12.9 is a schematic diagram illustrating a cross-sectional view of the proximal portion of the implantable prosthesis shown in FIG. 12.3, taken along line B-B of FIG. 12.5;

FIG. 12.10 is a schematic diagram illustrating a cross-sectional view of the proximal portion of the implantable prosthesis shown in FIG. 12.3, taken along line A-A of FIG. 12.3, showing the fastener with a straight, unformed shank;

FIG. 12.11 is a schematic diagram illustrating another cross-sectional view the proximal portion of the implantable prosthesis shown in FIG. 12.3, taken along line A-A of FIG. 12.3, showing the fastener with a formed shank;

FIG. 13.1 is a schematic diagram illustrating an outside detail view of an embodiment of an implantable prosthesis having a conforming coiling member connected to a biased coiling member by a tab disposed in a slot, at a proximal portion of the implantable prosthesis;

FIG. 13.2 is a schematic diagram illustrating an outside detail view of an embodiment of an implantable prosthesis having a conforming coiling member connected to a biased coiling member by a tab disposed in a slot, at a distal portion of the implantable prosthesis;

FIG. 14.1 is a schematic diagram illustrating an isometric view of an embodiment of a pin fastener for connecting a biased coiling member to a conforming coiling member;

FIG. 14.2 is a schematic diagram illustrating an isometric view of the inside of a distal portion of an implantable prosthesis having a biased coiling member and a conforming coiling member connected by the fastener of FIG. 14.1;

FIG. 14.3 is a schematic diagram illustrating an isometric view of the outside of the distal portion of the implantable prosthesis shown in FIG. 14.2;

FIGS. 15.1-15.4 are schematic diagrams illustrating an embodiment for delivering an implantable prosthesis as an interbody fusion device using a minimally invasive surgery technique via a transforaminal lumbar interbody fusion (TLIF) approach;

FIGS. 16.1-16.5 are schematic diagrams illustrating an embodiment for delivering an implantable prosthesis as an interbody fusion device using a minimally invasive surgery technique via a lateral approach;

FIG. 17.1 is a schematic diagram illustrating an isometric outside detail view of an embodiment of a height-adjustable implantable prosthesis;

FIG. 17.2 is a schematic diagram illustrating an isometric outside detail view of the segments of the height-adjustable implantable prosthesis of FIG. 17.1;

FIG. 17.3 is a schematic diagram illustrating an isometric top partial cross-sectional view of a portion of the implantable prosthesis of FIG. 17.1, with portions of a segment hidden to show the engagement between a pin, upper component, and biased coiling member of the implantable prosthesis, according to an embodiment;

FIG. 17.4 is a schematic diagram illustrating an isometric top partial cross-sectional view of a portion of the implantable prosthesis of FIG. 17.1, with portions of a segment hidden to show the engagement between a pin, lower component, and biased coiling member of the implantable prosthesis, according to an embodiment;

FIG. 17.5 is a schematic diagram illustrating an isometric detail view of the implantable prosthesis of FIG. 17.1, with the segments hidden to show the engagement between the pins, biased coiling member, and actuator of the implantable prosthesis, according to an embodiment;

FIG. 17.6 is a schematic diagram illustrating an isometric detail view of a portion of the implantable prosthesis of FIG. 17.1, with the segments and the housing of the actuator hidden to show the engagement between the pins and the biased coiling member, and the engagement between the tightening screw of the actuator and the biased coiling member, according to an embodiment;

FIG. 17.7 is a schematic diagram illustrating an isometric detail end view of a portion of the implantable prosthesis of FIG. 17.1, in a minimal expansion state, with the upper and lower components a segment shown in different shading to illustrate the engagement between a pin and slots, and to illustrate the interdigitating upper and lower components with the biased coiling member, according to an embodiment;

FIG. 17.8 is a schematic diagram illustrating an isometric detail view of a portion of the implantable prosthesis of FIG. 17.1 in a maximum expansion state, showing the engagement between the pins and slots and the interdigitating of the upper and lower components of the segments, according to an embodiment;

FIG. 17.9 is a schematic diagram illustrating an isometric inside detail view of a portion of the implantable prosthesis of FIG. 17.1 in a mid-expansion state, showing the tongue and groove connection between the upper and lower components of a segment, according to an embodiment;

FIG. 17.10 is a schematic diagram illustrating an isometric outside detail view of a portion of the implantable prosthesis of FIG. 17.1 in a mid-expansion state, showing the engagement between the pins and slots and the interdigitating of the upper and lower components of the segments, according to an embodiment;

FIG. 17.11 is a schematic diagram illustrating an isometric detail cross-sectional view of a distal portion of the implantable prosthesis of FIG. 17.1 in a minimal expansion state, with the upper and lower components of the distal segment shown in different shading to illustrate the engagement between the pins and slots, the interdigitating of the upper and lower components of the distal segment, and the passageway defined between the upper and lower components permitting motion of the biased coiling member between straight and curved states, according to an embodiment;

FIG. 17.12 is a schematic diagram of a detail side view of an alternative embodiment of the inclined slots of the upper and lower components of a segment of the implantable prosthesis of FIG. 17.1, with recesses formed in the slots, into which a pin may seat;

FIGS. 18.1-18.7 are schematic diagrams illustrating an embodiment for delivering the implantable prosthesis of FIG. 17.1 as an interbody fusion device;

FIGS. 19.1 is a schematic diagram illustrating an outside detail partial view of another embodiment of a height-adjustable implantable prosthesis;

FIG. 19.2 is a schematic diagram illustrating an outside detail view of a portion of the implantable prosthesis of FIGS. 19.1 and 19.7 with a segment hidden to show the inclined surfaces of the biased coiling member, which engage with mating inclined surfaces on the segments, according to an embodiment;

FIG. 19.3 is a schematic diagram illustrating a proximal isometric view of a portion of the implantable prosthesis of FIGS. 19.1 and 19.7 with two and one-half segments hidden to show the actuator including a screw and a housing, according to an embodiment;

FIG. 19.4 is a schematic diagram illustrating an isometric detail view of the tightening screw of the implantable prosthesis of FIGS. 19.1 and 19.7, engaged with mating slots defined in the biased coiling member and used for height expansion of the implantable prosthesis, according to an embodiment;

FIG. 19.5 is a schematic diagram illustrating an isometric cross-sectional view of the actuator of the implantable prosthesis of FIGS. 19.1 and 19.7, with tightening screw engaged with mating slots in the biased coiling member and used for height expansion of the implantable prosthesis, according to an embodiment;

FIG. 19.6 is a schematic diagram illustrating an isometric inside view of a portion of the implantable prosthesis of FIGS. 19.1 and 19.7 in a mid-expanded state, according to an embodiment;

FIG. 19.7 is a schematic diagram illustrating an isometric inside view of the implantable prosthesis FIG. 19.1 in a closed state, with the tightening screw and housing of the actuator in the view, according to an embodiment;

FIG. 19.8 is a schematic diagram illustrating an isometric inside detail view of a portion of the implantable prosthesis of FIGS. 19.1 and 19.7 in a fully expanded state, according to an embodiment;

FIG. 19.9 is a schematic diagram illustrating an isometric inside cross-sectional view of a portion of the implantable prosthesis of FIGS. 19.1 and 19.7 in a mid-expanded state, with different shading used to illustrate engagement details between the upper and lower components of a segment, and to illustrate how the distal end segment is retained by a pin inserted into a slot in the biased coiling member, according to an embodiment;

FIG. 19.10 is a schematic diagram illustrating an isometric outside section view of a portion of the implantable prosthesis of FIGS. 19.1 and 19.7 in a closed state, with a portion of the distal end segment hidden, and with different shading used to illustrate engagement details between the upper and lower components of a segment, to illustrate how the distal end segment is retained by a pin inserted into a slot in the biased coiling member, and to illustrate the inclined surfaces on the biased coiling member that mate with the inclined surfaces on the upper and lower components, according to an embodiment.

DETAILED DESCRIPTION

Embodiments provide a coiling implantable prosthesis that includes a biased coiling member and a conforming coiling member, and which may be implanted in a surgical procedure that minimizes incision sizes and may be considered less invasive than typical implant procedures, especially spinal implant procedures.

Figure 1:
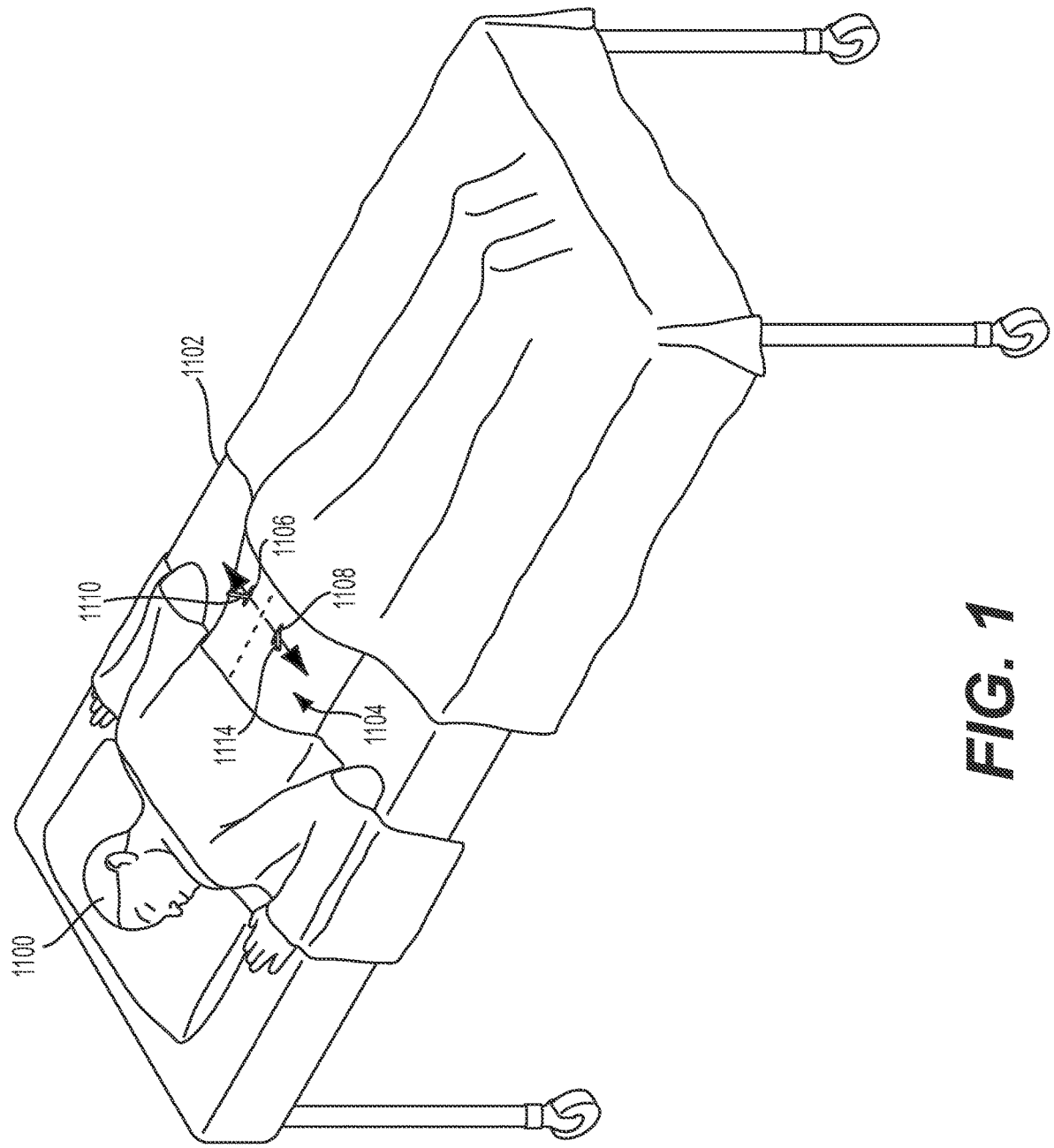
FIG. 1 is a schematic diagram illustrating an isometric view of an embodiment of a patient undergoing surgery.

FIG. 1 is an isometric view of an embodiment of patient 1100 on operating table 1102. In this embodiment, patient 1100 is experiencing a surgical procedure to insert a spinal prosthesis. In particular, back 1104 of patient 1100 may have a first incision 1106 and second incision 1108. In an embodiment, first incision 1106 includes first tube 1110 and second incision 1108 includes second tube 1114. First incision 1106 and second incision 1108 may both be less than one inch long. It should be understood that the placement of incisions 1106 and 1108 may be moved farther apart or closer together and the location of incisions 1106 and 1108 in the current embodiment is only meant to be exemplary.

Figure 2:
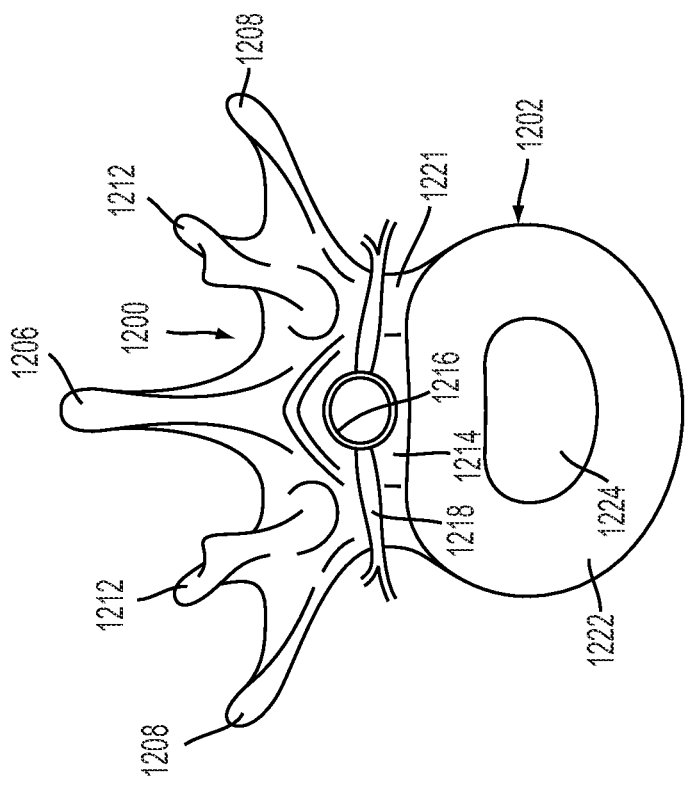
FIG. 2 is a schematic diagram illustrating a plan view of an embodiment of an intervertebral disc.

First tube 1110 and second tube 1114 may be inserted into an intervertebral disc disposed between two adjacent vertebrae. For the purposes of this application, "disc" and "disk" have the same meaning and may be used interchangeably. FIG. 2 is a plan view of a single vertebra, shown generally at 1200, and an associated intervertebral disc 1202. (The anatomy shown in FIG. 2 is generally that of a lumbar vertebra, although the anatomy of thoracic, lumbar, and cervical vertebrae is similar; therefore, FIG. 2 can be considered to illustrate the basic principles of thoracic, lumbar, and cervical vertebral anatomy.) The spinous process 1206 of the vertebra 1200 extends dorsally and can typically be palpated and felt through the skin of the back. Also in the dorsally-extending portion of the vertebra 1200 are two transverse processes 1208 and two mammillary processes and facet joints 1212. A spinal canal 1214 (i.e., an opening) is provided in the vertebra 1200. The spinal cord and nerves 1216 extend through the spinal canal 1214 such that the spinal cord 1216 receives the full protection of the bony, dorsally-located spinous, transverse, and mammillary processes and facet joints 1206, 1208, 1212. The vertebral body also protects the spinal cord and nerves 1216 ventrally. Periodically, nerves 1218 branch out from the spinal cord 1216 to innervate various areas of the body. The forward or ventral edge of the vertebral foramen 1221 is defined by the vertebral body (not shown in FIG. 2); a bony, generally elliptical shelf in front of which the intervertebral disc 1202 rests. FIG. 2 also illustrates the basic structure of the intervertebral disc 1202, including the annulus fibrosis 1222 and the nucleus pulposus 1224.

Figure 3:
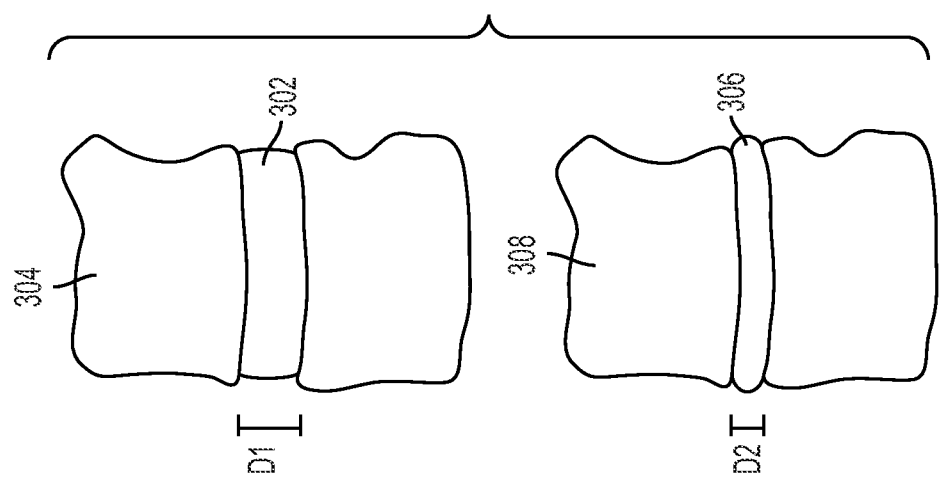
FIG. 3 is a schematic diagram illustrating an embodiment of a healthy intervertebral disc and an intervertebral disc that has degenerated.

In some cases, an intervertebral disc 1202 may degenerate over time, requiring the need for a spinal disc implant. FIG. 3 illustrates an example of degeneration. As shown, healthy intervertebral disc 302 is disposed between vertebrae 304. In this case, vertebrae 304 are separated by a distance D1 because of support provided by disc 302. Also shown in FIG. 3 is unhealthy intervertebral disc 306, which is disposed between vertebrae 308. In this case, vertebrae 308 are separated by a distance D2 that is much smaller than distance D1 because of the degeneration of disc 306.

If an intervertebral disc has failed or degenerated, a typical correction is a surgical procedure to remove some of, or the entire, intervertebral disc. Following this removal, a spinal prosthesis may be inserted in order to facilitate fusion of the vertebrae adjacent to the failed intervertebral disc. According to present embodiments, surgery may be performed in a manner that limits the size of the incisions needed to insert prosthesis. Spinal prostheses according to the present embodiments may include provisions for easy insertion via a small incision in the back.

In some cases, a vertebral body could also be fully or partially replaced using a spinal prosthesis. The following detailed description refers to the replacement of an intervertebral disc; however in other embodiments these same principles could be applied to a spinal prosthesis configured to replace a vertebral body.

Figure 4:
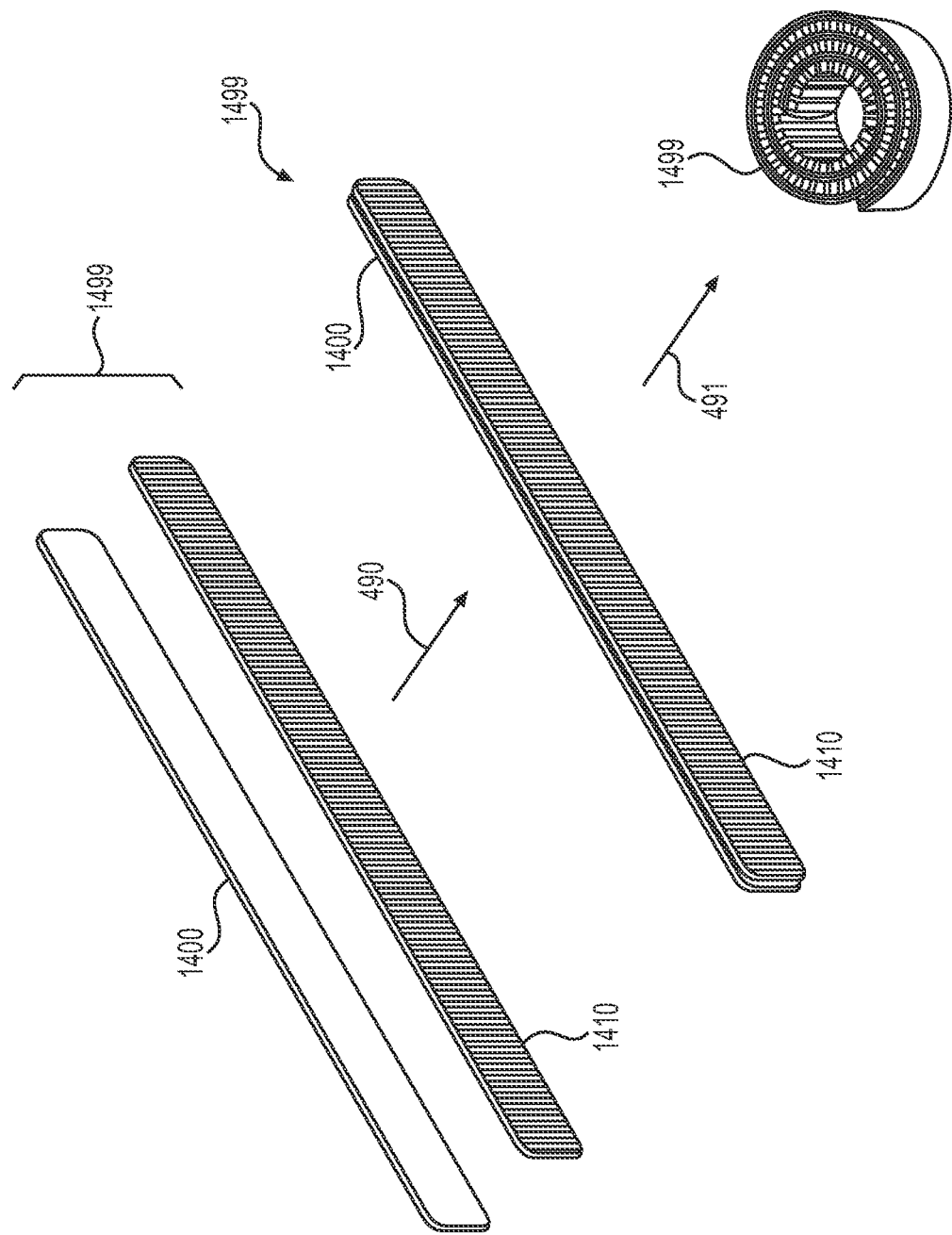
FIG. 4 is a schematic diagram illustrating an embodiment of a coiling implantable prosthesis.

In light of the desire for minimally invasive procedures, embodiments include provisions for insertion of a spinal fusion implant into a surgical site starting from a substantially linear configuration and transforming to a substantially nonlinear configuration within the surgical site. The nonlinear configuration may be, for example, curved or coiled, and may substantially fill a surgical site to provide desired structural support, such as spinal columnar support. FIG. 4 illustrates an embodiment of an implantable prosthesis 1499, which may include a biased coiling member 1400 and a conforming coiling member 1410, starting in a substantially linear configuration.

As used herein, the term "coil" refers generally to movement into a nonlinear configuration, and encompasses curving movement before and after concentric rings may be formed. In other words, a biased coiling member, for example, may coil to a curved shape before it coils enough to form a concentric ring, and may continue to coil after it forms a concentric ring to form additional concentric rings. Thus, a length of coiling member may dictate whether the coiling member coils to a curved configuration without concentric rings or to a configuration with concentric rings. In the present embodiments, the term "coil" should therefore be considered broadly applicable to any curving toward a coil shape, whether concentric rings are formed or not.

As shown in FIG. 4, in embodiments, the biased coiling member 1400 may be mated with the conforming coiling member 1410 as represented by the arrow 490. The mated members 1400, 1410, while in a substantially linear configuration, may be inserted through an opening to a surgical site, for example, through a cannula inserted through the opening. The biased coiling member 1400 may then be allowed to curve or coil the conforming coiling member 1410 into the implantable prosthesis 1499, as represented by the arrow 491. The mated members 1400, 1410 may curve or coil within the surgical site and assume a final desired shape, such as the coiled shape shown in FIG. 4, or another curved shape (e.g., crescent shaped), embodiments of which are described in more detail below.

As shown in FIG. 4, the biased coiling member 1400 may be an elongated strip biased to coil, such as a metal constant force coil spring. The conforming coiling member 1410 may be configured to curve or coil under the force of the biased coiling member 1400, and to provide a desired structure to the implantable prosthesis 1499, for example, in terms of the width or height of the implantable prosthesis 1499. Although FIG. 4 illustrates conforming coiling member 1410 as an elongated, relatively thin continuous strip, conforming coiling member 1410 may also be thicker/wider and formed by connected or separate segments, which may provide a wider curve or coil in the implantable prosthesis 1499 using members 1400, 1410 of shorter lengths, as described in more detail in embodiments below.

FIGS. 5.1-5.3 illustrate an embodiment of a biased coiling member 1400. Generally, biased coiling member 1400 may be a long thin strip. Biased coiling member 1400 may have a length L1 much greater than a width W1. Additionally, the thickness T1 of biased coiling member 1400 may be small compared to both the length and the width of biased coiling member 1400. In some embodiments, length L1 may be between 1 cm and 100 cm. In some embodiments, width W1 may be between 2 mm and 30 mm. In some embodiments, thickness T1 may be between 0.01 mm and 3 mm. It should be understood that if a vertebral body is being replaced, the dimensions of biased coiling member 1400 may be much larger than the values discussed here.

Biased coiling member 1400 may have a relatively small profile, for convenient insertion into smaller incisions, such as those shown in FIG. 1. However, to provide adequate support to the adjacent vertebrae, biased coiling member 1400 may be packed tightly into intervertebral disc 1202. In some embodiments, the packing of biased coiling member 1400 may be tight or loose depending upon mechanical properties of biased coiling member 1400. For this reason, biased coiling member 1400 may include provisions for conforming to a packed shape once it has been inserted into intervertebral disc 1202.

Generally, biased coiling member 1400 may be constructed of a material including metal. In some embodiments, biased coiling member 1400 may be a shape memory alloy. In some embodiments, biased coiling member 1400 may be made of titanium or a titanium alloy. In other embodiments, biased coiling member 1400 may comprise a combination of one or more materials including, but not limited to, stainless steel, nitinol, polymers, biological matrices, ceramics, or any biocompatible material.

In embodiments discussed herein, a biased coiling member may coil a conforming coiling member and control the implanted shape of an implantable prosthesis. A biased coiling member may be made of a spring hardened metal, such as, but not limited to, titanium, titanium alloy, or stainless steel, or alternatively, may be formed from a polymer.

In some cases, biased coiling member 1400 may be a coiling spring formed from a stainless steel alloy. This arrangement may be useful because such alloys have low fatigue and high strength. Additionally, these alloys may have a high return force. Additionally, using a stainless steel alloy may allow for increased corrosion resistance.

Biased coiling member 1400 may include provisions for changing shape. In some embodiments, biased coiling member 1400 may be manufactured at an elevated temperature with a first shape. Following this, biased coiling member 1400 may be cooled and formed into a second shape. Finally, as biased coiling member 1400 is placed in temperature ranges of 90-100 degrees Fahrenheit, it may revert back to the first shape. In an embodiment, the first shape is a spiral coil and the second shape is a long rectangular strip.

In some embodiments, biased coiling member 1400 may include provisions for promoting bone growth, once it has been inserted into the intervertebral disc region. In some embodiments, biased coiling member 1400 may include a bone growth promoting agent. In an embodiment, biased coiling member 1400 may include bone growth promoting agent 1402 disposed along the entirety of its length. FIG. 5.2 is a cross-sectional view of biased coiling member 1400 with bone growth promoting agent 1402 disposed along its entire outer surface 1401.

In some embodiments, bone growth promoting agent 1402 may be selectively applied to one or more portions of biased coiling member 1400 or may not be applied at all. In an embodiment, as shown in FIG. 5.3, bone growth promoting agent 1402 may be applied to top surface 1403 of outer surface 1401. Likewise, bone growth promoting agent 1402 may also be applied to bottom surface 1405 of outer surface 1401. Bone growth promoting agent 1401 may also be applied in other desired locations or patterns, including on isolated or partial areas, such as (referring to FIG. 5.3) partially down the sides on the inside and outside, near the top and bottom. Generally, any type of bone growth promoting agent may be applied and in any pattern. Methods for selectively applying bone growth promoting agents, as well as examples of suitable types of bone growth promoting agents, have been previously disclosed in U.S. Pat. No. 8,241,357 to Bhatnagar et al., issued Aug. 14, 2012, entitled "Prosthesis with a Selectively Applied Bone Growth Promoting Agent," the entirety of which is herein incorporated by reference.

As described above in reference to FIG. 4, in embodiments of implantable prostheses, a biased coiling member may be mated with a conforming coiling member, such that the biased coiling members curves or coils the conforming coiling member, and the biased coiling member and the conforming coiling member coil together to form an implantable prosthesis. The conforming coiling member may help define the shape of an implantable prosthesis and may provide further structural support, for example, in providing additional bearing surfaces or in providing areas in which bone ingrowth may occur.

FIGS. 6.1-6.4 illustrate embodiments of a conforming coiling member 1410. As one embodiment, FIGS. 6.1-6.2 illustrate a conforming coiling member 1410A. Similar to the biased coiling member 1400, conforming coiling member 1410A may generally be a long thin strip having a length L2 much greater than a width W2. Additionally, the thickness T2 of conforming coiling member 1410A may be small compared to both the length and the width of conforming coiling member 1410A. In some embodiments, length L2 of conforming coiling member 1410A may be between 1 cm and 100 cm. In some embodiments, width W2 of conforming coiling member 1410A may be between 2 mm and 30 mm. In some embodiments, thickness T2 of conforming coiling member 1410A may be between 0.01 mm and 5 mm, and may vary along the length L2 to enable proper coiling and to achieve a desired shape and dimension when coiled, as described in further detail below. It should be understood that if a vertebral body is being replaced, the dimensions of conforming coiling member 1410A may be much larger than the values discussed here.

In another embodiment, FIGS. 6.3-6.4 illustrate a conforming coiling member 1410B, which may be formed from segments 1413 having a thickness T2 significantly greater than a thickness of a strip-type conforming coiling member, such as conforming coiling member 1410A of FIGS. 6.1-6.2. That greater thickness may enable the length L2 of conforming coiling member 1410B to be significantly shorter than a length of a strip-type conforming coiling member, since the greater thickness provides a larger bearing surface when the conforming coiling member 1410B is curved. In such a case, the biased coiling member 1400 mated with the conforming coiling member 1410B may have a shorter length (e.g., L1 of biased coiling member 1400 of FIG. 5.1 may be shorter) that is substantially equal to the length L2 of the conforming coiling member 14108. In other embodiments, the biased coiling member 1400 may have a length that is shorter or longer than the length of the conforming coiling member 1410B. In any case, the greater thickness of the conforming coiling member 14108 may enable the implantable prosthesis to provide an adequate bearing surface when the biased coiling member and the conforming coiling member are curved into a nonlinear configuration that is not necessarily fully coiled, for example, in a crescent-shaped configuration, as described in more detail below. In some embodiments, length L2 of conforming coiling member 1410B may be between 1 cm and 10 cm. In some embodiments, width W2 of conforming coiling member 1410B may be between 2 mm and 20 mm. In some embodiments, thickness T2 of conforming coiling member

1410B may be between 2 mm and 20 mm. It should be understood that if a vertebral body is being replaced, the dimensions of conforming coiling member 1410B may be much larger than the values discussed here As shown in FIGS. 6.3-6.4, segments 1413 of conforming coiling member 1410B may be separate from each other, in which case the segments 1413 may be held in position relative to each other by attachment to a biased coiling member. In other embodiments, segments 1413 may be connected to each other by flexible or pivoting connections, for example, by hinged connections that allow the segments 1413 to pivot with respect to each other and for the entire conforming coiling member 1410B to curve or coil.

In embodiments, a conforming coiling member, such as conforming coiling member 1410A, may be a strip formed from PEEK (polyether ether ketone), PEKK (polyetherketoneketone), PLLA (polylactide), or any implantable-grade polymer, and may be configured to be coupled to a biased coiling member, for example, by fasteners, or by a groove or slot formed along the length of the conforming coiling member, which receives the biased coiling member. In other embodiments, a conforming coiling member, such as conforming coiling member 1410B, may be segments formed of an implantable-grade polymer, metal, ceramic, carbon fiber, or composite materials. In embodiments, a conforming coiling member may bear most of the loads during a fusion process, and the biased coiling member may provide the final coil or curved form and add strength by ensuring resistance to permanent deformation of the conforming coiling member, and a consistent implant diameter.

The lengths L1, L2 and widths W1, W2 of biased coiling member 1400 and conforming coiling member 1410 may be substantially equal. However, the lengths L1, L2 and widths W1, W2 may differ to accommodate desired deployment and implantation configurations and to provide desired structural features of a coiled implanted prosthesis. For example, the length L1 of the biased coiling member 1400 may be longer than the length L2 of the conforming coiling member 1410 to provide a leading, proximal portion of the biased coiling member 1400 that may be connected to a deployment device, allowing only the biased coiling member 1400 (and not the conforming coiling member 1410) to be connected to the deployment device. As another example, the width W1 of the biased coiling member 1400 and the width W2 of the conforming coiling member 1410 may be different to provide gaps between upper and lower edges of the members 1400 and 1410 when they are in the coiled configuration, so as to provide different bearing surfaces or areas in which bone growth promoting agent may be placed and in which bone ingrowth may occur. In some embodiments, a biased coiling member 1400 made of a material (e.g., metal) more rigid than a conforming coiling member 1410 may have a width W1 greater than a width W2 of the conforming coiling member 1410 so as to provide a more rigid attachment to, and support across, two opposing vertebrae. In other embodiments, a conforming coiling member 1410 made of a more flexible material (e.g., PEEK) may have a width W2 greater than a width W1 of the biased coiling member 1400 so as to provide a more flexible attachment between opposing vertebrae, which may be more compatible with vertebrae in terms of hardness, density, and other structural characteristics. In still other embodiments, widths W1, W2 may be equal to provide, when in a coiled configuration, a substantially planar bearing surface for each of the vertebrae.

Figure 7:
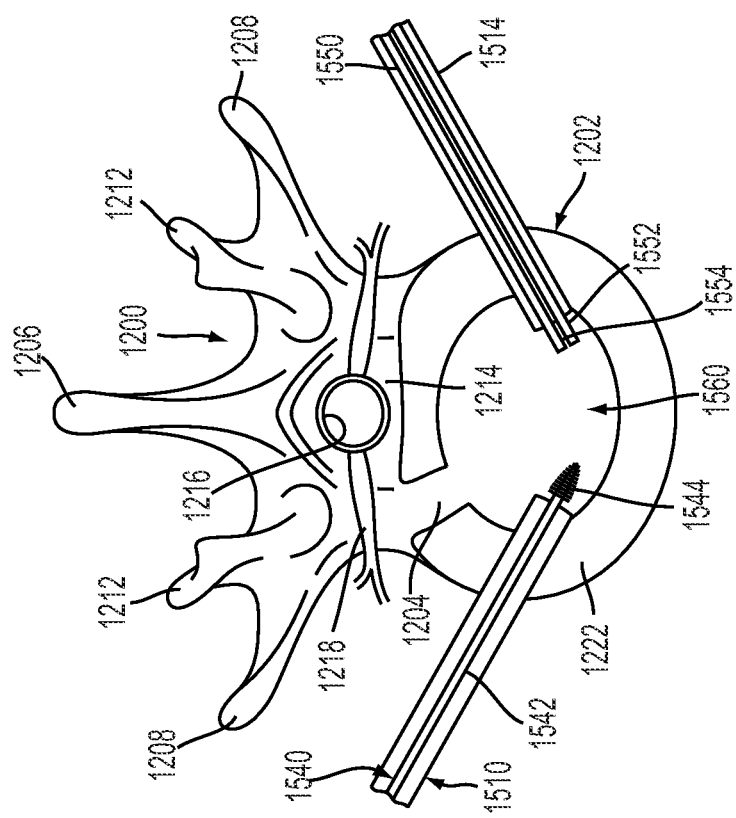
FIG. 7 is a schematic diagram illustrating a plan view of an embodiment of a surgical tool and a dual catheter being inserted into an intervertebral cavity.
Figure 8:
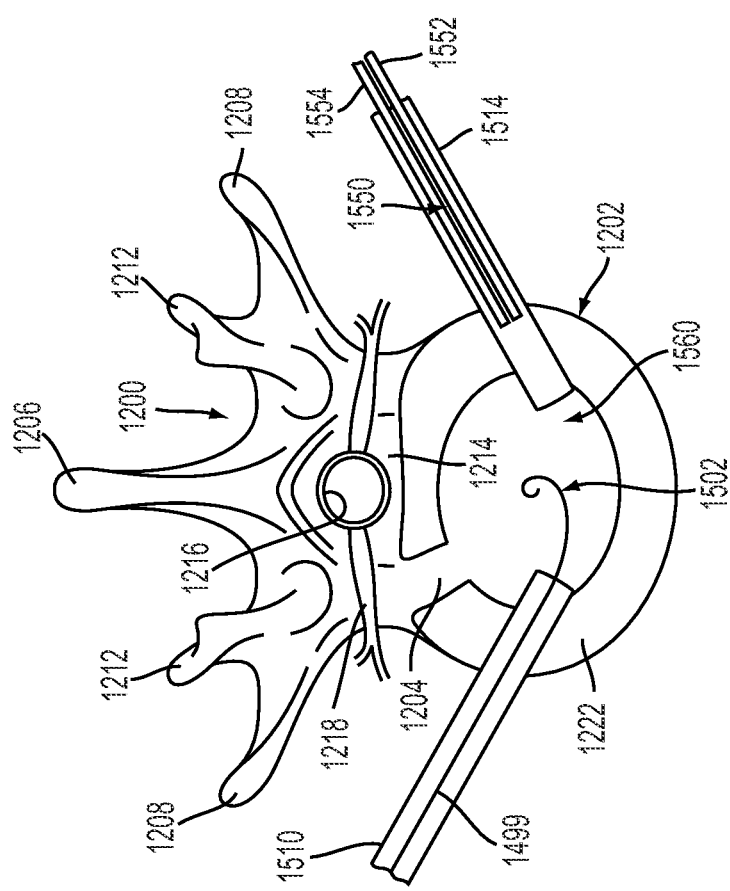
FIG. 8 is a schematic diagram illustrating a plan view of an embodiment of a coiling implantable prosthesis being inserted into an intervertebral cavity.
Figure 9:
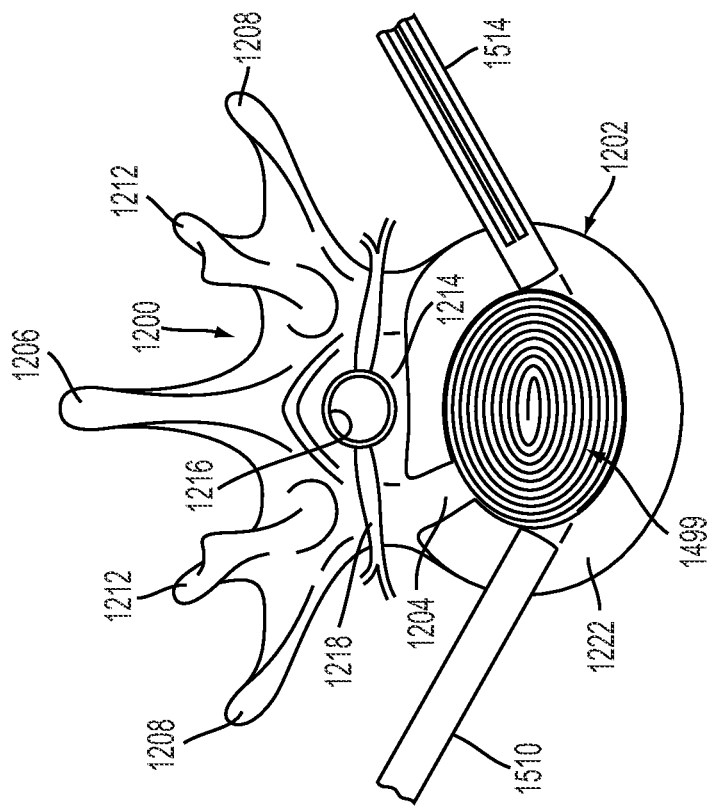
FIG. 9 is a schematic diagram illustrating a plan view of an embodiment of a coiling implantable prosthesis fully inserted into an intervertebral cavity.

FIGS. 7-9 illustrate an embodiment of a surgical procedure used to insert a coiling implantable prosthesis. The following embodiment comprises steps for inserting a spinal prosthesis using two tubes; however it should be understood that in other embodiments, a single tube may be used for discectomy and/or implantation. In this case, any parallel steps involving the use of two tubes simultaneously could be performed sequentially with a single tube. In particular, steps using a camera and/or light inserted through one tube and a spinal tool through a second tube may be accomplished by using a single tube incorporating a light and/or camera at the periphery of the tube or just outside of the tube.

In a first step, first tube 1510 and second tube 1514 may be inserted into intervertebral disc 1202. Generally, one tube may be used for a surgical tool, while the second tube may be simultaneously used to insert a fiber optic camera into one of the incisions to give the surgeon a clear view of the intervertebral disc region. In some embodiments, each of the first tube 1510 and second tube 1514 may be a cannula. The cross-sectional shape of tubes 1510 and 1514 may be any shape, including oval-like, circular, or otherwise round, as well as hexagonal or any polygonal shape.

Following the insertion of first tube 1510 and second tube 1514, a series of instruments may be used to remove portions of intervertebral disc 1202 and score the endplates. In some embodiments, first surgical device 1540 may be inserted into first tube 1510. First surgical device 1540 may be a brush, burr, rasp, or a shaver. In an embodiment, first surgical device 1540 may include flexible shaft 1542 and wire brush tip 1544. Wire brush tip 1544 may spin, removing portions of intervertebral disc 1202.

In some embodiments, dual catheter 1550 may be inserted into second tube 1514. Dual catheter 1550 may include first channel 1552 and second channel 1554. In some embodiments, first channel 1552 may include a fiber optic camera. With this configuration, the surgery may be visualized by the surgeon using the fiber optic camera. Additionally, second channel 1554 may be configured to inject water and/or provide a vacuum for removing debris. With this configuration, second channel 1554 may be used to clean out cavity 1560, which is created as a portion of intervertebral disc 1202 is removed. Once the necessary portions of intervertebral disc 1202 have been removed, first surgical device 1540 may be removed from first tube 1510.

Referring to FIGS. 8-9, coiling implantable prosthesis 1499 (which may include a biased coiling member mated with a conforming coiling member) may be inserted into cavity 1560 once a portion of intervertebral disc 1202 has been removed. As previously discussed, coiling implantable prosthesis 1499 may include a biased coiling member 1400 having a material structure that allows it to change shape following insertion into cavity 1560. In an embodiment, biased coiling member 1400 may be configured to coil as it is exposed to temperatures between 90 and 100 degrees Fahrenheit. In other embodiments, biased coiling member 1400 may coil due to non-temperature dependent memory, such as occurs with a measuring tape. This could be achieved using a metal, polymer, ceramic, carbon fiber, or composite material biased coiling member, for example.

As shown in FIG. 8, first portion 1502 of coiling implantable prosthesis 1499 has started to coil as it is inserted into cavity 1560. As an additional portion of coiling implantable prosthesis 1499 is inserted through first tube 1510 and into cavity 1560, the additional portion may deform and coil as well. In an embodiment, coiling implantable prosthesis 1499 may be sized and structured so that as the coiling implantable prosthesis 1499 is inserted into the cavity 1560 it coils around itself, as shown in FIG. 9. Alternatively, the implantable prosthesis 1499 may be sized and structured so that the coiling implantable prosthesis 1499 coils to a curved configuration (e.g., crescent-shaped) that is not coiled around itself, embodiments of which are described in more detail below.

Generally, a coiling implantable prosthesis 1499 (including a biased coiling member and conforming coiling member) may be configured to fill cavity 1560 of intervertebral disc 1202 completely. For illustrative purposes, coiling implantable prosthesis 1499 is shown in FIG. 9 coiled with large gaps between adjacent portions. However, in some embodiments, coiling implantable prosthesis 1499 may coil tightly so that no gaps are seen. In an embodiment, coiling implantable prosthesis 1499 may coil loosely to provide space or gaps between adjacent, radially spaced coils. This arrangement may help to facilitate bone growth to occur between the coils.

In an alternative embodiment, multiple implantable prostheses may be used. Each implantable prosthesis may include a coiled or nonlinear shape, as described above. In some embodiments, each of the implantable prostheses may be disposed against one another. In some embodiments, each of the implantable prostheses may be associated with different heights or angled surfaces in order to create lordosis.

Figure 10:
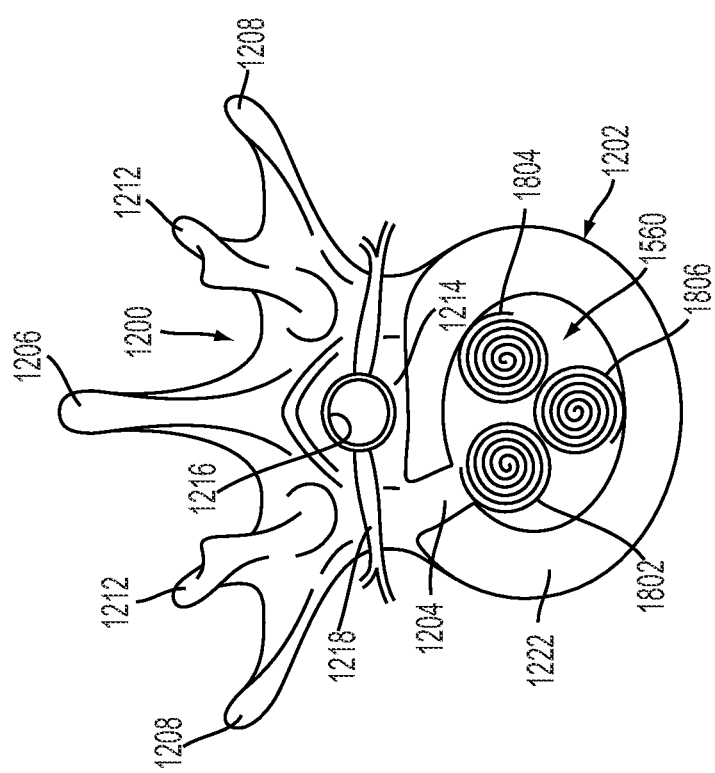
FIG. 10 is a schematic diagram illustrating a plan view of an embodiment of three coiling implantable prostheses inserted into an intervertebral cavity.

FIG. 10 illustrates an embodiment in which multiple implantable prostheses are inserted within cavity 1560. In this embodiment, first prosthesis 1802, second prosthesis 1804, and third prosthesis 1806 have been inserted into cavity 1560. Each of the prostheses 1802, 1804, and 1806 may be inserted in an identical manner to the method described above in reference to FIGS. 6-8. Generally, any number of prostheses may be inserted into cavity 1560.

A biased coiling member of each of the prostheses 1802, 1804, and 1806 may be constructed of a shape memory alloy. In some embodiments, the shape memory alloy may be a nickel titanium alloy. In other embodiments, a biased coiling member of the prostheses 1802, 1804, and 1806 may comprise a combination of one or more materials including, but not limited to, stainless steel, nitinol, polymers, biological matrices, ceramics, or any biocompatible material. In an embodiment, a biased coiling member of prostheses 1802, 1804, and 1806 may be made of a material including titanium.

Embodiments may include provisions for attaching a conforming coiling member (such as conforming coiling member 1410 of FIG. 4) to a biased coiling member (such as biased coiling member 1400 of FIG. 4), and for facilitating the coiling or curving of the conforming coiling member, while also allowing the conforming coiling member to provide a desired width and diameter to an implantable prosthesis and to provide vertical structural support between vertebrae.

Figure 11:
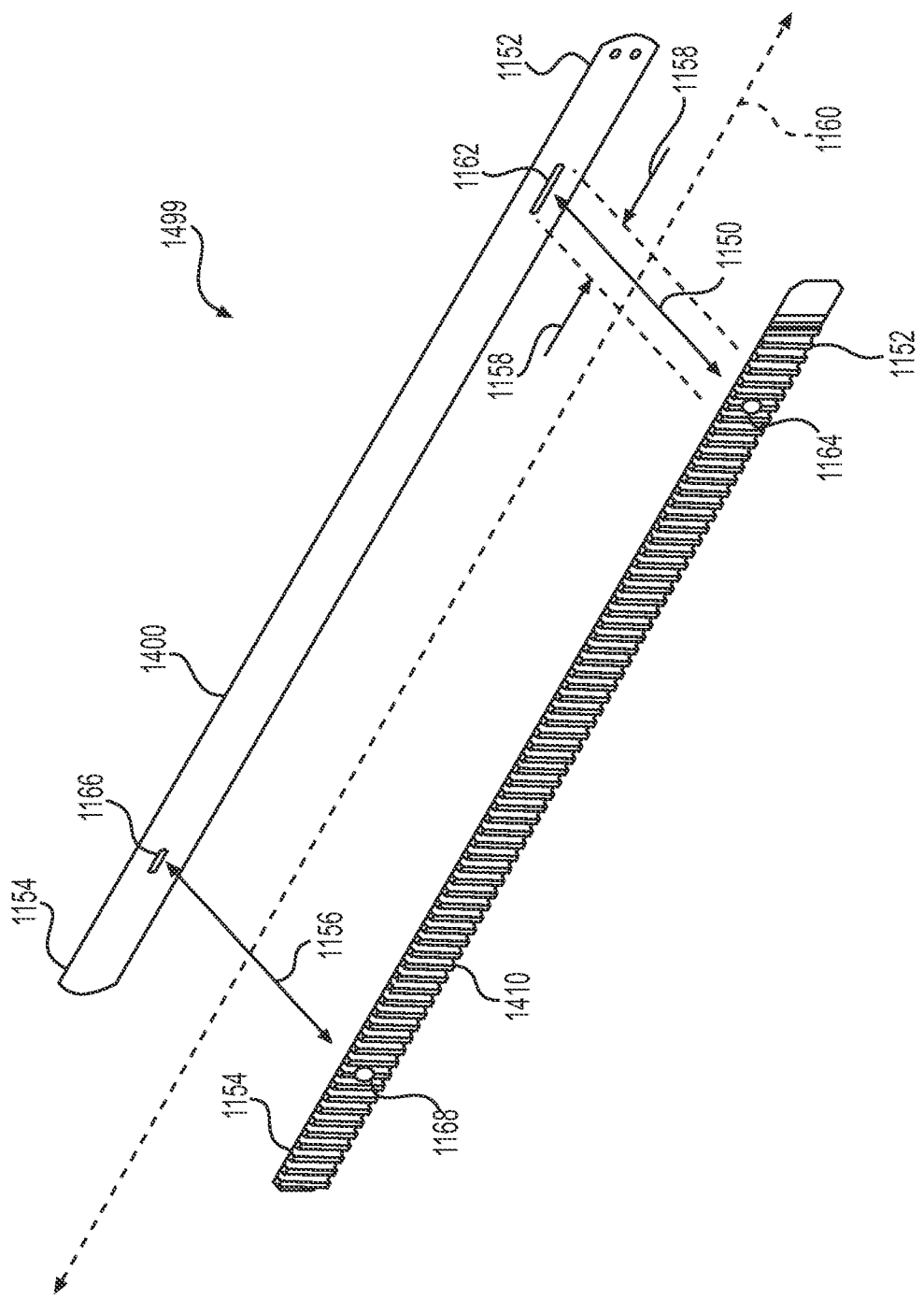
FIG. 11 is a schematic diagram illustrating an embodiment of provisions for connecting a biased coiling member to a conforming coiling member of an implantable prosthesis.

FIG. 11 illustrates an embodiment of provisions for connecting a biased coiling member 1400 to a conforming coiling member 1410 of an implantable prosthesis 1499. As shown, implantable prosthesis 1499 may include a first fastener assembly as represented by the arrow 1150, disposed on a proximal portion 1152 of the biased coiling member 1400 and conforming coiling member 1410, and a second fastener assembly as represented by the arrow 1156 on a distal portion 1154 of the biased coiling member 1400 and conforming coiling member 1410. As used herein, proximal and distal refer to positions relative to a position of a user implanting the implantable prosthesis 1499, such as a surgeon implanting the implantable prosthesis 1499 through a cannula.

In connecting a biased coiling member and a conforming coiling member, embodiments may include provisions for engaging the members and constraining most relative movement between the members, except for relative movement along the length of the implantable prosthesis as represented by the longitudinal axis 1160 in FIG. 11. That relative longitudinal movement may allow the biased coiling member and conforming coiling member to move longitudinally independently (e.g., sliding against each other), to allow a transition from a linear configuration to a nonlinear configuration (e.g., coiled or curved). In embodiments, first fastener assembly 1150 may allow a relative displacement 1158 larger than a relative displacement allowed by second fastener assembly 1156, to accommodate the greater relative movement of the biased coiling member and conforming coiling member at the proximal portion 1152 where there may be coils having larger radii of curvature. The second fastener assembly 1156 may allow a relative displacement less than relative displacement 1158 or may be a single point of connection with no relative displacement, since only a minimal relative displacement may be needed between the biased coiling member and conforming coiling member at the distal portion 1154, where the members 1400, 1410 first coil and have a smaller radii of curvature. Second fastener assembly 1156 may serve to avoid too much relative displacement between members 1400, 1410, and keep the members 1400, 1410 securely fastened to each other when the implantable prosthesis 1499 is in either the linear deployment configuration or the nonlinear implanted configuration. Together, the first fastener assembly 1150 and the second fastener assembly 1156 may keep the biased coiling member 1400 mated with the conforming coiling member 1410 in a direction generally lateral to the longitudinal axis 1160, while allowing varying relative displacements along the longitudinal axis 1160 to accommodate the different relative displacements needed along the length of the implantable prosthesis 1499 to allow the implantable prosthesis 1499 to coil properly.

To provide relative displacement, in embodiments, a first fastener assembly 1150 or second fastener assembly 1156 may include a longitudinally variable connection on either of the biased coiling member and the conforming coiling member, and a longitudinally fixed connection on the other of the biased coiling member and conforming coiling member. As shown in FIG. 11, in an embodiment, a first fastener assembly 1150 may comprise a longitudinal slot 1162 on biased coiling member 1400 and a fixed connector 1164 on conforming coiling member 1410. Fixed connector 1164 may include a protrusion, such as a pin that extends laterally through slot 1162. In other embodiments, a fixed connector may be an opening in conforming coiling member 1410 aligned with the slot 1162, with a separate member, such as a pin or rivet, extending through the opening and the slot 1162. Similarly, in an embodiment, a second fastener assembly 1156 may comprise a longitudinal slot 1166 on biased coiling member 1400 and a fixed connector 1168 on conforming coiling member 1410. If no relative displacement is desired at second fastener assembly 1156, then, in an embodiment, second fastener assembly 1156 may comprise longitudinally fixed connectors on both the biased coiling member 1400 and conforming coiling member 1410, such as a cylindrical protrusion on conforming coiling member 1410 aligned with a correspondingly sized circular opening in biased coiling member 1400. Although FIG. 11 shows the longitudinally variable connections on the biased coiling member 1400 and the longitudinally fixed connections on the conforming coiling member 1410, those variable and fixed connections could be reversed between the biased coiling member 1400 and conforming coiling member 1410.

In addition, embodiments may use any combination of variable and fixed connections on the biased coiling member and conforming coiling member, including variable and fixed connections on a single member.

Embodiments may provide a biased coiling member configured to engage a conforming coiling member and allow sliding along the length during transition from a linear, flat configuration to a nonlinear, coiled configuration. A biased coiling member may be made of a shape memory material, such as but not limited to titanium, titanium alloy, stainless steel, nitinol, polymers, biological matrices, ceramics, or any biocompatible material, and may be deflected to the flat state for assembly, sterilization, and distribution, without permanent deformation. The width of nonlinear configuration may vary in manufacture to accommodate different anatomical needs for vertebral spacing.

FIGS. 12.1-12.11 illustrate an embodiment of an implantable prosthesis 1699 including a biased coiling member 1600 and conforming coiling member 1610, as well as provisions for engaging members 1600, 1610, while allowing relative movement between members 1600, 1610 along the longitudinal axis 1601 of the implantable prosthesis 1699. Biased coiling member 1600 may be a metal spring biasing coil. Conforming coiling member 1610 may be a flexible strip of polymer material. Although in FIG. 12.1 biased coiling member 1600 and conforming coiling member 1610 are substantially equal in lateral width, conforming coiling member 1610 may be slightly wider than the biased coiling member 1600, for example, so that the conforming coiling member 1610 provides a substantially larger planar bearing surface for each of the vertebrae to contact.

As described above in reference to FIG. 11, implantable prosthesis 1699 may include provisions for holding the biased coiling member 1600 and the conforming coiling member 1610 laterally together, but allowing in a longitudinal direction a limited relative movement with respect to each other. In embodiments, as shown best in FIG. 12.2, biased coiling member 1600 may define fastener openings 1607, 1608 (e.g., holes, recesses, or slots) configured to receive mechanical fasteners such as shoulder rivets, clevis pinned connections, or other laterally protruding fasteners, to facilitate a connection that has one direction of limited freedom of movement along the length of the biased coiling member 1600 and conforming coiling member 1610. Fastener openings 1608 may be formed, for example, by drilling, punching, or ablating. As shown, biased coiling member 1600 may have a first fastener opening 1607 at a proximal portion 1152 of the biased coiling member 1600 and a second fastener opening 1608 at a distal portion 1154 of the biased coiling member 1600.

In cooperation with the openings 1607, 1608 of the biased coiling member 1600, the conforming coiling member 1610 may have a first opening 1620 at a proximal portion of the conforming coiling member 1610 and a second opening 1622 at a distal portion of the conforming coiling member 1610. First opening 1620 and second opening 1622 may be elongated in a longitudinal direction (e.g., in an oblong, oval, or slot shape), to allow longitudinal relative movement between the biased coiling member 1600 and the conforming coiling member 1610. In an embodiment, the first opening 1620 may have a longer longitudinal dimension than the second opening 1622, since more relative displacement between the biased coiling member 1600 and conforming coiling member 1601 may be needed at the proximal portion of the implantable prosthesis 1699, which is disposed on the outside of the coil at a larger radius of curvature when the implantable prosthesis is in a coiled configuration.

As shown in FIGS. 12.1, 12.3-12.5, and 12.8-12.11, implantable prosthesis 1699 may have a first fastener 1624 disposed in the first fastener opening 1607 at the proximal portion 1152 of the biased coiling member 1600 and in the first opening 1620 of the conforming coiling member 1610. Implantable prosthesis 1699 may further have a second fastener 1626 disposed in the second fastener opening 1608 at the distal portion 1154 of the biased coiling member 1600 and in the second opening 1622 of the conforming coiling member 1610. As shown in FIGS. 12.3 and 12.9-12.11, first fastener 1624 may be substantially fixed with respect to the biased coiling member 1600, while allowing the conforming coiling member 1610 to move longitudinally relative to the biased coiling member 1600 the length of the first opening 1620. As shown in FIGS. 12.6, 12.10, and 12.11, first fastener 1624 may include a shoulder 1628 that slides within first opening 1620 and occupies substantially the entire lateral width of the first opening 1620. As shown in FIGS. 12.4 and 12.8, second fastener 1626 may be substantially fixed with respect to the biased coiling member 1600 and the conforming coiling member 1610, substantially preventing relative longitudinal displacement between the conforming coiling member 1610 and the biased coiling member 1600, but allowing a coiling motion due to a curved or tapered edge face on a shoulder 1636 of the second fastener 1626. In other embodiments, the length of second opening 1622 may be longer than shown in the figures, so that the second fastener 1626 may be substantially fixed with respect to the biased coiling member 1600, while allowing the conforming coiling member 1610 to move longitudinally relative to the biased coiling member 1600 the length of the longer second opening 1622, which may be less than the longitudinal relative movement allowed by the first opening 1620. Embodiments may use any combination of fixed and variable connections and relative lengths of longitudinal displacement as suitable for a particular implementation, for example, second opening 1622 may be shorter, equal to, or longer than first opening 1620.

FIG. 12.6 illustrates an embodiment of the first fastener 1624 in isolation. As shown, first fastener 1624 may have the form of generally a shoulder rivet, with a head 1630, a solid shoulder 1628 disposed adjacent to the head 1630, and a shank 1632 on a side of the first fastener 1624 opposite to the head 1630. As shown, for example, in the cross-sectional view of FIG. 12.9, the head 1630 may be disposed on the inside face (i.e., a face facing toward the interior of the coiled implantable prosthesis) of the conforming coiling member 1610, with portions of the head 1630 overhanging the first opening 1620. The shoulder 1628 may be slidably disposed within the first opening 1620. The shank 1632 may be disposed through the fastener opening 1607 of the biased coiling member 1600 and extend to above an outside face of the biased coiling member 1600. FIGS. 12.5, 12.6, 12.9, and 12.10 show the first fastener 1624 with a straight shank 1632 before the shank 1632 is formed to secure the first fastener 1624 over the outside face of the biased coiling member 1600. FIG. 12.11 shows the shank 1632 after it has been formed, for example, by impacting or compressing the shank 1632 into a desired shape that overhangs the first opening 1620, thereby securing the first fastener 1624 to the biased coiling member 1600 and the conforming coiling member 1610. In forming the shank 1632, shoulder 1628 may serve as a bearing surface. The first fastener 1624 may be made of, for example, a biocompatible malleable metal, such as stainless steel or titanium, or a biocompatible malleable and formable polymer, or any biocompatible malleable or formable material.

FIG. 12.7 illustrates an embodiment of the second fastener 1626 in isolation. As shown, similar to the first fastener 1624, second fastener 1626 may have the form of generally a shoulder rivet, with a head 1634, a solid shoulder 1636 disposed under the head 1634, and a shank 1638 on a side of the second fastener 1626 opposite to the head 1634. As shown, for example, in the cross-sectional view of FIG. 12.8, the head 1634 may be disposed on the inside face (i.e., a face facing toward the interior of the coiled implantable prosthesis) of the conforming coiling member 1610, with portions of the head 1634 overhanging the second opening 1622. The shoulder 1636 may be slidably disposed within the second opening 1622. Alternatively, the second opening 1622 may be sized substantially equal to the shoulder 1636 such that the shoulder 1636 is substantially fixed and not slidable. The shank 1638 may be disposed through the fastener opening 1608 of the biased coiling member 1600 and extend to above an outside face of the biased coiling member 1600. FIGS. 12.5, 12.7, and 12.8 show the second fastener 1626 with a straight shank 1638 before the shank 1638 is formed to secure the second fastener 1626 over the outside face of the biased coiling member 1600. Second fastener 1626 may be formed in the same manner described above for first fastener 1624, as shown in the embodiment of FIG. 12.11. The second fastener 1626 may be formed, for example, by impacting or compressing the shank 1638 into a desired shape that overhangs the second opening 1622, thereby securing the second fastener 1626 to the biased coiling member 1600 and the conforming coiling member 1610. In forming the shank 1638, shoulder 1636 may serve as a bearing surface. The second fastener 1626 may be made of, for example, a biocompatible malleable metal, such as stainless steel or titanium, or a biocompatible malleable and formable polymer, or any biocompatible malleable or formable material.

As shown in FIGS. 12.1, 12.3, 12.4, and 12.8-11, in embodiments, conforming coiling member 1610 may include a plurality of ribs 1615 spanning the lateral width of conforming coiling member 1610. The plurality of ribs 1615 may be manufactured in varying heights to change the diameter of the implantable prosthesis 1699. At a proximal portion of the conforming coiling member 1610, conforming coiling member 1610 may include a tapered end 1618 in which the heights of ribs 1615 decrease, which may facilitate a nearly round outside contour when in a coiled configuration. Conforming coiling member 1610 may have a thin flexible member 1611 between each rib 1615 to allow the conforming coiling member 1610 to substantially match the spiral of biased coiling member 1600. The gaps 1617 between ribs 1615 may be machined or molded. The gaps 1617 may facilitate coiling to conform to a biased coiling member, and may also allow for bone graft to engage in the gaps.

Upon engagement of the biased coiling member 1600 and conforming coiling member 1610, the natural state of the assembly may be to coil to a diameter determined by the height of the plurality of ribs 1615. By varying the height of ribs 1615 in production, different diameter coils can be produced with a common length biased coiling member. In addition, in embodiments, rounded or beveled outer surfaces 1613 of ribs 1615 may provide smoother passage over an edge of the opening of a cannula during deployment or provide smoother coiling if the ribs contact each other during coiling.

In embodiments, conforming coiling member 1610 may be manufactured by extruding a rectangular bar, and machining the gaps 1617 between ribs 1615 after the bar is cut to length.

An implantable prosthesis may also include provisions for attaching the implantable prosthesis to a deployment device, moving the implantable prosthesis into an implantation site, and controlling the transition of the implantable prosthesis from a linear configuration to a nonlinear configuration. In an embodiment, as shown in FIGS. 12.1-12.3, 12.5, and 12.9-12.11, biased coiling member 1600 may define instrument openings 1609 configured to receive a portion of a deployment device. FIG. 12.2 illustrates biased coiling member 1600 in a substantially natural state of coil, with openings 1607, 1608 configured to receive connecting features on a conforming coiling member. A deployment device may include hooks or other protruding tools or instruments that engage openings 1609 and may push and pull the biased coiling member 1600, for example, through a cannula. In one embodiment, with the implantable prosthesis 1699 in a nonlinear, coiled configuration, a deployment device may engage the openings 1609, which are disposed at the proximal portion 1152 of the implantable prosthesis 1699 and on the outside of the coiled implantable prosthesis 1699. With the implantable prosthesis 1699 engaged, the deployment device may pull the proximal portion 1152 of the biased coiling member 1600 into a narrow cannula, and in so doing, may uncoil the implantable prosthesis 1699, transitioning the implantable prosthesis 1699 from a nonlinear, coiled configuration to a linear configuration stored in the cannula, ready for deployment into a surgical site. Then, when the cannula is positioned adjacent to or within a surgical site, the deployment device may push, using its engagement with the openings 1609 of the biased coiling member 1600, the implantable prosthesis 1699 out of the cannula and into the surgical site, with the implantable prosthesis 1699 coiling or curving as it emerges from the cannula.

Although FIGS. 12.1-12.11 illustrate embodiments in which a limited longitudinal relative displacement is provided by the conforming coiling member (e.g., by longitudinally elongated openings on the conforming coiling member 1610), such configurations may be reversed so that the biased coiling member provides the longitudinal relative displacement. For example, as shown in FIG. 11, a biased coiling member may have elongated slot openings 1162, 1166. Accordingly, notwithstanding the particular benefits associated with the conforming coiling member providing the longitudinal relative displacement, the present embodiments should be considered broadly applicable to implantable prostheses that provide the longitudinal relative displacement using either or both of the biased coiling member and the conforming coiling member, including any combination of variable and fixed connections on one or both of the biased coiling member and conforming coiling member.

Embodiments may also provide different means for connecting a biased coiling member and conforming coiling member. For example, embodiments may use mechanical fasteners, adhesives, welding, sutures, or staples. In one embodiment, FIGS. 13.1-13.2 illustrate an implantable prosthesis 1799 having a conforming coiling member 1710 connected to a biased coiling member 1700 by means of tabs 1724, 1726 extending from the conforming coiling member 1710, which snap into slots 1720, 1722 in the biased coiling member 1700. FIG. 13.1 illustrates an isometric outside detail view of an assembly of the conforming coiling member 1710 movably connected to the biased coiling member 1700 at a proximal portion of the implantable prosthesis 1799. FIG. 13.2 illustrates an isometric outside detail view of an assembly of the conforming coiling member 1710 movably connected to the biased coiling member 1700 at a distal portion of the implantable prosthesis 1799.

As shown in FIG. 13.1, tab 1724 may engage slot 1720 at a proximal portion of the implantable prosthesis 1799. As shown in FIG. 13.2, tab 1726 may engage slot 1722 at a distal portion of the implantable prosthesis 1799. The conforming coiling member 1710 may be machined from a plate or bar of plastic. Tabs 1724, 1726 may be snapped into the respective slots 1720, 1722 in the biased coiling member 1700 while the biased coiling member 1700 is constrained in a flat state. Upon connection, the assembly may be controllably recoiled. As shown, slot 1720 at the proximal portion of the implantable prosthesis 1799 may be longer than slot 1722 at the distal portion of the implantable prosthesis 1799, to accommodate the different relative displacements between the biased coiling member 1700 and the conforming coiling member 1710 required at the proximal and distal portions for proper coiling.

A snap connection provided by tabs 1724, 1726 and slots 1720, 1722 may comprise an increased width area at the mid-point of a tab that extends from the outward facing thin flexible member. A tab may be designed to be just wide enough at the mid-point to deflect into an opening (e.g., slot 1720 or slot 1722) formed in the biased coiling member (e.g., biased coiling member 1700). The tab bridging members may be slightly narrower than the opening in the biased coiling member to accommodate the free sliding motion along the length of the openings of the biased coiling member. The length of the opening in a biased coiling member may limit the sliding distance to match the need according to a desired design.

The snap connection provided by tabs 1724, 1726 and slots 1720, 1722 may engage and constrain most relative movement, except sliding along the slot length during transition from coiled to flat. Fastening may be secured by opposing protrusions extending laterally from the offset bridging members gripping the outside edges of the mating slots in the biased coiling member.

FIG. 13.1 also illustrates another embodiment of a tapered rib height at a proximal portion of the implantable prosthesis 1799, and a difference in width between the biased coiling member 1700 and the conforming coiling member 1710, with the biased coiling member 1700 being slightly wider than the conforming coiling member 1710.

FIGS. 14.1-14.3 illustrate another embodiment for connecting a biased coiling member and conforming coiling member. As shown, an implantable prosthesis 1899 may include a biased coiling member 1800 attached to a conforming coiling member 1810 using a pin fastener 1826. With this configuration, a conforming coiling member 1810 may be machined from plate or bar plastic, with slots and holes configured to receive a fastener, e.g., a mechanical fastener having features similar to a clevis pin. In an embodiment, the biased coiling member 1800 may be constrained in the flat state and the conforming coiling member 1810 may be paired and aligned to receive a fastener 1826. With the fastener 1826 positioned in opening 1822 of the biased coiling member 1800 and in opening 1823 of the conforming coiling member 1810, a pin 1840 of the mechanical fastener 1826 may be inserted through a first hole 1844 of the conforming coiling member 1810, through an opening 1846 in the fastener body 1835, and into a second opposing hole 1848 in the conforming coiling member 1810. Pin fastener 1826, with its pin 1840 sized to fit in the perpendicular opening 1846 in the fastener body 1835, may be configured to allow ease of movement in coiling and uncoiling and sliding along the length of opening 1822 in the biased coiling member 1800 during transition from a coiled configuration to a flat configuration, and back to a coiled configuration.

As shown in FIGS. 14.1-14.2, pin fastener 1826, when nested in the openings 1822, 1823 of conforming coiling member 1810 and biased coiling member 1800, may engage members 1800, 1810 and constrain most relative movement, except sliding along the length of opening 1822 during transition from a coiled configuration to a flat configuration, and back to a coiled configuration. As shown in FIG. 14.3, head 1834 of fastener 1826 may be configured to slidably retain the biased coiling member 1800 by having a dimension larger than lateral width of the opening 1822 and thereby lightly contacting the outside surface of biased coiling member 1800 around the opening 1822.

The connection shown in FIGS. 14.1-14.3 may be repeated if more than one fastener is desired along the length of the implantable prosthesis 1899. The length of opening 1822 may be adjusted depending on the longitudinal location of the pin fastener 1826 on the implantable prosthesis 1899, for example, having a greater length for locations closer to the proximal portion of the implantable prosthesis 1899 and having a shorter length for locations closer to the distal portion of the implantable prosthesis 1899, which as described above, may allow the implantable prosthesis 1899 to coil properly.

FIGS. 15.1-16.5 illustrate embodiments for inserting a coiling implantable prosthesis, such as the implantable prosthesis embodiments shown in FIGS. 12.1-14.3, into a surgical site. FIGS. 15.1-15.4 illustrate an embodiment for delivering an implantable prosthesis as an interbody fusion device using a minimally invasive surgery technique via a transforaminal lumbar interbody fusion (TLIF) approach. FIGS. 16.1-16.5 illustrate an embodiment for delivering an implantable prosthesis as an interbody fusion device using a minimally invasive surgery technique via a lateral approach. The implantable prostheses disclosed herein may be implanted using any number of approaches (including an anterior lumbar approach), but may be most beneficial with the transforaminal lumbar interbody fusion (TLIF) and lateral approaches. In particular, implantable prostheses of the present embodiments may provide a larger footprint with a smaller incision or annulotomy. While traditional transforaminal lumbar interbody fusion devices (e.g., cages) may typically be about 7 mm to 10 mm deep by about 25 mm in length, the implantable prosthesis of the present embodiments may axially or laterally expand up to about 28 mm in diameter, offering greater stability and potentially better surgical outcomes. The minimally invasive surgical approaches afforded by the implantable prostheses of the present embodiments may facilitate outpatient lumbar fusion procedures, reducing the cost of patient care and lessening the chance of post-surgical infections due to hospital stays. In so doing, the present embodiments may help lower overall treatment costs by shortening or eliminating hospital stays.

As shown in FIG. 15.1, transforaminal lumbar interbody fusion implantation may begin after the surgical site has been cleared and prepared to receive the implantable prosthesis. For example, with a spinal implantation, an annulotomy followed by a discectomy may be performed, which clears the intervertebral space and distracts the endplates of the vertebral bodies to provide the space necessary to receive the implantable prosthesis. In FIG. 15.1, the intervertebral space 1950 has been cleared.

With the intervertebral space cleared, implantation may continue by packing an anterior portion of the intervertebral space 1950 with an anterior bone growth promoting agent 1952, such as an autograft, allograft, or demineralized bone matrix (DBM). In FIG. 15.1, the bone growth promoting agent 1952 has already been inserted using the graft delivery instrument 1954.

Following insertion of the bone growth promoting agent 1952, an implant deployment device 1956, with an implantable prosthesis retracted into the device 1956 in a substantially linear configuration, may be inserted into the annulotomy window and into the disc space a proper depth and position within the intervertebral space 1950. At this point, the proper position of the distal tip 1957 of the implant deployment device 1956 may be confirmed with fluoroscopy.

When the implant deployment device 1956 is properly positioned, the graft delivery instrument 1954 may be used to insert additional bone growth promoting agent 1958 into the intervertebral space 1950 near the distal tip 1957 of the implant deployment device 1956. The graft delivery instrument 1954 may then be removed from the intervertebral space 1950, leaving the implant deployment device 1956 in place in the intervertebral space 1950.

As shown in FIG. 15.2, with both bone growth promoting agents 1952, 1958 in place, the implantation procedure may continue by advancing the implantable prosthesis 1999 out of the distal tip 1957 of the implant deployment device 1956. The implantable prosthesis 1999 may coil around and over the bone growth promoting agent 1958 located at the distal tip 1957 of the implant deployment device 1956. FIG. 15.3 illustrates the implantable prosthesis 1999 substantially fully deployed and coiled within the intervertebral space 1950. At this point, the implant deployment device 1956 may be removed from the intervertebral space 1950.

As shown in FIG. 15.4, with the implantable prosthesis 1999 and the bone growth promoting agents 1952, 1958 in place, the fusion procedure may continue by inserting graft delivery instrument 1954 into the intervertebral space 1950 and packing a lateral portion of the intervertebral space 1950 with a bone growth promoting agent 1960.

Turning now to lateral implantation, as shown in FIG. 16.1, lateral implantation may begin after the surgical site has been cleared and prepared to receive the implantable prosthesis. For example, with a spinal implantation, an annulotomy followed by a discectomy may be performed, which clears the intervertebral space and distracts the endplates of the vertebral bodies to provide the space necessary to receive the implantable prosthesis. In FIG. 16.1, the intervertebral space 1970 has been cleared.

With the intervertebral space cleared, implantation may continue by inserting an implant deployment device 1976, with an implantable prosthesis retracted into the device 1976 in a substantially linear configuration, into the annulotomy window to a proper depth and position within the intervertebral space 1970. At this point, the proper position of the distal tip 1977 of the implant deployment device 1976 may be confirmed with fluoroscopy.

As shown in FIG. 16.1, a graft delivery instrument 1974 may then be inserted into the intervertebral space 1970, with the outlet of the instrument 1974 near the distal tip 1977 of the implant deployment device 1976. Bone growth promoting agent 1978 may then be deposited from the outlet of the graft delivery instrument 1974, near the distal tip 1977 of the implant deployment device 1976. The graft delivery instrument 1974 may then be removed from the intervertebral space 1970, leaving the implant deployment device 1976 and bone growth promoting agent 1978 in place in the intervertebral space 1970.

As shown in FIGS. 16.2-16.3, the implantation procedure may continue by advancing the implantable prosthesis 1999 out of the distal tip 1977 of the implant deployment device 1976. The implantable prosthesis 1999 may coil around and over the bone growth promoting agent 1978 located at the distal tip 1977 of the implant deployment device 1976. FIG. 16.3 illustrates the implantable prosthesis 1999 substantially fully deployed and coiled within the intervertebral space 1970. At this point, the implant deployment device 1976 may be removed from the intervertebral space 1970.

With the implantable prosthesis 1999 and bone growth promoting agent 1978 in place, the lateral fusion procedure may continue by packing lateral portions of the intervertebral space 1970 with bone growth promoting agent 1980 on one side as shown in FIG. 16.4, and with bone growth promoting agent 1972 on the opposite side as shown in FIG. 16.5. The graft delivery instrument 1976 may then be removed from the intervertebral space 1970, leaving the implantable prosthesis 1999 and bone growth promoting agents 1978, 1972, 1980 in their final implantation positions.

Embodiments of implantable prostheses may include provisions for facilitating a proper fit in an implantation site. In an intervertebral space, for example, the lengths of the biased coiling member and the conforming coiling member may be selected to provide a coiled configuration with a lateral coiled width appropriate to fill the lateral width of the intervertebral space. In addition, in embodiments, an implantable prosthesis may be height-adjustable in the spinal axis direction within an intervertebral space, so that the upper and lower surfaces of the implantable prosthesis adequately contact the upper and lower vertebral bodies and provide a desired level of structural support. In embodiments, a height-adjustable implantable prosthesis may have a first height (e.g., shorter height) before deployment and during insertion into the implantation site, and may be adjustable to a second height (e.g., taller height) after insertion to properly fit the distance between the vertebral bodies or even push the vertebral bodies farther apart to a desired increased distance.

In providing an adjustable height, embodiments of an implantable prosthesis may include a conforming coiling member having upper and lower components that may move relative to each other, and a biased coiling member that actuates the upper and lower components to move toward or away from each other. In one embodiment, a biased coiling member may move pins or posts positioned in inclined slots of the conforming coiling member to raise or lower the upper component of the conforming coiling member relative to the lower component of the conforming coiling member. In another embodiment, a biased coiling member may have inclined surfaces that cooperate with corresponding inclined surfaces of the upper and lower components of the conforming coiling member, to raise or lower the upper component relative to the lower component (i.e., jack-up the disc space).

FIGS. 17.1-17.12 illustrate views of an embodiment of a height-adjustable implantable prosthesis 2600. As shown, implantable prosthesis 2600 may include a conforming coiling member 2601 comprising a plurality of segments 2642 and a narrower biased coiling member 2602 (or members) contained internally within the segments 2642. As described above, for example in reference to FIG. 11, conforming coiling member 2601 and biased coiling member 2602 may be engaged to each other, while still able to move longitudinally relative to each other, to allow transition from a substantially linear configuration to a nonlinear configuration or to provide height-adjustment as described below. In addition, each segment 2642 of conforming coiling member 2602 may include an upper component 2642A and a lower component 2642B, which may move relative to each other. Each segment 2642 may also define an internal passageway 2608 in which the biased coiling member 2602 is disposed. Although in the embodiment of FIG. 17.1, implantable prosthesis 2600 has three segments 2642, other embodiments may use greater or fewer numbers of segments, for example, depending on the configuration of the intervertebral space and the desired size and shape of the implanted implantable prosthesis.

In assembling the implantable prosthesis 2600, after inserting the biased coiling member 2602 into the passageway 2608, at each segment 2642 a pin 2604 may be inserted through an opening 2607 defined in the biased coiling member 2602, an inclined slot 2610 defined in the upper component 2642A, and an inclined slot 2612 defined in the lower component 2642B (for illustration purposes, FIG. 17.1 shows only one pin 2604 installed, with two other pins yet to be installed). Slot 2610 and slot 2612 may be inclined in opposite directions, as shown for example in FIG. 17.8. The pin 2604 may be fixed to the biased coiling member 2602 by a press fit and may be slidable within the slot 2610 and slot 2612. At each segment 2642, the pin 2604 may slide within the opposing inclined slots 2610 and 2612, thereby facilitating unified vertical expansion of the segments 2642 in the curved configuration of the implantable prosthesis 2600.

Implantable prosthesis 2600 may further include an actuator 2620 for moving the biased coiling member 2602 within the passageway 2608 and relative to the conforming coiling member 2601. In embodiments, actuator 2620 may include a housing 2622 and a set screw 2624. The housing 2622 may have an opening 2623 to guide the biased coiling member 2602 into the actuator 2620 and in alignment with the set screw 2624. The set screw 2624 may cooperate with corresponding openings 2626 defined in the biased coiling member 2602. Set screw 2624 may be turned using an appropriately shaped and sized tool inserted into opening 2628. Rotating set screw 2624 in a first direction (e.g., clockwise or counter-clockwise) may move biased coiling member 2602 through conforming coiling member 2601 and toward actuator 2620, while rotating set screw 2624 in a second direction opposite to the first direction may move biased coiling member 2602 through conforming coiling member 2601 and away from actuator 2620. In one implementation, rotating set screw 2624 clockwise may push biased coiling member 2602 out of housing 2622 of actuator 2620, while rotating screw 2624 counterclockwise may pull biased coiling member 2602 into housing 2622.

Upon tightening set screw 2624 at the proximal end 2621 of the implantable prosthesis 2600, the set screw 2624 may pull the biased coiling member 2602 through conforming coiling member 2601 and toward the actuator 2620, and in turn pull the pins 2604 in unison toward the actuator 2620. At each segment 2642, the pulling force may move the pin 2604 within the inclined slots 2610 and 2612 to push the upper component 2642A away from the lower component 26428 and thereby expand the implantable prosthesis 2600 vertically to, e.g., fill an intervertebral disc space. The slots 2610 and 2612 may be inclined in opposite directions so that movement of a pin 2604 toward the proximal end of the implantable prosthesis 2600 causes the pin 2604 to push up on the upper edge of the slot 2610 of the upper component 2642A and push down on the lower edge of the slot 2612 of the lower component 2642B. FIG. 17.2 illustrates pins 2604 at an initial position before vertical expansion. FIG. 17.10 illustrates pins 2604 at a midpoint position during vertical expansion. FIG. 17.8 illustrates pins 2604 at an end position after full vertical expansion.

In embodiments, referring to FIGS. 17.2, 17.8, and 17.9, implantable prosthesis 2600 may have an implanted width 2680 ranging from about 10 mm to about 60 mm, and an implanted depth 2683 ranging from about 10 mm to about 30 mm, and may increase in height from an initial height 2681 ranging from about 5 mm to about 14 mm, to an end height 2682 ranging from about 6 mm to about 20 mm. These implantable prostheses may be delivered through a cannula. In implementations, implantable prostheses may come in various sizes ranging from smaller sizes (e.g., extra-small) to larger sizes (e.g., extra-large).

A pin 2604 may also serve to retain assembly of each of the components 2642A and 2642B of a segment 2642 and the assembly of the implantable prosthesis 2600 as a whole. A tongue and groove arranged between an upper component 2642A and a lower component 2642B, in conjunction with the interdigitating of the layers, may restrict motion, but may allow the vertical expansion of each segment 2642. The substantially central gap between the components 2642A and 2642B may be configured to engage and constrain most relative movement except for vertical expansion of the segments 2642 and the coiling-and-uncoiling-to-flat of the biased coiling member 2602, including the relative displacement between biased coiling member 2602 and the conforming coiling member 2601 that may occur in transitioning from a substantially linear configuration to a nonlinear configuration.

At each segment 2642, a pin 2604 may be loaded in shear at multiple locations simultaneously by the layering effect of the interdigitating of the components 2642A and 2642B, thereby increasing allowable load. The tension on the biased coiling member 2602 may also greatly increase the force generated to maintain the curved configuration of the implantable prosthesis 2600. Lordosis angles can be formed into the appropriate segments 2642 so that the assembled implantable prosthesis 2600 has coplanar angled surfaces on the inferior and superior vertebral end plates. Grooves 2648 on the top and bottom surfaces of segments 2642 may track the implantable prosthesis 2600 into place in the curved configuration and aid the permanent registration with the vertebral end plates.

FIG. 17.1 illustrates an isometric outside detail view of the implantable prosthesis 2600 as the pins 2604 are being inserted to lock the assembly. For illustration purposes, FIG. 17.1 shows only one pin 2604 installed, with two other pins yet to be installed.

FIG. 17.2 illustrates an isometric outside detail view of a portion of the implantable prosthesis 2600 with the pins 2604 in place to lock the assembly and facilitate expansion.

FIG. 17.3 illustrates an isometric top partial cross-sectional view of a portion of the implantable prosthesis 2600, with portions of a segment 2642 hidden to show the engagement between pin 2604, upper component 2642A, and biased coiling member 2602.

FIG. 17.4 illustrates an isometric top partial cross-sectional view of a portion of the implantable prosthesis 2600, with portions of a segment 2642 hidden to show the engagement between pin 2604, lower component 2642B, and biased coiling member 2602.

FIG. 17.5 illustrates an isometric detail view of the implantable prosthesis 2600 with the segments 2642 hidden to show the engagement between pins 2604, biased coiling member 2602, and actuator 2620.

FIG. 17.6 illustrates an isometric detail view of a portion of the implantable prosthesis 2600 with the segments 2642 and the housing 2622 of the actuator 2620 hidden to show the engagement between the pins 2604 and the biased coiling member 2602, and the engagement between the tightening screw 2624 of the actuator 2620 and the biased coiling member 2602.

FIG. 17.7 illustrates an isometric detail end view of a portion of the implantable prosthesis 2600 in the minimal expansion state, with components 2642A and 2642B of a segment 2642 shown in different shading to illustrate the engagement between a pin 2604 and slots 2610 and 2612, and to illustrate the interdigitating components 2642A and 2642B with the biased coiling member 2602.

FIG. 17.8 illustrates an isometric detail view of a portion of the implantable prosthesis 2600 in the maximum expansion state, showing the engagement between pins 2604 and slots 2610 and 2612 and the interdigitating of the components 2642A and 2642B of the segments 2642. For purposes of illustration and clarity, the actuator 2620 is omitted from the view of FIG. 17.8.

FIG. 17.9 illustrates an isometric inside detail view of a portion of the implantable prosthesis 2600 in a mid-expansion state, showing the tongue and groove connection between the components 2642A and 2642B of the segments 2642.

FIG. 17.10 illustrates an isometric outside detail view of a portion of the implantable prosthesis 2600 in a mid-expansion state, showing the engagement between pins 2604 and slots 2610 and 2612 and the interdigitating of the components 2642A and 2642B of the segments 2642.

FIG. 17.11 illustrates an isometric detail cross-sectional view of a distal portion 2625 of the implantable prosthesis 2600 in a minimal expansion state, with the upper component 2642A and the lower component 2642B shown in different shading to illustrate the engagement between pins 2604 and slots 2610 and 2612, the interdigitating of the components 2642A and 2642B of the segments 2642, and the passageway 2608 defined between the components 2642A and 2642B permitting motion of the biased coiling member 2602 between straight and curved states.

In embodiments, the implantable prosthesis 2600 of FIGS. 17.1-17.12 may include provisions for incrementally adjusting the height of the implantable prosthesis 2600 and for minimizing the tensile loads on the biased coiling member 2602 in vitro. In some embodiments, the loaded inclined surfaces of slots 2610 and 2612 (e.g., surface 2651 shown in FIG. 17.2) may include sequential recesses (e.g., detent grooves, or recesses similar to the divots of a serrated knife) so that at each segment 2642 the pin 2604 may seat in matching indentations on both components 2642A and 2642B of the segment 2642. In one embodiment, FIG. 17.12 illustrates recesses 2655 in slots 2610 and 2612, into which pin 2604 may seat. This configuration may greatly minimize the tensile load on the biased coiling member 2602 when implanted and under compressive loads, and may also permit the implantable prosthesis 2600 to be adjusted incrementally in predetermined increments. With this configuration, in vitro compression loads may seat the pin in recesses 2655 without applying transferred and compounded tensile loads to the tensioning member (e.g., biased coiling member). Although FIG. 17.12 illustrates recesses 2655 on the top edge of slot 2610 and the bottom edge of slot 2612 (which edges may be under compression load when the implantable prosthesis 2600 is implanted) and straight edges on the bottom edge of slot 2610 and the top edge of slot 2612, other configurations are possible, such as having recesses on the top and bottom edges of slots 2610 and 2612. The configuration of FIG. 17.12 may allow slots 2610 and 2612 to be of minimum width to eliminate slop while in the detent position, while providing the same or similar positioning rigidity under compression load as a configuration with recesses in both the top and bottom edges of the slots 2610 and 2612. Other shapes of recesses and pins are also possible, which may cooperate with each other.

In embodiments, the segments 2642 of implantable prosthesis 2600 may be made (e.g., machined or molded) from any biocompatible materials approved for implant in the human body, such as an implantable-grade polymer, including but not limited to PEEK, PEKK, PLLA, or polyethene; or an implantable-grade metal, including but not limited to titanium, titanium alloy, or stainless steel; or any biocompatible material including but not limited to biological matrices, carbon fiber, ceramics, or any composites. These segments can also be produced with an additive manufacturing process, such as laser or electron beam fused particles in the materials listed above. The biased coiling member 2602 may be made of shape memory materials, such as but not limited to titanium, titanium alloy, stainless steel, nitinol, polymers, biological matrices, ceramics, or any biocompatible material, and may be deflected to the flat state for assembly, sterilization, and distribution, without permanent deformation.

FIGS. 18.1-18.7 illustrate embodiments for inserting an implantable prosthesis, such as the implantable prosthesis embodiments shown in FIGS. 17.1-17.12, into a surgical site. The implantable prostheses disclosed in FIGS. 17.1-17.12 may be implanted using any number of approaches, including posterior, lateral, anterior lumbar, and traditional open approaches. The implantable prostheses of the embodiments of FIGS. 17-1-17.12 may provide a larger footprint with a smaller incision or annulotomy. The minimally invasive surgical approaches may facilitate outpatient lumbar fusion procedures, reducing the cost of patient care, lessening the chance of post-surgical infections due to hospital stays, and helping to lower the overall treatment costs by shortening or eliminating hospital stays.

Referring to FIG. 18.1, implantation may begin after the surgical site has been cleared and prepared to receive the implantable prosthesis. For example, with a spinal implantation, an annulotomy followed by a discectomy may be performed, which clears the intervertebral space and distracts the endplates of the vertebral bodies to provide the space necessary to receive the implantable prosthesis. As shown, the implantable prosthesis 2600 may be disposed in a cannula 2652 of an implant deployment device 2650 in a pre-deployment substantially linear configuration. An actuating tool 2654 of the implant deployment device 2650 may be connected to the actuator 2620 of the implantable prosthesis 2600.

As shown in the progressive views of FIGS. 18.1 through 18.4, implantation may continue by advancing the implantable prosthesis 2600 out of the distal tip 2657 of the implant deployment device 2650. Portions of the implantable prosthesis 2600 may coil or curve as they exit the distal tip 2657, due to the biased coiling member 2602 curving the conforming coiling member 2601 (i.e., the plurality of segments). As the implantable prosthesis 2600 coils, the conforming coiling member 2601 and biased coiling member 2602 may longitudinally displace relative to each other to facilitate proper coiling. As shown, for example, in FIG. 18.1, the ends 2659 of each segment of a conforming coiling member may be configured (e.g., angled or contoured) to limit the degree to which the implantable prosthesis 2600 may coil or curve. As shown, the segments may be wedge-shaped, with the biased coiling member holding the segments against each other at angled contact surfaces of the wedge shape.

The implantable prosthesis 2600 may be advanced by pushing the implantable prosthesis 2600 with the actuator tool 2654 of the implant deployment device 2650. The implantable prosthesis 2600 may be advanced until all of the segments have exited the cannula 2652, with the actuator 2620 remaining inside the cannula, still attached to the actuator tool 2654. As shown, at this point, the implantable prosthesis 2600 may assume a curved, or crescent, shape within the intervertebral space. The proper position of the distal tip 2657 of the implant deployment device 2650 may be confirmed with fluoroscopy.

In this position, as shown in FIGS. 18.4 and 18.5, the height of the implantable prosthesis 2600 may then be adjusted. As represented by the arrow 2653 in FIG. 18.5, the actuator tool 2654 may be rotated to increase the height of the implantable prosthesis 2600 from the initial height 2681 to the end height 2682. As described above in reference to FIGS. 17.1-17.12, the actuator 2620 may move the biased coiling member within the conforming coiling member to adjust the height of the implantable prosthesis 2600.

With the implantable prosthesis 2600 adjusted to the desired height, the implantation procedure may continue as shown in FIG. 18.6, by inserting a bone growth promoting agent 2662, such as an autograft, allograft, or demineralized bone matrix (DBM), within the intervertebral space, next to the implantable prosthesis 2600. The bone growth promoting agent 2662 may be inserted using a graft delivery instrument 2664 inserted through an annulotomy and into the intervertebral space. In an embodiment, the bone growth promoting agent 2662 may occupy the area within the inside curve of the implantable prosthesis 2600. That area may provide a relatively large graft area.

With the implantable prosthesis 2600 and bone growth promoting agent 2662 in place in the intervertebral space, the graft delivery instrument 2664 may be removed from the intervertebral space. Then, the actuator tool 2654 of the implant deployment device 2650 may be disconnected from the actuator 2620 of the implantable prosthesis 2600, and the implant deployment device 2650 may be removed from the intervertebral space, as represented by the arrow 2667 in FIG. 18.7.

FIGS. 19.1-19.10 illustrate views of another embodiment of a height-adjustable implantable prosthesis 2700. As shown, implantable prosthesis 2700 may include a conforming coiling member 2701 comprising a plurality of segments 2742 and a biased coiling member 2702 (or members) contained internally within the segments 2742. Each segment 2742 may include an upper component 2742A and a lower component 2742B, which may move relative to each other. Each segment 2742 may also define an internal passageway 2708 in which the biased coiling member 2702 is disposed. As described above, for example in reference to FIG. 11, conforming coiling member 2701 and biased coiling member 2702 may be engaged to each other, while still able to move longitudinally relative to each other, to allow transition from a substantially linear configuration to a nonlinear configuration or to provide height-adjustment as described below.

Upper component 2742A and lower component 2742B may have one or more inclined surfaces 2760 formed into internal surfaces to mate with corresponding inclined surfaces 2762 formed into the biased coiling member 2702, to provide vertical expansion in unison in each segment 2742. The components 2742A and 2742B may be configured with tongue and groove type connections to provide controlled parallel motion, with most or all other movement restricted. Components 2742A and 2742B may have mating protrusions 2752A and 2752B configured to stop vertical over travel and disassembly. As shown, for example, in FIGS. 19.9 and 19.10, the distal end segment 2742 may be slidably connected to the biased coiling member 2702. The slidable connection may be achieved by a pin 2704 that engages a slot 2710 defined in the biased coiling member 2702 and an opening 2711 defined in the lower component 2742B of the distal end segment 2742. The slidable connection retains the distal end segment 2742 along the biased coiling member 2702, while allowing the biased coiling member 2702 to move toward and away from the distal end segment 2742 along the length of the implantable prosthesis 2700.

In assembling implantable prosthesis 2700, the mating upper component 2742A and lower component 2742B may be slid together in the vertical direction and then the biased coiling member 2702 may be inserted into the passageway 2708. This sequence may block the vertical disassembly by eliminating the needed clearance for the opposing protrusions 2752A and 2752B to clear each other.

Implantable prosthesis 2700 may further include an actuator 2720 for moving the biased coiling member 2702 within the passageway 2708. In embodiments, actuator 2720 may include a housing 2722 and a set screw 2724. The housing 2722 may have an opening 2723 to guide the biased coiling member 2702 into the actuator 2720 and in alignment with the set screw 2724. The set screw 2724 may cooperate with corresponding openings 2726 defined in the biased coiling member 2702. Set screw 2724 may be turned using an appropriately shaped and sized tool inserted into opening 2728. Rotating set screw 2724 in a first direction (e.g., clockwise or counter-clockwise) may move biased coiling member 2702 through conforming coiling member 2701 and toward actuator 2720, while rotating set screw 2724 in a second direction opposite to the first direction may move biased coiling member 2702 through conforming coiling member 2701 and away from actuator 2720.

Upon tightening set screw 2724 at the proximal end of the implantable prosthesis 2700, the set screw 2724 may pull the biased coiling member 2702 through conforming coiling member 2701 and toward the actuator 2720, and in turn pull in unison in a direction toward the actuator 2720 each of the inclined surfaces 2762 of biased coiling member 2702 against corresponding inclined surfaces 2760 of segments 2742. Accordingly, at each segment 2742, the inclined surfaces 2760 and 2762 sliding against each other push the upper component 2742A away from the lower component 2742B and thereby expand the implantable prosthesis 2700 vertically to, e.g., fill an intervertebral disc space. The inclined configuration of the slot 2710 of the biased coiling member 2702 allows the biased coiling member 2702 to move within the distal end segment 2742 and allows the upper component 2742A to rise away from the lower component 2742B, while also retaining the biased coiling member 2702 within the segments 2742 of the implantable prosthesis 2700. When the pin 2704 reaches the upper distal end of the slot 2710, the biased coiling member 2702 may be fully tightened and the segments 2742 may be fully expanded. In embodiments, mating recesses and protrusions (e.g., a series of ramps and flat steps) may be provided on mating inclined surfaces 2760 and 2762 to provide incremental height adjustment of the implantable prosthesis 2700, which may minimize tensile load on the biased coiling member 2702 when implanted and under compressive loads. In addition to or as an alternative to the incrementally-contoured mating inclined surfaces 2760 and 2762, incremental height adjustment may be provided by recesses in slot 2710 that cooperate with the pin 2704, as with the implantable prosthesis 2600 of FIGS. 17.1-17.12 described above.

The tension on the biased coiling member 2702 may also greatly increase the force generated to maintain the curved configuration of the implantable prosthesis 2700. Lordosis angles can be formed into the appropriate segments 2742 so that the assembled implantable prosthesis 2700 has coplanar angled surfaces on the inferior and superior vertebral end plates. Grooves 2748 on the top and bottom surfaces of segments 2742 may track the implantable prosthesis 2700 into place in the curved configuration and aid the permanent registration with the vertebral end plates.

FIG. 19.1 illustrates an outside detail partial view of an embodiment of a portion of an implantable prosthesis 2700 at a midpoint of vertical expansion, shown in different shading to illustrate the opposing protrusions 2752A and 2752B that prevent disassembly. As shown, the protrusions 2752A of the upper component 2742A may be limited in depth to match the thickness of the biased coiling member 2702, thereby permitting assembly. In other words, during assembly of the implantable prosthesis 2700, the upper component 2742A may be tilted such that the protrusions 2752A of the upper component 2742A may slide down the passageway 2708 until reaching a point below the protrusions 2752B of the lower component 2742B, at which point the upper component 2742A may be leveled with the lower component 2742B so that the protrusions 2752A are vertically underneath the protrusions 2752B. The biased coiling member 2702 may then be inserted into the passageway 2708, which may prevent the upper component 2742A from tilting back and thereby prevent the protrusions 2752A from entering the passageway 2708 and clearing the protrusions 2752B. The inserted biased coiling member 2702 may therefore prevent disassembly of the upper component 2742A and the lower component 2742B.

FIG. 19.2 illustrates an outside detail view of a portion of the implantable prosthesis 2700 with a segment 2742 hidden to show the inclined surfaces 2762 of the biased coiling member 2702, which engage with mating inclined surfaces 2760 on the segments 2742 (shown, for example, in FIG. 19.10).

FIG. 19.3 illustrates a proximal isometric view of a portion of the implantable prosthesis 2700 with two and one-half segments 2742 hidden to show the actuator 2720 including a screw 2724 and a housing 2722. As shown, the distal end segment 2742 may have an opening 2711 and the biased coiling member 2702 may have an inclined slot 2710 to receive a pin 2704 used to retain the distal end segment 2742. As also shown, the distal end segment 2742 may have short length protrusions 2752B to prevent vertical disassembly of each segment.

FIG. 19.4 illustrates an isometric detail view of the tightening screw 2724 of the implantable prosthesis 2700, engaged with mating slots 2726 defined in the biased coiling member 2702 and used for height expansion of the implantable prosthesis 2700.

FIG. 19.5 illustrates an isometric cross-sectional view of the actuator 2720 of the implantable prosthesis 2700, with tightening screw 2724 engaged with mating slots 2726 in the biased coiling member 2702 and used for height expansion of the implantable prosthesis 2700. Housing 2722 may have a shouldered bore for the tightening screw 2724, which bore may be adjacent to a rectangular opening 2723 configured to receive the slotted end of the biased coiling member 2702. Also shown is a passageway 2708 defined between the components 2742A and 2742B, configured to slidably contain the biased coiling member 2702 in both the straight and curved states.

FIG. 19.6 illustrates an isometric inside view of a portion of the implantable prosthesis 2700 in a mid-expanded state. As shown, segments 2742 may have protruding circular grooves 2748 to assist in the tracking and curvature of the implantable prosthesis 2700 during implantation.

FIG. 19.7 illustrates an isometric inside view of the implantable prosthesis 2700 in the closed state, with the tightening screw 2724 and housing 2722 of the actuator 2720 in the view.

FIG. 19.8 illustrates an isometric inside detail view of a portion of the implantable prosthesis 2700 in a fully expanded state. As shown, segments 2742 may have protruding circular grooves 2748 to assist in the implantable prosthesis 2700 biting into the vertebral endplates under compressive load when implanted.

FIG. 19.9 illustrates an isometric inside cross-sectional view of a portion of the implantable prosthesis 2700 in a mid-expanded state, with different shading used to illustrate engagement details between the upper component 2742A and the lower component 2742B, and to illustrate how the distal end segment 2742 is retained by a pin 2704 inserted into a slot 2710 in the biased coiling member 2702.

FIG. 19.10 illustrates an isometric outside section view of a portion of the implantable prosthesis 2700 in the closed state, with a portion of the distal end segment 2742 hidden, and with different shading used to illustrate engagement details between the upper component 2742A and the lower component 2742B, to illustrate how the distal end segment 2742 is retained by a pin 2704 inserted into a slot 2710 in the biased coiling member 2702, and to illustrate the inclined surfaces 2762 on the biased coiling member 2702 that mate with the inclined surfaces 2760 on the upper component 2742A and the lower component 27428.

In embodiments, segments 2742 of implantable prosthesis 2700 may be machined to shape or formed by the Direct Metal Laser Sintering (DMLS) process or molded. In embodiments, the segments of implantable prosthesis 2700 may be made (e.g., machined or molded) from any biocompatible materials approved for implant in the human body, such as an implantable-grade polymer, including but not limited to PEEK, PEKK, PLLA, or polyethene; or an implantable-grade metal, including but not limited to titanium, titanium alloy, or stainless steel; or any biocompatible material including but not limited to biological matrices, carbon fiber, ceramics, or any composites. These segments can also be produced with an additive manufacturing process, such as laser or electron beam fused particles in the materials listed above. The biased coiling member may be made of spring tempered or shape memory materials, such as but not limited to titanium, titanium alloy, stainless steel, nitinol, polymers, biological matrices, ceramics, or any biocompatible material, and may be deflected to the flat state for assembly, sterilization, and distribution, without permanent deformation.

As evident from the above descriptions of exemplary implantable prosthesis and implantation procedures, embodiments may provide surprising beneficial results in surgical approaches. The embodiments may, for example, allow for minimally invasive surgeries or percutaneous discectomy through retractors or tube dilators. The implantable prosthesis also may be implanted using many other approaches, including traditional open approaches and thoracic approaches. The implantable prosthesis may be light weight yet extremely strong. The expanding and coiling delivery of the implantable prosthesis may allow the implantable prosthesis to take the shape of the intervertebral space, may provide a wide surface loading area, and may provide a balanced, symmetrical implant shape after implantation. The implantable prosthesis may also be radiolucent-, MRI-, and CT-compatible.

In addition, the implantable prosthesis may be removed if deployed in an unacceptable position by grasping the end of the implantable prosthesis at the outermost coil in the coiled configuration (e.g., by hooking a tool or instrument onto the instrument openings 1609 shown in FIGS. 12.1-12.3, 12.5, and 12.9-12.11 or to the actuator 2620 in FIGS. 17.1-17.12), and retracting the coil into a cannula of an implant deployment device. In embodiments, the proximal portion 1152 of a biased coiling member may be straightened, crimped, or otherwise formed to position the proximal end of the biased coiling member slightly above the outermost coil to allow an instrument to grasp the proximal end. This configuration may be helpful in initially loading an implantable prosthesis into an implant deployment device, and in retrieving an implantable prosthesis from a surgical site if removal or repositioning is desired. In addition, although embodiments disclosed herein illustrate two openings 1609 in an implantable prosthesis, any number, shape, or type of openings may be used, for example, as appropriate for cooperating with an implant deployment device. Embodiments may include one, two, three, or more openings, and may include, for example, circular openings, oblong openings, and rectangular openings. For example, instead of the two oblong openings 1609 shown in FIG. 12.1, a single circular opening centered at the proximal portion of the implantable prosthesis could be provided. As another example, a proximal portion of an implantable prosthesis may include openings similar to the openings 2626 shown in FIGS. 17.6, which may cooperate with a screw-thread-type tool of an implant deployment device.

The smaller annulotomy of the present embodiments may also allow for more convenient and quick procedures, with less pain, shorter hospital stays, and faster recovery times for patients. The smaller annulotomy, in comparison to the larger implantable prosthesis, may also reduce the incidents of expulsion.

The present embodiments also provide controlled, self-steering implantation, which does not involve damaging impact.

In the present embodiments, the configuration of the implantable prosthesis and the implantation techniques may also provide generous graft placement in three intervertebral locations, including the implant center and both lateral aspects. The graft may be squeezed vertically by an implantable prosthesis to contact end plates. In addition, the implant size and shape may be auto reproducible.

In embodiments, an implantable prosthesis such as prosthesis 1699 of FIG. 12.1 and prosthesis 2600 of FIG. 17.1 may include provisions for accommodating lordosis. In one implementation, one or both of the longitudinal edges of the biased coiling member 1600 and conforming coiling member 1610 may be shaped (e.g., tapered or includes troughs and crests) to provide a desired shape when coiled, such as a wedge shape. In one embodiment, an implantable prosthesis may provide a lordotic fusion coil angled at 5 degrees (2.5 degrees on each longitudinal edge), and may be approximately 10.5 mm in height and 25 mm in diameter. Examples of the types of differently shaped implantable prostheses applicable to the present embodiments are discussed in U.S. Patent Publication Number US 2014/0243980, published Aug. 28, 2014 (U.S. patent application Ser. No. 14/191,954, filed Feb. 27, 2014), which is herein incorporated by reference in its entirety. In another implementation, segments may be angled or otherwise configured to provide a lordotic shape.

In embodiments, an implantable prosthesis may include additional provisions for fusing with bone, such as vertebral endplates. For example, portions of the prostheses may be coated with the bone growth promoting agent to enhance bone ingrowth. As another example, portions of the prostheses may include structural features that help grip bone, such as patterned or textured surfaces on the superior and inferior surfaces of the prosthesis. In one aspect, FIG. 17.1 shows curved ridges 2643 on the tops and bottoms of each segment, which may bite into the vertebral end plates to lock the implant into location under compressive loads. In addition, the curved ridges 2643 may guide the implantable prosthesis into position as each following segment tracks in the groove produced by the leading segments. In this manner, an implantable prosthesis may be considered self-steering.

In any of the embodiments disclosed herein, an implantable prosthesis may include provisions for accommodating loads (e.g., compressive and shear loads) using desired portions of the implantable prosthesis. For example, an implantable prosthesis may be configured to accommodate loads using a biased coiling member, a conforming coiling member, or a combination of the biased coiling member and the conforming coiling member.

For example, a width of a conforming coiling member may be greater than a width of a biased coiling member, such that the conforming coiling member may bear a majority, or substantially all, of a load (e.g., compressive load) applied to the implantable prosthesis. FIGS. 17.1-17.12 illustrate embodiments in which a narrower biased coiling member is attached to a wider conforming coiling member.

As another example, a width of a conforming coiling member may be less than a width of a biased coiling member, such that the biased coiling member may bear a majority, or substantially all, of a load (e.g., compressive load) applied to the implantable prosthesis.

As another example, a biased coiling member and a conforming coiling member may be configured to share a load. For example, a biased coiling member and a conforming coiling member may have substantially equal widths such that they both may contact a vertebral body and provide support. As another example, a biased coiling member and a conforming coiling member may be positioned in series along the direction of the applied force, such that the biased coiling member and the conforming coiling member both provide support.

In any of the embodiments disclosed herein, an implantable prosthesis may be made of any materials suitable for implantation into a human body and suitable for the structural and operational demands of the components of the prosthesis. A biased coiling member, for example, may be made of a biocompatible shape memory material that biases the biased coiling member to a coiled configuration. Suitable shape memory materials may include, but are not limited to, metals such as titanium, titanium alloy, stainless steel, nitinol, spring tempered or hardened metals, and combinations of such materials. Other suitable shape memory materials may include polymers, biological matrices, ceramics, and any biocompatible materials. A conforming coiling member, for example, may be made of a biocompatible metal, such as, but not limited to, titanium, titanium alloy, or stainless steel, or may be made of a biocompatible polymer, such as, but not limited to, PEEK, PEKK, PLLA, or polyethene.

The different features and provisions of implantable prostheses discussed in this detailed description may be combined in different combinations, in addition to those combinations described herein. The different features and provisions may also be combined to create a spinal implantable prosthesis that maximizes the utility of the implantable prosthesis for a particular patient. Furthermore, a bone growth promoting agent may be applied to a portion or an entirety of an implantable prosthesis in concert with any other provisions described in this detailed description. Generally, a surgeon or medical expert may assess a patient and configure a spinal implantable prosthesis based on factors specific to the patient. In some cases, for example, a surgeon or medical expert may consider the location of the damaged tissue, size of the vertebrae, and anatomical shape of the vertebrae or spinal disc as factors in the design choice of an implantable prosthesis. In other cases, a particular combination of provisions of an implantable prosthesis may be chosen to correct scoliosis or spondylolisthesis. In still other cases, an implantable prosthesis may be configured to alleviate compression of the nerves in the spinal foramen and canal. Generally, an implantable prosthesis may be configured with particular provisions to approximate the natural biomechanics of the spine and provide for spinal continuity.

An implantable prosthesis may include provisions to change shape. In some embodiments, an implantable prosthesis with provisions to change shape may be constructed of a shape-memory material. An implantable prosthesis constructed of a shape-memory material may be configured in a first shape prior to implantation. After implantation, the implantable prosthesis may assume a second shape that is different from the first shape.

In some cases, a signal associated with implantation may trigger the implantable prosthesis to transform to the second shape. Generally, the signal associated with implantation may be any type of signal including, but not limited to, heat, light, a local chemical environment, or mechanical or electrical stimulation. For example, when an implantable prosthesis is implanted, the body temperature of a patient may trigger the implantable prosthesis to transform into a second shape.

Generally, an implantable prosthesis constructed of shape-memory material may form various types of second shapes following implantation. In some cases, the second shape may be an oval shape. In other cases, the second shape may be any desired shape, including a circular shape, a kidney shape, or a half-moon shape. Incisions to implant an implantable prosthesis constructed of shape-memory material may be smaller because the implantable prosthesis may assume a second shape without assistance from a surgeon.

It is also possible that an implantable prosthesis constructed of a shape-memory material may expand in size following implantation. This may allow an implantable prosthesis to be constructed with a smaller size. With this arrangement, an implantable prosthesis may be constructed with a first size. Following implantation, the implantable prosthesis may expand to a second size that is larger than the first size. In this manner, smaller incisions may be made to implant the implantable prosthesis. This can provide reduced trauma and faster healing rates following implantation of an implantable prosthesis constructed of shape-memory material.

In any of the embodiments described herein having segments (e.g., wedge segments), the segments may be made (e.g., machined or molded) from any biocompatible materials approved for implant in the human body, such as an implantable-grade polymer, including but not limited to PEEK, PEKK, PLLA, or polyethene; or an implantable-grade metal, including but not limited to titanium, titanium alloy, or stainless steel; or any biocompatible material including but not limited to biological matrices, carbon fiber, ceramics, or any composites. These segments can also be produced with an additive manufacturing process, such as laser or electron beam fused particles in the materials listed above.

In embodiments, curved ridges on each segment may bite into the vertebral end plates to lock the implant into location under compressive loads. In addition, the curved ridges may guide the implantable prosthesis into position as each following segment tracks in the groove produced by the leading segments.

Assembly may be accomplished by different methods. In one embodiment, segments may be slid over a biased coiling member, whereby a punched spring tab in the biased coiling member locks against an abutting surface on the segments to retain the segments from sliding back off (one way catches). In another embodiment, two small posts machined as part of the segments may be inserted into slots punched into a biased coiling member, and then the ends of the posts may be flared, for example, similar to a rivet head. Metal segments may be retained by cold deformation of the post ends. Plastic segments may be retained by hot deformation. The slot in a biased coiling member may be sufficiently long to accommodate the difference in center distance of the two posts engaged into the biased coiling member band, whether straight or curved.

An assembled implantable prosthesis may be held in a mostly straight condition (see, e.g., FIG. 18.1) inside a deployment cannula and the proximal end may be connected to a rod inside the cannula. The cannula containing the implantable prosthesis may be inserted into the intervertebral space after a completed discectomy and the rod may be pushed in the distal direction to insert the implantable prosthesis. As each segment clears the end of the cannula, it may be forced to conform to the curvature of the biased coiling member. The curvature may be a pre-shaped form matching the anatomical variation in disc voids with assorted heights and radii.

The segments may be configured to withstand compressive and shear loads encountered in a spinal column.

In any of the embodiments disclosed herein, the relative widths of a biased coiling member and conforming coiling member may be adjusted to support loads as desired. For example, loads may be shared by the biased coiling member (e.g., spring band) and conforming coiling member by making the biased coiling member as wide as or wider than the conforming coiling member. As another example, if the conforming coiling member is intended to support most or all loads, then the biased coiling member may be narrower than the conforming coiling member. In some embodiments, a biased coiling member (e.g., spring band) may be significantly wide, including wider than the conforming coiling member, to provide a greater coiling force to ensure the desired final coiled shape of the implantable prosthesis.

In embodiments, segments may have voids to permit and promote bone growth through and between the segments.

In embodiments, an interconnection between a biased coiling member and a conforming coiling member (such as the posts and openings), in conjunction with the curved shape of the implanted assembly, may result in abundant compression and shear strength for the implantable prosthesis.

In embodiments, segments may be arranged in an arc to partly fill the discectomy in the anterior direction, and may include a retention feature to secure the prostheses from migration or expulsion. This may be accomplished by tightening a proximal screw that wedges opposing posts of an implantable prosthesis into the adjoining vertebral end plates, thereby locking the prosthesis in place.

In embodiments, segments may be arranged in a nearly full circle resulting in a deployed prosthesis that is larger than the annulotomy needed to receive the pre-deployed straight prostheses.

Embodiments of implantable prostheses and implantation procedures have been successfully implemented on human cadavers, demonstrating the feasibility of implantation using minimally invasive approaches. The entire implantation surgery, including the discectomy, has been successfully performed on cadavers through a ⅞ inch inner diameter tube dilator placed through a 1 inch incision. In contrast, surgeons performing an open approach for spinal fusion surgery typically make an incision between 2.5 inches to 3 inches, and surgeons using a mini-open approach on average make an incision of 1.75 inches. The present embodiments provide the ability to deliver an implant with a very large footprint through a much smaller annulotomy (e.g., a 10 mm high by 25 mm diameter fusion coil implant may be implanted through a 12 mm annulotomy), thereby preserving the annulus and reducing the likelihood of implant expulsion. A smaller surgical incision and annulotomy may also offer the potential for outpatient lumbar fusion in simpler, straightforward cases. The reduction in hospital stays and related complications due to post-surgical infections during hospital stays may result in total savings related to a fusion procedure.

The present embodiments are related to U.S. Patent Publication Number US 2014/0243980, published Aug. 28, 2014 (U.S. patent application Ser. No. 14/191,954, filed Feb. 27, 2014), which is a continuation of U.S. Pat. No. 8,696,753, issued Apr. 15, 2014 (U.S. patent application Ser. No. 13/463,041, filed May 3, 2012), which is a continuation of U.S. Pat. No. 8,197,548, issued Jun. 12, 2012 (U.S. patent application Ser. No. 12/118,503, filed May 9, 2008), which is a continuation-in-part of U.S. Pat. No. 7,922,767, issued Apr. 12, 2011 (U.S. patent application Ser. No. 11/774,584, filed Jul. 7, 2007), all of which are herein incorporated by reference in their entirety.

While various embodiments have been described, the description is intended to be exemplary, rather than limiting and it will be apparent to those of ordinary skill in the art that many more embodiments and implementations are possible. Accordingly, the embodiments are not to be restricted except in light of the attached claims and their equivalents. Also, various modifications and changes may be made within the scope of the attached claims.

Further, in describing representative embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the present embodiments.

What is claimed is:

1. A method for implanting an implantable prosthesis in a surgical site, comprising:
    holding the implantable prosthesis in a substantially linear configuration, the implantable prosthesis having a biased coiling member engaged with a conforming coiling member,
    wherein the biased coiling member defines a longitudinal axis;
    inserting the implantable prosthesis, while in the substantially linear configuration, through an opening and into the surgical site;
    inserting a bone growth promoting agent into the surgical site proximate to a distal end of the implantable prosthesis;
    advancing the implantable prosthesis into the surgical site;
    curving the conforming coiling member with the biased coiling member as the implantable prosthesis advances such that the implantable prosthesis transitions from the substantially linear configuration to a nonlinear configuration and coils around the bone growth promoting agent; and
    releasing the implantable prosthesis into the surgical site with the bone growth promoting agent occupying an area within an inside curve of the released implantable prosthesis.

2. The method of claim 1, further comprising:
    inserting a prior bone growth promoting agent into the surgical site before inserting the implantable prosthesis into the surgical site; and
    curving the conforming coiling member with the biased coiling member as the implantable prosthesis advances such that the implantable prosthesis coils with the prior bone growth promoting agent disposed laterally outside of the coiling implantable prosthesis.

3. The method of claim 1, wherein after releasing the implantable prosthesis into the surgical site, the method further comprises packing a lateral portion of the surgical site with a subsequent bone growth promoting agent disposed laterally outside of the implantable prosthesis.

4. The method of claim 1, wherein the implantable prosthesis coils into at least one concentric ring around the bone growth promoting agent.

5. The method of claim 1, wherein the implantable prosthesis coils into multiple concentric rings around the bone growth promoting agent with gaps between adjacent concentric rings, and wherein at least a portion of the bone growth promoting agent is disposed within at least one gap of the gaps.

6. The method of claim 1, wherein the implantable prosthesis coils around the bone growth promoting agent generally along a curvature plane and squeezes the bone growth promoting agent such that at least a portion of the bone growth promoting agent moves perpendicularly relative to the curvature plane and contacts a bone of the surgical site.

7. The method of claim 1, wherein the surgical site comprises an intervertebral space,
    wherein the opening is positioned for a transforaminal lumbar interbody fusion implantation,
    wherein the method further comprises packing an anterior portion of the intervertebral space with an anterior bone growth promoting agent before inserting the implantable prosthesis into the intervertebral space, and wherein after releasing the implantable prosthesis, the anterior bone growth promoting agent is disposed between a wall of the intervertebral space and an outer surface of an outermost coil of the implantable prosthesis.

8. The method of claim 7, further comprising, after releasing the implantable prosthesis, packing a lateral portion of the intervertebral space with a lateral bone growth promoting agent, wherein the lateral bone growth promoting agent is disposed between a wall of the intervertebral space and an outer surface of the outermost coil of the implantable prosthesis.

9. The method of claim 7, further comprising moving, with the coiling implantable prosthesis, at least a portion of the anterior bone growth promoting agent to a lateral portion of the intervertebral space as the implantable prosthesis coils.

10. The method of claim 1, wherein the surgical site comprises an intervertebral space, wherein the opening is positioned for a lateral implantation and the intervertebral space has a first lateral portion and a second lateral portion opposite to the first lateral portion, wherein the method further comprises, after releasing the implantable prosthesis, packing the first lateral portion of the intervertebral space with a first lateral bone growth promoting agent, and wherein the first lateral bone growth promoting agent is disposed between a wall of the intervertebral space and an outer surface of an outermost coil of the implantable prosthesis.

11. The method of claim 10, further comprising packing the second lateral portion of the intervertebral space with a second lateral bone growth promoting agent, wherein the second lateral bone growth promoting agent is disposed between a wall of the intervertebral space and an outer surface of the outermost coil of the implantable prosthesis.

12. The method of claim 1, wherein the biased coiling member is substantially fixed to the conforming coiling member in a direction lateral to the longitudinal axis, and wherein as the implantable prosthesis transitions from the substantially linear configuration to the nonlinear configuration, the biased coiling member and the conforming coiling member move relative to each other along the longitudinal axis and coil within themselves.

13. The method of claim 1, wherein holding the implantable prosthesis in the substantially linear configuration comprises holding the implantable prosthesis in a cannula, wherein inserting the implantable prosthesis, while in the substantially linear configuration, through the opening and into the surgical site comprises inserting the cannula through the opening and into the surgical site, wherein inserting the bone growth promoting agent into the surgical site proximate to the distal end of the implantable prosthesis comprises inserting the bone growth promoting agent near a distal tip of the cannula, wherein advancing the implantable prosthesis into the surgical site comprises advancing the implantable prosthesis toward the distal tip of the cannula and ejecting the implantable prosthesis from the cannula, and wherein releasing the implantable prosthesis into the surgical site comprises releasing the implantable prosthesis from the cannula.

14. The method of claim 1, wherein the bone growth promoting agent comprises at least one of an autograft, an allograft, a demineralized bone matrix, or a bone morphogenetic protein.

15. A method for implanting an implantable prosthesis in an intervertebral surgical site, comprising:

holding the implantable prosthesis in a substantially linear configuration, the implantable prosthesis having a biased coiling member engaged with a conforming coiling member;

inserting a bone growth promoting agent into the intervertebral surgical site;

inserting the implantable prosthesis, while in the substantially linear configuration, through an opening and into the intervertebral surgical site;

advancing the implantable prosthesis into the intervertebral surgical site;

curving the conforming coiling member with the biased coiling member as the implantable prosthesis advances such that the implantable prosthesis coils from the substantially linear configuration to a nonlinear configuration;

increasing a height of the implantable prosthesis and squeezing the bone growth promoting agent vertically with the implantable prosthesis such that the bone growth promoting agent contacts a bone of the intervertebral surgical site; and releasing the implantable prosthesis into the intervertebral surgical site.

16. The method of claim 15, wherein the bone growth promoting agent occupies an area within an inside curve of the released implantable prosthesis.

17. The method of claim 15, wherein the implantable prosthesis coils into at least one concentric ring around the bone growth promoting agent.

18. The method of claim 15, wherein holding the implantable prosthesis in the substantially linear configuration comprises holding the implantable prosthesis in a cannula, wherein inserting the implantable prosthesis, while in the substantially linear configuration, through the opening and into the intervertebral surgical site comprises inserting the cannula through the opening and into the intervertebral surgical site, wherein advancing the implantable prosthesis into the intervertebral surgical site comprises advancing the implantable prosthesis toward a distal tip of the cannula and ejecting the implantable prosthesis from the cannula, and wherein releasing the implantable prosthesis into the intervertebral surgical site comprises releasing the implantable prosthesis from the cannula.

19. The method of claim 15, wherein the conforming coiling member has a proximal end portion and a distal end portion, wherein the biased coiling member curves the conforming coiling member from the substantially linear configuration to the nonlinear configuration generally along a curvature plane, wherein an actuator is disposed at the proximal end portion of the conforming coiling member, wherein the conforming coiling member has a segment having a first component and a second component, wherein the first component and the second component move relative to each other in a height-adjusting direction generally perpendicular to the curvature plane, wherein the actuator is configured to hold the conforming coiling member and move the biased coiling member relative to the conforming coiling member, wherein at the distal end portion of the conforming coiling member, the biased coiling member is attached to the conforming coiling member by an inclined slidable connection that is inclined with respect to the curvature plane, wherein the inclined slidable connection allows relative movement between the first component and the second component, while maintaining the attachment between the biased coiling member and the conforming coiling member, and wherein increasing the height of the implantable prosthesis comprises moving, with the actuator, the biased coiling member relative to the conforming coiling member so as to cause the biased coiling member to move the first component relative to the second component in the height-adjusting direction.

20. The method of claim 19, wherein the segment comprises a first segment, wherein the conforming coiling member has a second segment adjacent to the first segment, and wherein the first segment and the second segment define a void to permit bone growth therethrough.

21. The method of claim 15, wherein the bone growth promoting agent comprises at least one of an autograft, an allograft, a demineralized bone matrix, or a bone morphogenetic protein.

22. A method for implanting an implantable prosthesis in a surgical site, comprising:

holding the implantable prosthesis in a substantially linear configuration, the implantable prosthesis having a biased coiling member engaged with a conforming coiling member;

depositing a mass of bone growth promoting agent into the surgical site;

inserting the implantable prosthesis, while in the substantially linear configuration, through an opening to the surgical site;

advancing the implantable prosthesis into the surgical site;

curving the conforming coiling member with the biased coiling member as the implantable prosthesis advances such that the implantable prosthesis transitions from the substantially linear configuration to a nonlinear configuration and coils around the mass of bone growth promoting agent; and releasing the implantable prosthesis into the surgical site with the mass of bone growth promoting agent occupying an area within an inside curve of the released implantable prosthesis.

* * * * *